(12) United States Patent
Oronsky

(10) Patent No.: US 11,744,859 B2
(45) Date of Patent: Sep. 5, 2023

(54) COMPOSITIONS AND METHODS FOR PARENTERAL ADMINISTRATION OF THERAPEUTIC AGENTS

(71) Applicant: EpicentRx, Inc., La Jolla, CA (US)

(72) Inventor: Bryan T. Oronsky, Los Altos Hills, CA (US)

(73) Assignee: EPICENTRX, INC., La Jolla, CA (US)

( * ) Notice: Subject to any disclaimer, the term of this patent is extended or adjusted under 35 U.S.C. 154(b) by 170 days.

(21) Appl. No.: 16/629,099

(22) PCT Filed: Jul. 6, 2018

(86) PCT No.: PCT/US2018/041138
§ 371 (c)(1),
(2) Date: Jan. 7, 2020

(87) PCT Pub. No.: WO2019/010447
PCT Pub. Date: Jan. 10, 2019

(65) Prior Publication Data
US 2020/0254016 A1 Aug. 13, 2020

Related U.S. Application Data

(60) Provisional application No. 62/565,808, filed on Sep. 29, 2017, provisional application No. 62/549,835, filed on Aug. 24, 2017, provisional application No. 62/534,639, filed on Jul. 19, 2017, provisional application No. 62/529,635, filed on Jul. 7, 2017.

(51) Int. Cl.
| | | |
|---|---|---|
| *A61K 36/00* | (2006.01) | |
| *A61K 35/16* | (2015.01) | |
| *A61P 35/00* | (2006.01) | |
| *A61K 31/282* | (2006.01) | |
| *A61K 31/337* | (2006.01) | |
| *A61K 31/407* | (2006.01) | |
| *A61K 31/4745* | (2006.01) | |
| *A61K 31/675* | (2006.01) | |
| *A61K 31/704* | (2006.01) | |
| *A61K 31/7042* | (2006.01) | |
| *A61K 35/15* | (2015.01) | |
| *A61K 47/46* | (2006.01) | |
| *A61K 9/00* | (2006.01) | |

(52) U.S. Cl.
CPC .......... *A61K 35/16* (2013.01); *A61K 31/282* (2013.01); *A61K 31/337* (2013.01); *A61K 31/407* (2013.01); *A61K 31/4745* (2013.01); *A61K 31/675* (2013.01); *A61K 31/704* (2013.01); *A61K 31/7042* (2013.01); *A61K 35/15* (2013.01); *A61K 47/46* (2013.01); *A61P 35/00* (2018.01); *A61K 9/0019* (2013.01)

(58) Field of Classification Search
CPC ........ A61P 35/00; A61K 35/16; A61K 9/0019
See application file for complete search history.

(56) References Cited

U.S. PATENT DOCUMENTS

| | | |
|---|---|---|
| 2,978,453 A | 4/1961 | Milton |
| 3,845,770 A | 11/1974 | Theeuwes et al. |
| 3,916,899 A | 11/1975 | Theeuwes et al. |
| 4,584,130 A | 4/1986 | Bucci et al. |
| 4,765,539 A | 8/1988 | Noakes et al. |
| 5,112,598 A | 5/1992 | Biesalski |
| 5,336,784 A | 8/1994 | Hiskey et al. |
| 5,521,203 A | 5/1996 | Adams et al. |
| 5,556,611 A | 9/1996 | Biesalski |
| 5,579,458 A | 11/1996 | Yokosuka et al. |
| 5,580,988 A | 12/1996 | Dave |
| 5,607,830 A * | 3/1997 | Biesel ............... A61M 1/3693 210/782 |
| 5,679,777 A | 10/1997 | Anderson et al. |
| 5,693,794 A | 12/1997 | Nielsen |
| 5,698,155 A | 12/1997 | Grosswald et al. |
| 5,950,619 A | 9/1999 | van der Linden et al. |
| 5,954,047 A | 9/1999 | Armer et al. |
| 5,970,974 A | 10/1999 | Van Der Linden et al. |
| 6,133,320 A | 10/2000 | Yallampalli et al. |

(Continued)

FOREIGN PATENT DOCUMENTS

| | | |
|---|---|---|
| CN | 200946766 Y * | 9/2007 |
| CN | 101708337 B | 8/2011 |

(Continued)

OTHER PUBLICATIONS

Dorman, Fulminant babesiosis treated with clindamycin, quinine, and whole-blood exchange transfusion. Transfusion, (Mar. 2000) vol. 40, No. 3, pp. 375-380. (Year: 2000).*
Rafikova et al., Control of Plasma Nitric Oxide Bioactivity by Perfluorocarbons Physiological Mechanisms and Clinical Implications. Circulation. 2004;110:3573-3580 (Year: 2004).*
Akhavan (2004). "Explosives and Propellants," Kirk-Othmer Encyclopedia of Chemical Technology, pp. 719-744.
Aiderman, (1984). "A Review of Cellulose Ethers in Hydrophilic Matrices for Oral Controlled-Release Dosage Forms," Int. J. Pharm. Tech. & Prod. Mfr., 5(3):1-9.
Archibald et al., (1990). "Synthesis and x-ray crystal structure of 1,3,3-trinitroazetidine," J. Org. Chem., 55:2920-2924.

(Continued)

*Primary Examiner* — Qiuwen Mi
(74) *Attorney, Agent, or Firm* — MORRISON & FOERSTER LLP

(57) ABSTRACT

The invention provides compositions and methods for administering a therapeutic agent to a patient, such as pharmaceutical compositions containing a blood product and a therapeutic agent selected from an anthracycline anti-cancer agent (e.g., doxorubicin), a topoisomerase inhibitor, an oxazaphosphinanyl anti-cancer agent, a nitroaryl anti-cancer agent, a thiol-reactive functional group agent, a nitric oxide modulator, a platinum-based antineoplastic compound, acrylamide, acrylonitrile, bis(4-fluorobenzyl)trisulfide, a cardiac glycoside, an anti-mitotic agent (e.g., paclitaxel), a nucleoside analog, an EGFR inhibitor, or an anti-microbial agent.

21 Claims, 13 Drawing Sheets

(56) References Cited

U.S. PATENT DOCUMENTS

| | | | |
|---|---|---|---|
| 6,245,799 | B1 | 6/2001 | Asselin et al. |
| 6,391,911 | B1 | 5/2002 | Bases |
| 6,407,236 | B1 | 6/2002 | Baraldi et al. |
| 7,163,958 | B2 | 1/2007 | Earl et al. |
| 7,507,842 | B2 | 3/2009 | Knox et al. |
| 7,745,643 | B2 | 6/2010 | Cannizzo et al. |
| 8,178,698 | B2 | 5/2012 | Cannizzo et al. |
| 8,299,053 | B2 | 10/2012 | Bednarski et al. |
| 8,664,247 | B2 | 3/2014 | Scicinski et al. |
| 8,927,527 | B2 | 1/2015 | Bednarski et al. |
| 8,946,167 | B2 | 2/2015 | Hegedus et al. |
| 9,139,519 | B2 | 9/2015 | Scicinski et al. |
| 9,226,915 | B2 | 1/2016 | Bednarski et al. |
| 9,468,625 | B2 | 10/2016 | Scicinski et al. |
| 9,987,270 | B1 | 6/2018 | Oronsky et al. |
| 10,149,832 | B2 | 12/2018 | Bednarski et al. |
| 10,342,778 | B1 | 7/2019 | Oronsky et al. |
| 10,543,208 | B2 | 1/2020 | Oronsky et al. |
| 11,008,287 | B2 | 5/2021 | Oronsky et al. |
| 11,160,784 | B1 | 11/2021 | Oronsky et al. |
| 11,510,901 | B2 | 11/2022 | Oronsky et al. |
| 11,576,895 | B2 | 2/2023 | Oronsky et al. |
| 2002/0137770 | A1 | 9/2002 | Nara et al. |
| 2003/0092684 | A1 | 5/2003 | Fredekinq et al. |
| 2004/0024057 | A1 | 2/2004 | Earl et al. |
| 2004/0167212 | A1 | 8/2004 | Bednarski et al. |
| 2005/0070872 | A1* | 3/2005 | Sato ............. A61M 1/0209 604/408 |
| 2006/0111272 | A1 | 5/2006 | Roberts et al. |
| 2006/0211639 | A1 | 9/2006 | Bratzler et al. |
| 2007/0135384 | A1 | 6/2007 | Bednarski et al. |
| 2008/0255149 | A1 | 10/2008 | Dobler et al. |
| 2008/0256149 | A1 | 10/2008 | Bansal et al. |
| 2009/0093644 | A1 | 4/2009 | Cannizzo et al. |
| 2009/0163466 | A1 | 6/2009 | Bednarski et al. |
| 2009/0192085 | A1 | 7/2009 | Robson et al. |
| 2010/0247682 | A1 | 9/2010 | Gladwin et al. |
| 2010/0260719 | A1 | 10/2010 | Zeldis |
| 2011/0130572 | A1 | 6/2011 | Cannizzo et al. |
| 2011/0195947 | A1 | 8/2011 | Straessler et al. |
| 2012/0149678 | A1 | 6/2012 | Oronsky et al. |
| 2013/0053418 | A1 | 2/2013 | Scicinski et al. |
| 2013/0123216 | A1 | 5/2013 | Bednarski et al. |
| 2014/0220163 | A1* | 8/2014 | Soleimani Babadi . A61K 36/28 424/733 |
| 2014/0308260 | A1 | 10/2014 | Oronsky et al. |
| 2014/0349988 | A1 | 11/2014 | Scicinski et al. |
| 2015/0190465 | A1* | 7/2015 | Faivre ............. A61K 31/704 514/17.7 |
| 2015/0246020 | A1 | 9/2015 | Bednarski et al. |
| 2016/0081981 | A1 | 3/2016 | Scicinski et al. |
| 2016/0199346 | A1 | 7/2016 | Bednarski et al. |
| 2018/0085346 | A1 | 3/2018 | Bednarski et al. |
| 2019/0125742 | A1 | 5/2019 | Oronsky et al. |
| 2019/0307723 | A1 | 10/2019 | Oronsky et al. |
| 2020/0022952 | A1 | 1/2020 | Oronsky et al. |
| 2020/0046682 | A1 | 2/2020 | Bednarski et al. |
| 2020/0157047 | A1 | 5/2020 | Oronsky et al. |
| 2020/0345689 | A1 | 11/2020 | Oronsky et al. |
| 2020/0345690 | A1 | 11/2020 | Oronsky et al. |
| 2020/0375982 | A1 | 12/2020 | Oronsky et al. |
| 2021/0178050 | A1 | 6/2021 | Oronsky et al. |
| 2021/0244870 | A1 | 8/2021 | Oronsky et al. |
| 2022/0016077 | A1 | 1/2022 | Bednarski et al. |
| 2022/0054480 | A1 | 2/2022 | Oronsky et al. |

FOREIGN PATENT DOCUMENTS

| | | | |
|---|---|---|---|
| DE | 10111049 | A1 | 9/2002 |
| EP | 412211 | A1 | 2/1991 |
| JP | 48030376 | B * | 9/1973 |
| JP | S5511509 | A | 1/1980 |
| JP | H05155847 | A | 6/1993 |
| JP | 2001507362 | A | 6/2001 |
| JP | 2001506974 | A | 5/2011 |
| JP | 2012523414 | A | 10/2012 |
| JP | 2014530811 | A | 11/2014 |
| JP | 2017506260 | A | 3/2017 |
| RU | 2265440 | C2 | 12/2005 |
| RU | 2411953 | C1 | 2/2011 |
| WO | WO-1995032715 | A1 | 12/1995 |
| WO | WO-1996036602 | A1 | 11/1996 |
| WO | WO-1998016485 | A1 | 4/1998 |
| WO | WO-1998016502 | A1 | 4/1998 |
| WO | WO-1999016436 | A1 | 4/1999 |
| WO | WO-1999059575 | A1 | 11/1999 |
| WO | WO-2000006143 | A1 | 2/2000 |
| WO | WO-2001077100 | A2 | 10/2001 |
| WO | WO-2004032864 | A2 | 4/2004 |
| WO | WO-2004098538 | A2 | 11/2004 |
| WO | WO-2004113281 | A1 | 12/2004 |
| WO | WO-2005046661 | A2 | 5/2005 |
| WO | WO-2006102760 | A1 | 10/2006 |
| WO | WO-2007022121 | A2 | 2/2007 |
| WO | WO-2007022225 | A2 | 2/2007 |
| WO | WO-2007042647 | A1 | 4/2007 |
| WO | WO-2012078992 | A1 | 6/2012 |
| WO | WO-2013052164 | A1 | 4/2013 |
| WO | WO-2013052803 | A2 * | 4/2013 ........... A01N 1/0226 |
| WO | WO-2017123593 | A1 | 7/2017 |

OTHER PUBLICATIONS

Armstrong et al., (2002). "Role of Glutathione Depletion and Reactive Oxygen Species Generation in Apoptotic Signaling in a Human B Lymphoma Cell Line, Cell Death and Differentiation," Nature, 9:252-263.

Australian Examination Report received for Australian patent application No. 2006279589, dated May 18, 2012, 3 pages.

Bamba et al., (1979). "Release Mechanisms in Gelforming Sustained Release Preparations," Int. J. Pharm., 2:307-315.

Berge et al., (1997). "Pharmaceutical Salts," Journal of Pharmaceutical Sciences, 66(1):1-19.

Brezezniak et al., (2016). "RRx-001-Induced Tumor Necrosis and Immune Cell Infiltration in an EGFR Mutation-Positive NSCLC with Resistance to EGFR Tyrosine Kinase Inhibitors: A Case Report," Case Rep Oncol., 9:45-50.

Brown et al., (1998). "Tirapazamine: Laboratory Data Relevant to Clinical Activity," Anti-Cancer Drug Design, 13:529-539. Abstract Only.

Cabrales et al., (2016). "A look inside the mechanistic black box: Are red blood cells the critical effectors of RRx-001 cytotoxicity?" Medical Oncology, 33(7):63, 7 Pages. Abstract Only.

Carter et al., (2016). "Partial response to carboplatin in an RRx-001 pretreated patient with EGFR-inhibitor-resistance and T790M-negative NSCLC," Respir. Aged Case Rep., 18:62-65.

Chawla et al., (2004). "Challenges in Polymorphism of Pharmaceuticals," CRIPS, 5(1):12-15.

Clinicaltrials.gov, (2015). "NCT02489903: An Open-label, Three Stage, Three Arm Pilot Study of RRx-001 For Second Line or Greater Small Cell Lung Cancer, Third Line or Greater Non-Small Lung Cancer, and Second Line or Greater High Grade Neuroendocrine Tumors Prior to Re-administration of Platinum Based Doublet Regimens (Triple Threat)", Available from the Internet, <https://clinicaltrials.gov/ct2/history/NCT024899037V_1=View#StudyPageTop>, 12 pages.

Clinicaltrials.gov, (2015). "NCT01359982: Safety and Pharmacokinetic Study of RRx-001 in Cancer Subjects (Dinamic)," available online at <https://clinicaltrials.gov/ct2/show/NCT02096354?term=RRx-001&draw=1&rank=11>, 7 pages.

Clinicaltrials.gov, (2016). "NCT02096341: A Phase 1 Pilot Study of the Subcutaneous (s.c.) Route to Facilitate the Administration of RRx-001," available online at <https://clinicaltrials.gov/ct2/show/NCT02096341?term=RRx-001&draw=1&rank=3>, 5 pages.

Clinicaltrials.gov, (2018). "NCT03515538: Safety and Efficacy of RRx-001 in the Attenuation of Oral Mucositis in Patients Receiving

(56) References Cited

OTHER PUBLICATIONS

Chemoradiation for the Treatment of Oral Cancers (Prevlar)," retrieved from the internet <https://clinicaltrials.gov/ct2/show/NCT03515538>, 11 pages.

Clinicaltrials.gov, (2019). "NCT02489903: RRX-001 in Lung Cancer, Ovarian Cancer and Neuroendocrine Tumors Prior to Re-administration of Platinum Based Doublet Regimens (Quadruple Threat)", available online at <https://clinicaltrials.gov/ct2/history/NCT02489903?V_1=View#StudyPageTop>, 10 pages.

Clinicaltrials.gov, (2019). "NCT02452970: RRx-001 in Second Line Treatment of Advanced Cholangiocarcinoma Prior to Readministration of First-Line Therapy (EPIC)," available online at <https://clinicaltrials.gov/ct2/show/NCT02452970?term=RRx-001&draw=3&rank=1>, 6 pages.

Clinicaltrials.gov, (2019). "NCT02518958: A Phase I, Open-Label, Multiple Ascending Dose Study of RRx-001 and Nivolumab (Primetime)," available online at <https://clinicaltrials.gov/ct2/show/NCT02518958?term=RRx-001&draw=1&rank=7>, 6 pages.

Clinicaltrials.gov, (2020). NCT02871843: Phase 1 Two Part Dose Escalation Trial of RRx-001 + Radiation + Temozolomide and RRx-001 + Temozolomide Post-RT In Newly Diagnosed Glioblastoma and Anaplastic Gliomas (G-FORCE-1), available online at <https://clinicaltrials.gov/ct2/show/NCT02871843>, 8 pages.

Clinicaltrials.gov, (2021). "NCT02215512: Dose-Escalation Study of RRx-001 in Combination With Whole Brain Radiation in Subjects With Brain Metastases (Brainstorm)," available online at <https://clinicaltrials.gov/ct2/show/NCT02215512>, 7 pages.

Clinicaltrials.gov, (2021). "NCT03699956: RRx-001 Sequentially With a Platinum Doublet or a Platinum Doublet in Third-Line or Beyond in Patients With Small Cell Lung Cancer (Replatinum)," available online at <https://clinicaltrials.gov/ct2/show/NCT03699956?term=RRx-001&draw=1&rank=5>, 8 pages.

Clinicaltrials.gov, (2022). "NCT02096354: A Phase 2 Randomized, Open-Label Study of RRx-001 vs Regorafenib in Subjects With Metastatic Colorectal Cancer (Rocket)," available online at <https://clinicaltrials.gov/ct2/show/NCT02096354?term=RRx-001&draw=1&rank=8>, 8 pages.

Clinicaltrials.gov, (2022). "NCT02801097: RRx-001 in Combination With Irinotecan in Metastatic or Advanced Cancer (Payload) (Payload)," available online at <https://clinicaltrials.gov/ct2/show/NCT02801097?term=RRx-001&draw=1&rank=6>, 6 pages.

Clinicaltrials.gov, (2022). "NCT02871843: RRx-001 + Radiation + Temozolomide In Newly Diagnosed Glioblastoma and Anaplastic Gliomas (G-FORCE-1)," available online at <https://clinicaltrials.gov/ct2/show/NCT02096354?term=RRx-001&draw=1&rank=9>, 8 pages.

Clinicaltrials.gov, (2022). "NCT04525014: RRx-001 Given With Irinotecan and Temozolomide for Pediatric Patients With Recurrent or Progressive Malignant Solid and Central Nervous System Tumors (Pirate)," available online at <https://clinicaltrials.gov/ct2/show/NCT02096341?term=RRx-001&draw=1&rank=3>, 10 pages.

Coburn et al., (1998). caplus an 1998:567551, RN 179894-08-7, 1 page.

Crowder et al., (1999). "Vibrational analysis of high-energy compounds: 1,3,3-trinitroazetidine and 1-acetvl-3, 3-dinitroazetidine," Journal of Energetic Materials, 17(1):49-68.

Crowder et al., (1999). caplus an 1999:171384, RN 179894-08-7,1 page.

Dave et al., (2000). "Convenient Acylative Dealkylation of Tertiary Amines," Journal of Organic Chemistry, 65:1207-1209.

Dave, (1996). "Acylative Dealkylation of N-tert-Butyl-3-substituted Azetidines: Facile Access to [1.1.0] Azabicyclobutane, 3-Hydroxyazetidinium Hydrochloride, and 3-Azetidinones," J. Org. Chem., 61:5453-5455.

Dave, (1997), caplus an 1997:67373, RN 179894-08-7,1 page.

Drumond et al., (2013). "Transmissible Venereal Tumor treated with Autohemotherapy," Acta Scientiae Veterinariae, 41:1107, 4 pages.

During et al., (1989). "Controlled Release of Dopamine from a Polymeric Brain Implant: In Vivo Characterization," Annals of Neurology, 25(4):351-356. Abstract Only.

European Supplementary Search Report for European Patent Application No. EP12839088.7, published Apr. 28, 2015, 4 pages.

Fareed et al., (2000). "An update on herapins at the beginning of the new millennium," Semin Thromb Hemost., 26(Suppl 1):5-21.

Feuer et al., (1954). "The Mannich reaction of certain dinitro alcohols with glycine and ethanolamine," Journal of American Chemical Society, 76:5124-5126.

Final Office Action received for U.S. Appl. No. 13/655,618 dated Jun. 12, 2014, 6 pages.

Final Office Action received for U.S. Appl. No. 13/655,618 dated Sep. 11, 2013, 4 pages.

Final Office Action received for U.S. Appl. No. 14/965,062 dated Feb. 6, 2017, 6 pages.

Final Office Action received for U.S. Appl. No. 16/284,035 dated May 26, 2022, 28 pages.

Final Office Action received for U.S. Appl. No. 16/284,035 dated Nov. 15, 2021, 24 pages.

Fitch et al., (2013). "Abstract WRM 267: High resolution MS proves that the developmental cancer drug, RRx-001, alkylates the hemoglobin beta chain," 44th Western Regional Meeting of the American Chemical Society, available online at <http://www.acswrm.org/wrm2013/files/Abstracts_SaturdayAM.pdf>, 1 page.

Garver et al., (1984). "Catalyzed Oxidative Nitration of Nitronate Salts," J. Org. Chem. 50(10):1699-1702.

Gladwin et al., (2005). "The Emerging Biology of the Nitrite Anion," in Nature Chemistry and Biology, 1:308-31.

Goodson, (1984). "Dental Applications," Chapter 6 of Medical Applications of Controlled Release, 2:115-138.

Granelli et al., (2004). "SEL 1 Land Squamous Cell Carcinoma of the Esophagus," Clinical Cancer Research, 10:5857-5861.

Grisham, (2017). "Pumped Up: Implanted Chemotherapy Device Improves Survival when Colorectal Cancer Spreads to the Liver," available online at <https://www.mskcc.org/news/pumped-implanted-chemotherapy-device-improves-survival-when-colorectal-cancer-spreads-liver>, 5 pages.

Heller, (2010). "An Electrochemical Engineering Perspective of Nitric Oxide in Tumors: Why the Combination of an Allosteric Effector of Hemoglobin with Dietary Sodium Nitrite Should Be Effective in Treating Vascularized Tumors?," ECS Transactions, 28(33):1-6.

Hiskey et al., (1993). caplus an 1993:233785, RN 147636-85-9, 1 page.

Hiskey et al., (1994). caplus an 1994:700750, RN 158669-97-7, 1 page.

Hiskey et al., (1999). "Preparation of 1-Substituted-3,3-Dinitroazetidines," Journal of Energetic Materials, 17:233-254.

Hiskey et al., (1999). caplus an 1999:411860, RN 236102-58-2, 1 page.

Hockel et al., (2001). "Tumor Hypoxia: Definitions and Current Clinical, Biologic, and Molecular Aspects," Journal of the National Cancer Institute, 93(4):266-276.

Hong et al., (2008). Combining Targeted Therapies, Targeted Cancer Therapy, p. 362, 2 pages.

Howard et al., (1989). "Intracerebral Drug Delivery in Rats with Lesion-Induced Memory Deficits," J. Neurosurg., 71:105-112.

Huguenin et al., (2005). "Evaluation of the antitumoral potential of different nitric oxide-donating non-steroidal anti-inflammatory drugs (NO-NSAIDs) on human urological tumor cell lines," Cancer Letters, 218:163-170.

Ignarro, (2000). "Nitric Oxide Biology and Pathology," Academic Press, pp. 5, 895, and 908.

International Preliminary Report on Patentability for PCT/US2019/012696 dated Jul. 14, 2020, 8 pages.

International Preliminary Report on Patentability for PCT/US2019/012701 dated Jul. 14, 2020, 8 pages.

International Search Report and Written Opinion for PCT/US2011/064178 dated Apr. 17, 2012, 8 pages.

International Search Report and Written Opinion for PCT/US2012/038592 dated Aug. 10, 2012, 11 pages.

International Search Report and Written Opinion for PCT/US2012/058964, dated Apr. 5, 2013, 9 pages.

International Search Report and Written Opinion for PCT/US2017/012948 dated Mar. 28, 2017, 8 pages.

(56) References Cited

OTHER PUBLICATIONS

International Search Report and Written Opinion for PCT/US2017/056454 dated Feb. 6, 2018, 12 pages.
International Search Report and Written Opinion for PCT/US2018/041138 dated Oct. 5, 2018, 9 pages.
International Search Report and Written Opinion for PCT/US2019/012696 dated Sep. 6, 2019, 12 pages.
International Search Report and Written Opinion for PCT/US2019/012701 dated Sep. 4, 2019, 12 pages.
International Search Report for PCT/US2006/031722 dated May 29, 2007, 1 page.
International Search Report for PCT/US2006/031917 dated Jul. 20, 2007, 1 page.
International Search Report for PCT/US2011/021500 dated May 3, 2011, 4 pages.
Jia et al., (2002). "No donors with anticancer activity," Expert Opin. Therapeut., 12(6):819-826.
Jia, (2008). "A Guide to Pass the National Licensed Pharmacist Examination in Medicinal Chemistry," pp. 4-11, 9 pages. English Abstract.
Johnson et al., (2001). "Relationships Between Drug Activity in NCI Preclinical in Vitro and in Vivo Models and Early Clinical Trials," British J. Cancer, 84(10):1424-1431.
Kamran et al., (2016). "Radioprotective Agents: Strategies and Translational Advances," Medicinal Research Reviews, 36(3):461-493, 33 pages.
Kashfi et al., (2002). "Nitric Oxide-Donating Nonsteroidal Anti-Inflammatory Drugs Inhibit the Growth of Various Cultured Human Cancel Cells: Evidence of a Tissue Type-Independent Effect," J. Pharmacology Experimental Therapeutics, 303(3):1273-1282.
Katritzky et al., (1994). "Novel Syntheses of 1,3,3-Trinitroazetidine," J. Heterocyclic Chem., 31:271-275.
Kim et al., (2016). "Whole Brain Radiotherapy and RRx-001: Two Partial Responses in Radioresistant Melanoma Brain Metastases from a Phase 1/11 Clinical Trial: A TITE-CRM Phase 1/11 Clinical Trial," Translational Oncology, 9(2):108-113.
Konovalova et al., (2003). "Nitric oxide donor increases the efficiency of cytostatic therapy and retards the development of drug resistance," Nitric Oxide, 8(1):59-64.
Kornblum et al., (1983). "Oxidative Substitution of Nitroparaffin Salts," J. Org. Chem., 48:332-337.
Langer et al., (1983). "Chemical and Physical Structure of Polymers as Carriers for Controlled Release of Bioactive Agents: A Review," JMS-Rev. Macromol. Chem. Phys., pp. 61-126.
Langer et al., (1984). "Chapter 2: Medical Applications of Controlled Release," Classes of Systems, pp. 42-67.
Langer, (1990). "New Methods of Drug Delivery," Science, 249(4976):1527-1533.
Levy et al., (1985). "Inhibition of Calcification of Bioprosthetic Heart Valves by Local Controlled-Release Diphosphonate," Science, 228(4696):190-192.
Li et al., (2006). caplus an 2006:150006, RN 179894-08-7, 1 page.
Li, (2014). "Nursing Comprehensive Skills Training," China Press of Traditional Chinese Medicine, 3 pages. English abstract.
Ling et al., (2005). "Phase I study of CM—Na combined with concurrent radiochemotherapy for advanced esophageal carcinoma," Chinese Journal of Cancer, 24(5):582-6. Abstract Only.
Lopez-Ferrer et al., (2002). "Differences in the O-Glycosylation Patterns Between Lung Squamous Cell Carcinoma and Adenocarcinoma," Am. J. Clin. Pathol., 118:749-755.
Lusk et al., (2004). "Electrochemical Oxidation of Alkylnitro Compounds PP-1345, A SERDP 'Seed' Activity," available online at <https://www.serdp-estcp.org/content/download/6439/85721/file/PP-1345-FR-01.pdf>, 30 pages.
Marchand et al., (1994). "Additions of X-Y Across the C(3)-N a-Bond in 1-Aza-3-ethylbicyclo[1.1.0]butane, Novel Routes to 3-Substituted Azetidines," Journal of Organic Chemistry, 59(18):5499-5501.
Marchand et al., (1995). "A Novel Approach to the Synthesis of 1,3,3-Trinitroazetidine," J. Org Chem., 60(15):4943-4946.

Maxwell et al., (1997). "Hypoxia-inducible factor-1 modulates gene expression in solid tumors and influences both angiogenesis and tumor growth," Proc. Natl. Acad. Sci. USA, 94:8104-8109.
McKenney et al., (1998). "Synthesis and thermal properties of 1,3-dinitro-3-(1', 3'-dinitroazetidin-3'-yl) azetidine (TNDAZ) and its admixtures with 1,3,3-trinitroazetidine (TNAZ)," Journal of Energetic Materials, 16:199-235.
Mendenhall et al., (2000). "Radiation Therapy for Squamous Cell Carcinoma of the Tonsillar Region: A Preferred Alternative to Surgery?" J. Clinical Oncology, 18(11):2219-2225.
Merck & Co., Inc., (2008). "TEMODAR Prescribing Information," 17 pages.
Miller et al., (2015). "CD47 Receptor Globally Regulates Metabolic Pathways That Control Resistance to Ionizing Radiation," J. Biol. Chem., 290:24858-24874.
Morales-Suarez-Varela et al., (1995). "Impact of Nitrates in Drinking Water on Cancer Mortality in Valencia, Spain," European Journal of Epidemiology, 11:15-21.
Muehlstaedt et al., (1975). caplus an 1976:89768, RN 58373-43-6, 1 page.
Nabi et al., (2001). "Primary squamous cell carcinoma of the prostate: a rare clinicopathological entity. Report of 2 cases and review of literature," Ural. Int., 66(4):216-219. Abstract Only.
Naimi et al., (2003). "Synthesis of 3'- and 5'-Nitrooxy Pyrimidine Nucleoside Nitrate Esters: "Nitric Oxide Donor" Agents for Evaluation as Anticancer and Antiviral Agents," J. Med. Chem., 46:995-1004.
Nara et al., (2002). caplus an 2002:169585, RN 402835-09-0, 1 page.
Newman et al., (2003). "Solid-state analysis of the active pharmaceutical ingredient in drug products," Drug Discovery Today, 8(19):898-905.
Nih, (2018). "Vascular Tumor," available online at <https://www.cancer.gov/gublications/dictionaries/cancer-terms/def/vascular-tumor>, 1 page.
Ning et al., (2002). "The Antiangiogenic Agents SU5416 and SU6668 Increase the Antitumor Effects of Fractionated Irradiation," Radiation Research, 157:5-51.
Ning et al., (2012). "Dinitroazetidines Are a Novel class of Anticancer Agents and Hypoxia-Activated Radiation Sensitizers Developed from Highly Energetic Materials," Cancer Res., 72:2600-2608.
Ning et al., (2015). "Nrf2 activity as a potential biomarker for the pan-epigenetic anticancer agent, RRx-001," Oncotarget, 6(25):21547-21556.
Nitrates and Nitrites Answers to Frequently Asked Questions, Ohio Bureau of Environmental Health, Health Assessment Section, Nov. 1, 2006, 2 pages.
Oberoi et al., (2013). "Nanocarriers for delivery of platinum anticancer drugs," Advanced Drug Delivery Reviews, 65(13):1667-1685.
Office Action received for U.S. Appl. No. 12/397,651 dated Feb. 11, 2011, 10 pages.
Office Action received for U.S. Appl. No. 12/397,651 dated Feb. 23, 2012, 8 pages.
Office Action received for U.S. Appl. No. 13/655,618 dated Feb. 25, 2014, 6 pages.
Office Action received for U.S. Appl. No. 13/655,618 dated May 2, 2013, 9 pages.
Office Action received for U.S. Appl. No. 14/849,783 dated Jan. 15, 2016, 5 pages.
Office Action received for U.S. Appl. No. 14/965,062 dated Aug. 11, 2016, 10 pages.
Office Action received for U.S. Appl. No. 14/965,062 dated Dec. 18, 2017, 8 pages.
Office Action received for U.S. Appl. No. 15/298,735 dated Aug. 30, 2018, 9 pages.
Office Action received for U.S. Appl. No. 15/669,403 dated Sep. 14, 2018, 9 pages.
Office Action received for U.S. Appl. No. 15/989,862 dated Feb. 8, 2019, 6 pages.
Office Action received for U.S. Appl. No. 16/284,035 dated Apr. 13, 2021, 17 pages.

(56) References Cited

OTHER PUBLICATIONS

Office Action received for U.S. Appl. No. 16/353,047 dated Aug. 31, 2020, 7 pages.
Office Action received for U.S. Appl. No. 16/712,148 dated Oct. 7, 2020, 7 pages.
Office Action received for U.S. Appl. No. 16/960,443 dated May 28, 2021, 25 pages.
Oronsky et al., (2015). "A Review of Two Promising Radiosensitizers in Brain Metastases: Rrx-001 and 2-Deoxyqlucose," J. Cancer Sci. Ther., 7:137-141.
Oronsky et al., (2016). "RRx-001, A novel dinitroazetidine radiosensitizer," Invest. New Drugs, 34(3):371-377.
Oronsky et al., (2017). "RRx-001: a systemically non-toxic M2-to-M1 macrophage stimulating and prosensitizing agent in Phase II clinical trials", Expert Opinion on investigational Drugs, 26(1):109-119.
Oxley et al., (1997). "Thermal Decomposition Pathways of 1,3,3-Trinitroazetidine (TNAZ), Related 3,3-Dinitroazetidium Salts, and 15N, 13C, and 2H Isotopomers," Journal of Physical Chemistry A, 101(24):4375-4383.
Padwa et al., (1985). "Diastereofacial selectivity in azomethine ylide cycloaddition reactions derived from chiral α-cyanoaminosilanes," Tetrahedron, 41(17):3529-3535.
Peiris et al., (2001). "Structures of dinitroazetidine and three of its carbonyl derivatives," Journal of Chemical Crystallography, 30(10):647-653.
Pinkel, (1958). "The use of body surface area as a criterion of drug dosage in cancer chemotherapy," Cancer Research, 18:853-856.
Prezioso et al., (1994). "Genetic Toxicity Evaluation of 1, 3, 3-Trinitroazetidine, vol. IV: Summary Report on the Genotoxicity of TNAZ," AL/OE-TR-1994-0069 vol. IV of IV, Air Force Materiel Command, Wriqht-Patterson Air Force Base, Ohio, 22 pages.
Raleigh et al., (1999). "P269: Pharmacokinetics of Isotretinoin (ISO) in Rats Following Oral Dosing or Aerosol Inhalation," British J. Cancer, 80(suppl 2):96.
Reid et al., (2014). "Two Case Reports of Resensitization to Previous Chemotherapy with the Novel Hypoxia-Activated Hypomethylating Anticancer Agent RRx-001 in Metastatic Colorectal Cancer Patients," Case Rep. Oncol., 7(1):79-85.
Reid et al., (2015). "Safety and activity of RRx-001 in patients with advanced cancer: a first-in-human, open-label, dose-escalation phase 1 study," Lancet Oncol, 16:1133-42.
Remington, (1995). "The Science and Practice of Pharmacy," 19th Edition, vol. II, pp. 1495-1562, 1577-1614, and 1660-1692.
Rosenthal, (1999). "A Phase I Single-Dose Trial of Gadolinium Texaphyrin (Gd-Tex), a Tumor Selective Radiation Sensitizer Detectable by Magnetic Resonance Imaging," Clinical Cancer Research, 5(4):739-745.
Rupnow et al., (1998). "p53 Mediates Apoptosis Induced by C-Myc Activation in Hypoxic or Gamma Irradiated Fibroblasts," Cell Death and Differentiation, 7:141-147.
Sandler, (1961). "Clinical evaluation of propatylnitrate in angina pectoris," British Medical Journal, 2(5269):1741-1744.
Sauder, (1989). "A Preliminary Trial of the Programmable Implantable Medication System for Insulin Delivery," The New England Journal of Medicine, 321(9):574-579.
Sausville et al., (2006). "Contributions of Human Tumor Xenografts to Anticancer Development," Cancer Research, 66(7):3351-3354.
Schwartz (2007). "Anemia in patients with cancer: incidence, causes, impact, management, and use of treatment guidelines and protocols," Am. J. Health-Syst. Pharm., 64(3 Supplement 2):S5-S13.
Scicinski et al., (2012). "Preclinical Evaluation of the Metabolism and Disposition of RRx-001, a Novel Investigative Anticancer Agent", Drug Metabolism and Disposition, 40(9):1810-1816.
Scicinski et al., (2014). "Development of methods for the bioanalysis of RRx-001 and metabolites", Bioanalysis, 6(7):947-956.
Scicinski et al., (2015). "No to cancer: The complex and multifaceted role of nitric oxide and the epigenetic nitric oxide donor, RRx-001," Redox Biology, 6:1-8.
Sefton, (1987). "Implantable Pumps," CRC Grit. Rev. Biomed. Eng., 14(3):201-237.
Shokeir, (2004). "Squamous Cell Carcinoma of the Bladder: pathology, diagnosis and treatment," BJU International, 93:216-220.
Sikder et al., (2004). "1,3,3-Trinitroazetidine (TNAZ), a melt-cast explosive: synthesis, characterization and thermal behavior," Journal of Hazardous Materials, 113:35-43.
Simpson et al., (1994). "Characterization of TNAZ," UCRL-ID-119672, Lawrence Livermore National Laboratory, 15 pages.
Smolen et al., (1984). "Chapter 7: Controlled Drug Bioavailability," Drug Product Design and Performance, pp. 203-237.
Stamler et al., (2002). "Inhaled ethyl nitrite gas for persistent pulmonary hypertension in infants," The Lancet, 360(9350):2077.
Straessler et al., (2012). "Development of a Safe and Efficient Two-Step Synthesis for Preparing 1-Bromoacetyl-3,3-dinitroazetidine, a Novel Clinical Anticancer Candidate," Organic Process Research & Development, 16:512-517.
Stratford et al., (1998). "Bioreductive drugs into the next millennium," Anti-Cancer Drug Design, 13:519-528.
Thomas, (2016). "Mucositis in Cancer Patients: A Review," available online at <https://www.uspharmacist.com/article/mucositis-in-cancer-patients-a-review#:~:text=Mucositis%20is%20a%20common%20complication,the%20gastrointestinga%20(GI)%20tract.&text=Although%20mucositis%20can%20occur%20anywhere,site%22is%20the%20oral%20cavity>, 10 pages.
Treat et al., (1989). "Liposome Encapsulated Doxorubicin: Preliminary Results of Phase I and Phase II Trials," Liposomes in the Therapy of Infectious Diseases and Cancer, Proceedings of the Ciba-Geigy-Squibb-UCLA Colloquium, pp. 353-365.
Verma et al., (2000). "Osmotically Controlled Oral Drug Delivery," Drug Dev. Ind. Pharm., 26(7):695-708.
Watt et al., (1998). "TNAZ Based Melt-Cast Explosives: Technology Review and AMRL Research Directions," Weapons Systems Division, Aeronautical and Maritime Research Laboratory, Melbourne, Australia. Report DSTO-TR-0702, 37 pages.
Watt et al., (2000). "Evaluation of 1,3,3-Trinitrozaetidine (TNAZ)—A High Performance Melt-Castable Explosive," Weapons Systems Division, Aeronautical and Maritime Research Laboratory, Melbourne, Australia. Report No. DSTO-TR-1000, 34 pages.
West, (1988). "Solid State Chemistry and its Applications," Wiley, New York, pp. 358 and 365.
Weyerbrock et al., (2003). "Selective opening of the blood-brain barrier by a nitric oxide donor and long-term survival in rats with C6 gliomas," Journal of Neurosurgery, 99(4):728-737.
Wilson et al., (1998). "Radiation-activated prodrugs as hypoxia-selective cytotoxins model studies with nitroarylmethyl quaternary salts," Anti-Cancer Drug Design, 13:663-685.
Wong, (1991). "Chapter 5: Heterobifunctional Cross-Linkers," Chemistry of Protein Conjugation and Crosslinking, p. 147, 3 pages.
Written Opinion of the International Searching Authority for PCT/US2006/031722 dated May 29, 2007, 3 pages.
Written Opinion of the International Searching Authority for PCT/US2006/031917 dated Jul. 20, 2007, 3 pages.
Written Opinion of the International Searching Authority for PCT/US2011/021500 dated Aug. 9, 2012, 4 pages.
Wu et al., (2011). "Reactive impurities in excipients: profiling, identification and mitigation of drug-excipient incompatibility," in AAPS PharmSciTech., 12(4):1248-1263.
Yamaguchi et al., (2000). "Photodynamic Therapy with Motexafin Lutetium (Lu-Tex) Reduces Experimental Graft Coronary Artery Disease," Transplantation, 71(11):1526-1532.
Yarmukhamedov et al., (2005). "One-step synthesis of substituted 3,5-dinitropiperidines and 1,5-dinitro-3,7-diazabicyclo(3.3.1)nonanes from 1,3-dinitropropanes," Russian Chemical Bulletin, International Edition, 54(2):414-420.
Yen et al., (2004). "18F-FDG Uptake in Squamous Cell Carcinoma of the Cervix is Correlated with Glucose Transporter 1 Expression," The Journal of Nuclear Medicine, 45(1):22-29.
You, (2011). "代动力学性质，不但增加了血药浓度，且延长作用时间," Medicinal Chemistry, pp. 585-588, 5 pages. English Abstract.

(56) References Cited

OTHER PUBLICATIONS

Zervoudakis et al., (2017). "Treatment Options in Colorectal Liver Metastases: Hepatic Arterial Infusion," Visc Med, 33:47-53.

Zhang et al., (1998). caplus an 1998:460439, RN 211429-18-4, 1 page.

Zhu et al., (2017). "Amino-functionalized nano-vesicles for enhanced anticancer efficacy and reduced myelotoxicity of carboplatin," Colloids and Surfaces, B, Biointerfaces, 157:56-64.

Zuo, (2015). "Chapter 16: Cell Death," Medical Cell Biology, pp. 230-235, 7 pages. English Abstract.

Achan et al., (2011). "Quinine, an old anti-malarial drug in a modern world: role in the treatment of malaria," Malar J., 10:144, 12 pages.

Anjaria et al., (2008). "Haemorrhagic shock therapy," Expert Opinion Pharmacother, 9(6):901-911. Abstract Only.

Brouse et al., (2015). "Impact of hemoglobin nitrite to nitric oxide reductase on blood transfusion for resuscitation from hemorrhagic shock," Asian Journal of Transfusion Science, 9(1):55-60.

Deutsches Zentrum fur Luft-und Raumfahrt, (2020). "How intense and dangerous is cosmic radiation on the Moon?" available online at <https://www.dlr.de/content/en/articles/news/2020/03/20200925_how-intense-and-dangerous-is-cosmic-radiation-on-the-moon.html>, 3 pages.

Harmon et al., (2011). "Radioactive Omission: Where Are the Anti-Radiation Drugs?" Scientific American, 5 pages.

NASA, (2017). "NASA Protects Its Superheroes From Space Weather," available online at <https://www.nasa.gov/feature/nasa-protects-its-superheroes-from-space-weather>, 3 pages.

National Academies of Sciences, Engineering, and Medicine, (2021). "Consensus Study Report Highlights: Space Radiation and Astronaut Health: Managing and Communicating Cancer Risks," The National Academies Press. 4 pages.

NIH, (2022). "Cancer Causes and Prevention" available online at <https://www.cancer.gov/about-cancer/causes-prevention#:%20-:text=Cancer%20prevention%20is%20action%20taken,can%20prevent%20cancer%20from%20developing>, 1 page.

Office Action received for U.S. Appl. No. 17/223,422 dated Sep. 19, 2022, 7 pages.

Takakura et al., (2006). "Acute onset of ulcerative colitis following an operation for sigmoid colon cancer," J. Gastroenterol., 41:77-82. Abstract Only.

Thorsen et al., (1994). "Administration of drugs by infusion pumps in palliative medicine," Ann Acad Med Singap, 23(2):209-11. Abstract Only.

Zhang et al., (2020). "Quantifying methane emissions from the largest oil-producing basin in the United States from space," Sci. Adv. 6:eaaz5120, 9 pages.

Yonezawa, (2012). "Molecular mechanism underlying delivery of platinum agents to the cancer and kidney," Drug Delivery System, 27(5):381-388.

\* cited by examiner

FIG. 6A
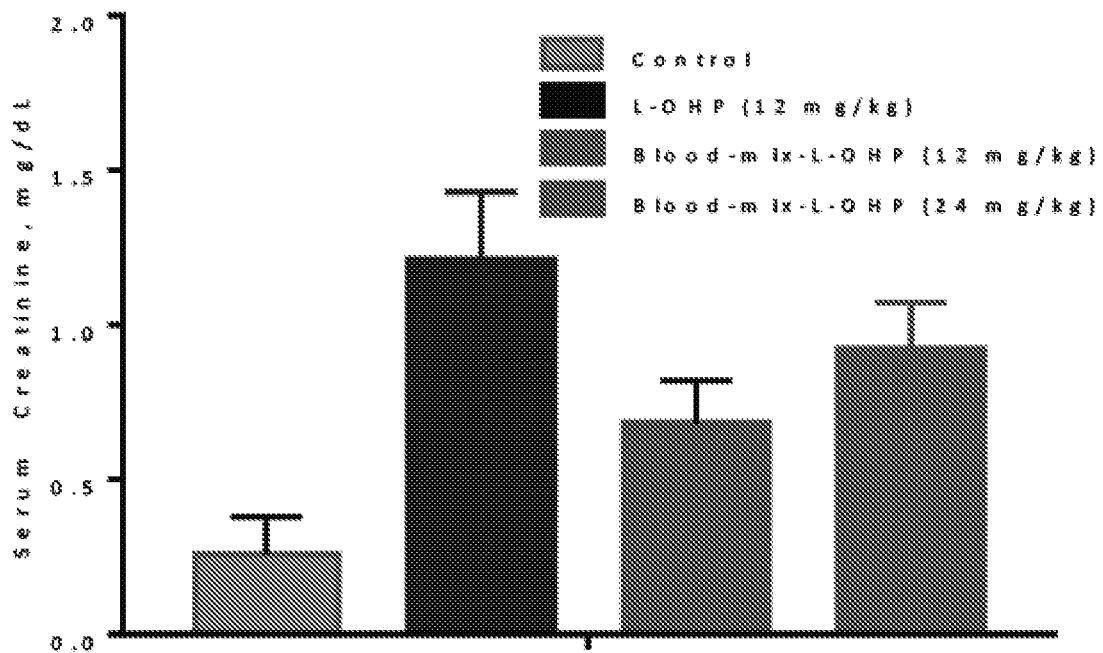
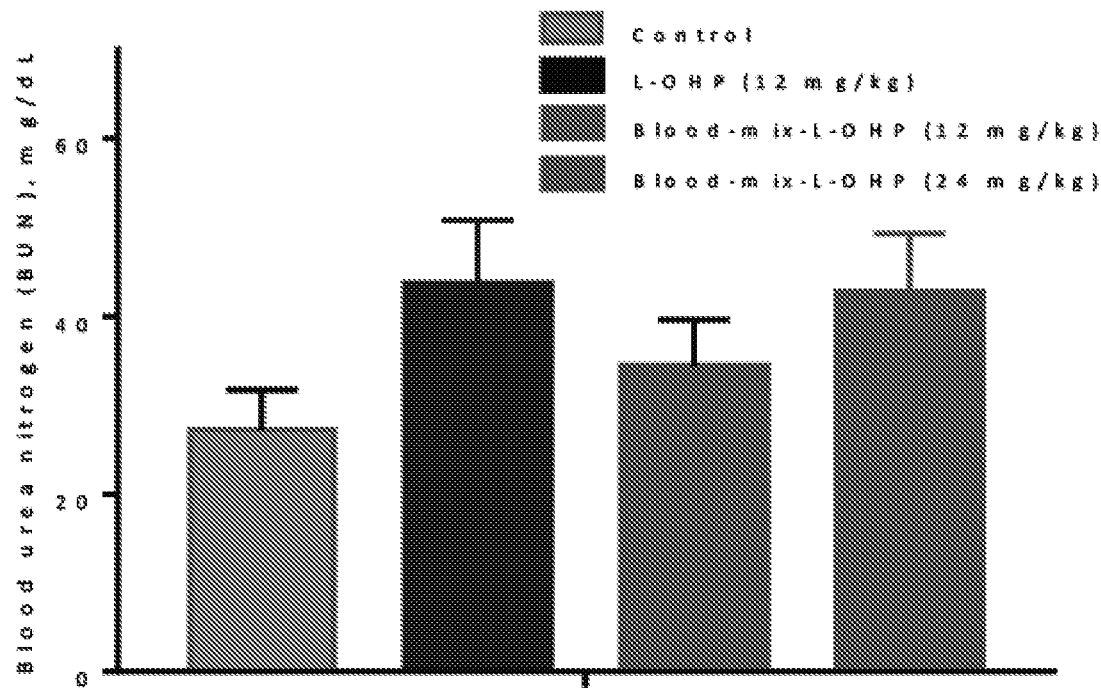
FIG. 6B

COMPOSITIONS AND METHODS FOR PARENTERAL ADMINISTRATION OF THERAPEUTIC AGENTS

CROSS-REFERENCE TO RELATED APPLICATIONS

This application is a U.S. national stage application under 35 U.S.C. § 371 of International Application No. PCT/US2018/041138, filed on Jul. 6, 2018, which claims priority to and the benefit of U.S. Patent Application No. 62/565,808, filed on Sep. 29, 2017; U.S. Patent Application No. 62/549,835, filed on Aug. 24, 2017; U.S. Patent Application No. 62/534,639, filed on Jul. 19, 2017; and U.S. Patent Application No. 62/529,635, filed on Jul. 7, 2017; each of which is incorporated by reference herein in its entirety.

FIELD OF THE INVENTION

The invention provides compositions and methods for administering a therapeutic agent to a patient, such as pharmaceutical compositions containing a blood product and a therapeutic agent such as an anthracycline anti-cancer agent (e.g., doxorubicin), a topoisomerase inhibitor, an oxazaphosphinanyl anti-cancer agent, a nitro-aryl anti-cancer agent, a thiol-reactive functional-group agent, a nitric oxide modulator, a platinum-based antineoplastic compound, acrylamide, acrylonitrile, bis(4-fluorobenzyl)trisulfide, a cardiac glycoside, an anti-mitotic agent (e.g. paclitaxel), a nucleoside analog, an EGFR inhibitor, or an anti-microbial agent.

BACKGROUND

Cancer is a significant health problem despite the many advances made for detecting and treating this disease. Current strategies for managing cancer rely on early diagnosis and aggressive treatment. Treatment options often include surgery, radiotherapy, chemotherapy, hormone therapy, or a combination thereof. While such therapies provide a benefit to many patients, there is still a need for better therapeutic agents to treat various types of cancer.

Prostate cancer, breast cancer, and lung cancer are leading causes of cancer-related death. Prostate cancer is the most common form of cancer among males, with an estimated incidence of 30% in men over the age of 50. Moreover, clinical evidence indicates that human prostate cancer has the propensity to metastasize to bone, and the disease appears to progress inevitably from androgen dependent to androgen refractory status, leading to increased patient mortality. Breast cancer remains a leading cause of death in women. Its cumulative risk is relatively high; certain reports indicate that approximately one in eight women are expected to develop some type of breast cancer by age 85 in the United States. Likewise, lung cancer is a leading cause of cancer-related death, and non-small cell lung cancer (NSCLC) accounts for about 80% of these cases. Attempts to use serum protein markers for the early diagnosis of lung cancer have not yielded satisfactory results for routine screening, and newly developed early diagnostic methods using serum DNA as a diagnostic marker await further validation.

In general, anti-cancer agents and modalities are plagued by side effects and limited responses. These limitations are in turn linked with inadequate circulation half-lives, insufficient tumor uptake of drug, toxicities to normal tissues, and the occurrence of drug-drug interactions, which lead, for example, to sub-optimal dosing regimens or patient non-compliance.

Microbes cause infectious and non-infectious diseases in humans. While anti-microbial agents provide a benefit to many patients, there is still a need for better therapeutic agents to treat various types of diseases and disorders involving infection. Limitations of existing therapies include inadequate circulation half-lives, toxicities to normal tissues, and the occurrence of drug-drug interactions. These limitations can lead, for example, to sub-optimal dosing regimens or patient noncompliance, both of which can contribute to the emergence of anti-microbial resistant microbes.

The present invention provides new formulations containing therapeutic agents that can be administered to a patient, which may be used in cancer therapy, treatment of diseases and disorders involving infection, and other applications as described herein below.

SUMMARY

The invention provides compositions and methods for administering a therapeutic agent to a patient, such as pharmaceutical compositions containing a blood product and a therapeutic agent, such as anthracycline anti-cancer agent (e.g., doxorubicin), a topoisomerase inhibitor, an oxazaphosphinanyl anti-cancer agent, a nitro-aryl anti-cancer agent, a thiol-reactive functional-group agent, a nitric oxide modulator, a platinum-based antineoplastic compound, acrylamide, acrylonitrile, bis(4-fluorobenzyl)trisulfide, a cardiac glycoside, an anti-mitotic agent (e.g. paclitaxel), a nucleoside analog, an EGFR inhibitor, or an anti-microbial agent. One exemplary composition contains whole blood and doxorubicin, which may be administered intravenously to a patient, such as for use in treating cancer in a patient. Another exemplary composition contains whole blood and imipenem, which may be administered intravenously to a patient, such as for use in treating a disease or disorder involving infection in a patient (e.g. sepsis). Ex vivo mixing of a therapeutic agent with a blood product to form a pharmaceutical composition can provide benefits to the patient, such as, in certain instances, improvement in the efficacy of the therapeutic agent and/or reduction of adverse side effects. In various embodiments, the blood product is from or is derived from the patient who is to receive a pharmaceutical composition of the invention. The invention having been generally described is explained in more detail in the aspects and embodiments below and in the detailed description.

Accordingly, one aspect of the invention provides a method for administering a therapeutic agent to a patient. The method comprises parenterally administering to a patient in need thereof a pharmaceutical composition that comprises (i) a blood product and (ii) a therapeutic agent selected from the group consisting of an anthracycline anti-cancer agent, a topoisomerase inhibitor, an oxazaphosphinanyl anti-cancer agent, a nitro-aryl anti-cancer agent, a thiol-reactive functional-group agent, a nitric oxide modulator, a platinum-based antineoplastic compound, acrylamide, acrylonitrile, bis(4-fluorobenzyl)trisulfide, a cardiac glycoside, an anti-mitotic agent, a nucleoside analog, an EGFR inhibitor, and an anti-microbial agent. The blood product may be an erythrocyte cell, or may be whole blood. Desirably, the pharmaceutical composition can be administered by intravenous administration. Exemplary anthracycline anti-cancer agents include doxorubicin and epirubicin.

Another aspect of the invention provides a method for administering a therapeutic agent to a patient. The method comprises parenterally administering to a patient in need thereof a pharmaceutical composition that comprises (i) a blood product and (ii) a therapeutic agent selected from the group consisting of an anthracycline anti-cancer agent, a topoisomerase inhibitor, an oxazaphosphinanyl anti-cancer agent, a nitro-aryl anti-cancer agent, a thiol-reactive functional-group agent, a nitric oxide modulator, a platinum-based antineoplastic compound, acrylamide, acrylonitrile, bis(4-fluorobenzyl)trisulfide, a cardiac glycoside, an anti-mitotic agent, a nucleoside analog, and an anti-microbial agent. The blood product may be an erythrocyte cell, or may be whole blood. Desirably, the pharmaceutical composition can be administered by intravenous administration. Exemplary anthracycline anti-cancer agents include doxorubicin and epirubicin.

Another aspect of the invention provides a method for administering a therapeutic agent to a patient. The method comprises parenterally administering to a patient in need thereof a pharmaceutical composition that comprises (i) a blood product and (ii) a therapeutic agent selected from the group consisting of an anthracycline anti-cancer agent, a topoisomerase inhibitor, an oxazaphosphinanyl anti-cancer agent, a nitro-aryl anti-cancer agent, a thiol-reactive functional-group agent, a nitric oxide modulator, a platinum-based antineoplastic compound, acrylamide, acrylonitrile, bis(4-fluorobenzyl)trisulfide, a cardiac glycoside, an anti-mitotic agent, and an anti-microbial agent. The blood product may be an erythrocyte cell, or may be whole blood. Desirably, the pharmaceutical composition can be administered by intravenous administration. Exemplary anthracycline anti-cancer agents include doxorubicin and epirubicin.

Another aspect of the invention provides a method for administering a therapeutic agent to a patient. The method comprises parenterally administering to a patient in need thereof a pharmaceutical composition that comprises (i) a blood product and (ii) a therapeutic agent selected from the group consisting of an anthracycline anti-cancer agent, a topoisomerase inhibitor, an oxazaphosphinanyl anti-cancer agent, a nitro-aryl anti-cancer agent, a thiol-reactive functional-group agent that is a halo-aliphatic alkylating agent, a platinum-based antineoplastic compound, an anti-mitotic agent, acrylamide, acrylonitrile, bis(4-fluorobenzyl)trisulfide, a cardiac glycoside, an anti-malarial agent, and a nitric oxide modulator selected from the group consisting of an organo-nitrate ester compound, sodium nitroprusside, and a phosphodiesterase inhibitor. The blood product may be an erythrocyte cell, or may be whole blood. Desirably, the pharmaceutical composition can be administered by intravenous administration. Exemplary anthracycline anti-cancer agents include doxorubicin and epirubicin.

Another aspect of the invention provides a method for administering a therapeutic agent to a patient. The method comprises parenterally administering to a patient in need thereof a pharmaceutical composition that comprises (i) a blood product and (ii) a therapeutically effective amount of an agent selected from the group consisting of an anthracycline anti-cancer agent, a topoisomerase inhibitor, an oxazaphosphinanyl anti-cancer agent, a nitro-aryl anti-cancer agent, a halo-aliphatic alkylating agent, an organo-nitrate ester compound, an organo-platinum compound, an anti-mitotic agent, an alkylating agent, cis-platin, sodium nitroprusside, acrylamide, acrylonitrile, bis(4-fluorobenzyl) trisulfide, a phosphodiesterase inhibitor, a cardiac glycoside, and an anti-malarial agent. The blood product may be an erythrocyte cell, or may be whole blood. Desirably, the pharmaceutical composition can be administered by intravenous administration. Exemplary anthracycline anti-cancer agents include doxorubicin and epirubicin.

Another aspect of the invention provides a method for administering a therapeutic agent to a patient. The method comprises parenterally administering to a patient in need thereof a pharmaceutical composition that comprises (i) a blood product and (ii) a therapeutic agent selected from the group consisting of an anthracycline anti-cancer agent, a topoisomerase inhibitor, an oxazaphosphinanyl anti-cancer agent, a nitro-aryl anti-cancer agent, a thiol-reactive functional-group agent that is a halo-aliphatic alkylating agent, a platinum-based antineoplastic compound, acrylamide, acrylonitrile, bis(4-fluorobenzyl)trisulfide, a cardiac glycoside, an anti-malarial agent, and a nitric oxide modulator selected from the group consisting of an organo-nitrate ester compound, sodium nitroprusside, and a phosphodiesterase inhibitor. The blood product may be an erythrocyte cell, or may be whole blood. Desirably, the pharmaceutical composition can be administered by intravenous administration. Exemplary anthracycline anti-cancer agents include doxorubicin and epirubicin.

Another aspect of the invention provides a method for administering a therapeutic agent to a patient. The method comprises parenterally administering to a patient in need thereof a pharmaceutical composition that comprises (i) a blood product and (ii) a therapeutic agent selected from the group consisting of an anthracycline anti-cancer agent, a topoisomerase inhibitor, an oxazaphosphinanyl anti-cancer agent, a nitro-aryl anti-cancer agent, a halo-aliphatic alkylating agent, an organo-nitrate ester compound, an organo-platinum compound, cis-platin, sodium nitroprusside, acrylamide, acrylonitrile, bis(4-fluorobenzyl)trisulfide, a phosphodiesterase inhibitor, a cardiac glycoside, and an anti-malarial agent. The blood product may be an erythrocyte cell, or may be whole blood. Desirably, the pharmaceutical composition can be administered by intravenous administration. Exemplary anthracycline anti-cancer agents include doxorubicin and epirubicin.

Another aspect of the invention provides a method of treating cancer in a patient. The method comprises parenterally administering to a patient in need thereof a pharmaceutical composition that comprises (i) a blood product and (ii) a therapeutic agent selected from the group consisting of an anthracycline anti-cancer agent, a topoisomerase inhibitor, an oxazaphosphinanyl anti-cancer agent, a nitro-aryl anti-cancer agent, a thiol-reactive functional-group agent, a nitric oxide modulator, a platinum-based antineoplastic compound, acrylamide, acrylonitrile, bis(4-fluorobenzyl) trisulfide, a cardiac glycoside, an anti-mitotic agent, a nucleoside analog, and an EGFR inhibitor, to thereby treat the cancer. The blood product may be an erythrocyte cell, or may be whole blood. Desirably, the pharmaceutical composition can be administered by intravenous administration. Exemplary anthracycline anti-cancer agents include doxorubicin and epirubicin.

Another aspect of the invention provides a method of treating cancer in a patient. The method comprises parenterally administering to a patient in need thereof a pharmaceutical composition that comprises (i) a blood product and (ii) a therapeutic agent selected from the group consisting of an anthracycline anti-cancer agent, a topoisomerase inhibitor, an oxazaphosphinanyl anti-cancer agent, a nitro-aryl anti-cancer agent, a thiol-reactive functional-group agent, a nitric oxide modulator, a platinum-based antineoplastic compound, acrylamide, acrylonitrile, bis(4-fluorobenzyl) trisulfide, a cardiac glycoside, an anti-mitotic agent, and a nucleoside analog, to thereby treat the cancer. The blood product may be an erythrocyte cell, or may be whole blood. Desirably, the pharmaceutical composition can be administered by intravenous administration. Exemplary anthracycline anti-cancer agents include doxorubicin and epirubicin.

Another aspect of the invention provides a method of treating cancer in a patient. The method comprises parenterally administering to a patient in need thereof a pharmaceutical composition that comprises (i) a blood product and (ii) a therapeutic agent selected from the group consisting of an anthracycline anti-cancer agent, a topoisomerase inhibitor, an oxazaphosphinanyl anti-cancer agent, a nitro-aryl anti-cancer agent, a thiol-reactive functional-group agent, a nitric oxide modulator, a platinum-based antineoplastic compound, acrylamide, acrylonitrile, bis(4-fluorobenzyl) trisulfide, a cardiac glycoside, and an anti-mitotic agent, to thereby treat the cancer. The blood product may be an erythrocyte cell, or may be whole blood. Desirably, the pharmaceutical composition can be administered by intravenous administration. Exemplary anthracycline anti-cancer agents include doxorubicin and epirubicin.

Another aspect of the invention provides a method of treating cancer in a patient. The method comprises parenterally administering to a patient in need thereof a pharmaceutical composition that comprises (i) a blood product and (ii) a therapeutic agent selected from the group consisting of an anthracycline anti-cancer agent, a topoisomerase inhibitor, an oxazaphosphinanyl anti-cancer agent, a nitro-aryl anti-cancer agent, a thiol-reactive functional-group agent that is a halo-aliphatic alkylating agent, a platinum-based antineoplastic compound, acrylamide, acrylonitrile, bis(4-fluorobenzyl)trisulfide, and a nitric oxide modulator selected from the group consisting of an organo-nitrate ester compound, sodium nitroprusside, and a phosphodiesterase inhibitor, to thereby treat the cancer. The blood product may be an erythrocyte cell, or may be whole blood. Desirably, the pharmaceutical composition can be administered by intravenous administration. Exemplary anthracycline anti-cancer agents include doxorubicin and epirubicin.

Another aspect of the invention provides a method of treating cancer in a patient. The method comprises parenterally administering to a patient in need thereof a pharmaceutical composition that comprises (i) a blood product and (ii) a therapeutic agent selected from the group consisting of an anthracycline anti-cancer agent, a topoisomerase inhibitor, an oxazaphosphinanyl anti-cancer agent, a nitro-aryl anti-cancer agent, a halo-aliphatic alkylating agent, an organo-nitrate ester compound, an organo-platinum compound, cis-platin, sodium nitroprusside, acrylamide, acrylonitrile, bis(4-fluorobenzyl)trisulfide, and a phosphodiesterase inhibitor, to thereby treat the cancer. The blood product may be an erythrocyte cell, or may be whole blood. Desirably, the pharmaceutical composition can be administered by intravenous administration. Exemplary anthracycline anti-cancer agents include doxorubicin and epirubicin.

Another aspect of the invention provides a method of treating a disease or disorder involving infection in a patient. The method comprises parenterally administering to a patient in need thereof a pharmaceutical composition that comprises (i) a blood product and (ii) a therapeutic agent that is an anti-microbial agent, to thereby treat the disease or disorder involving infection.

Another aspect of the invention provides a pharmaceutical composition, comprising a blood product and one or more therapeutic agents, wherein the therapeutic agent is an anthracycline anti-cancer agent, a topoisomerase inhibitor, an oxazaphosphinanyl anti-cancer agent, a nitro-aryl anti-cancer agent, a thiol-reactive functional-group agent, a nitric oxide modulator, a platinum-based antineoplastic compound, acrylamide, acrylonitrile, bis(4-fluorobenzyl)trisulfide, a cardiac glycoside, an anti-mitotic agent, a nucleoside analog, an EGFR inhibitor, or an anti-microbial agent. The blood product can be from or derived from the patient who is to receive the pharmaceutical composition.

Another aspect of the invention provides a pharmaceutical composition, comprising a blood product and one or more therapeutic agents, wherein the therapeutic agent is an anthracycline anti-cancer agent, a topoisomerase inhibitor, an oxazaphosphinanyl anti-cancer agent, a nitro-aryl anti-cancer agent, a thiol-reactive functional-group agent, a nitric oxide modulator, a platinum-based antineoplastic compound, acrylamide, acrylonitrile, bis(4-fluorobenzyl)trisulfide, a cardiac glycoside, an anti-mitotic agent, a nucleoside analog, or an anti-microbial agent.

Another aspect of the invention provides a pharmaceutical composition, comprising a blood product and one or more therapeutic agents, wherein the therapeutic agent is an anthracycline anti-cancer agent, a topoisomerase inhibitor, an oxazaphosphinanyl anti-cancer agent, a nitro-aryl anti-cancer agent, a thiol-reactive functional-group agent, a nitric oxide modulator, a platinum-based antineoplastic compound, acrylamide, acrylonitrile, bis(4-fluorobenzyl)trisulfide, a cardiac glycoside, an anti-mitotic agent, or an anti-microbial agent.

Another aspect of the invention provides a pharmaceutical composition formulated for parenteral administration, comprising (i) a blood product, and (ii) a therapeutic agent selected from the group consisting of an anthracycline anti-cancer agent, a topoisomerase inhibitor, an oxazaphosphinanyl anti-cancer agent, a nitro-aryl anti-cancer agent, a halo-aliphatic alkylating agent, an organo-nitrate ester compound, an organo-platinum compound, cis-platin, sodium nitroprusside, acrylamide, acrylonitrile, bis(4-fluorobenzyl) trisulfide, a phosphodiesterase inhibitor, a cardiac glycoside, and an anti-malarial agent. The blood product may be erythrocyte cells, or may be whole blood. Desirably, the pharmaceutical composition can be formulated for intravenous administration.

In various embodiments of the methods and pharmaceutical compositions of the invention, the blood product or the components of the blood product (e.g., red blood cells) are not modified or manipulated to load the therapeutic agent thereon and/or therein but rather the blood product and the therapeutic agent are mixed, optionally incubated for a time and under appropriate conditions as described herein, and then administered to a patient. Such modifications of the blood product include, but are not limited to, genetically engineered expression of a target-binding agent or addition of a molecular marker, a fusion molecule, a photosensitive agent, a positive marker, a target recognition moiety, and/or an antibody aptamer; and such manipulations of the cells include, but are not limited to, electroporation, conjugation, endocytosis and/or hypo-osmotic dialysis. In various embodiments where the blood product comprises erythrocyte cells, the erythrocyte cells have not undergone any modification or manipulation such as genetic modification, electroporation, conjugation through biotin, conjugation to a cell-penetrating peptide, conjugation to hemoglobin, dimethyl sulfoxide osmotic pulse, endocytosis and hypotonic preswelling, hypotonic dilution, and/or hypo-osmotic dialysis.

DESCRIPTION OF THE DRAWINGS

FIGS. 6A and 6B depict nephrotoxicity of control, oxaliplatin (L-OHP, 12 mg/kg), and whole blood mixed with carboplatin (Blood-mix-L-OHP, either 12 mg/kg or 24 mg/kg) in treating xenografted HT-29 colorectal tumor, as measured by either serum creatinine level (FIG. 6A) or blood urea nitrogen level (BUN, FIG. 6B) after each treatment.

DETAILED DESCRIPTION

Figure 1:
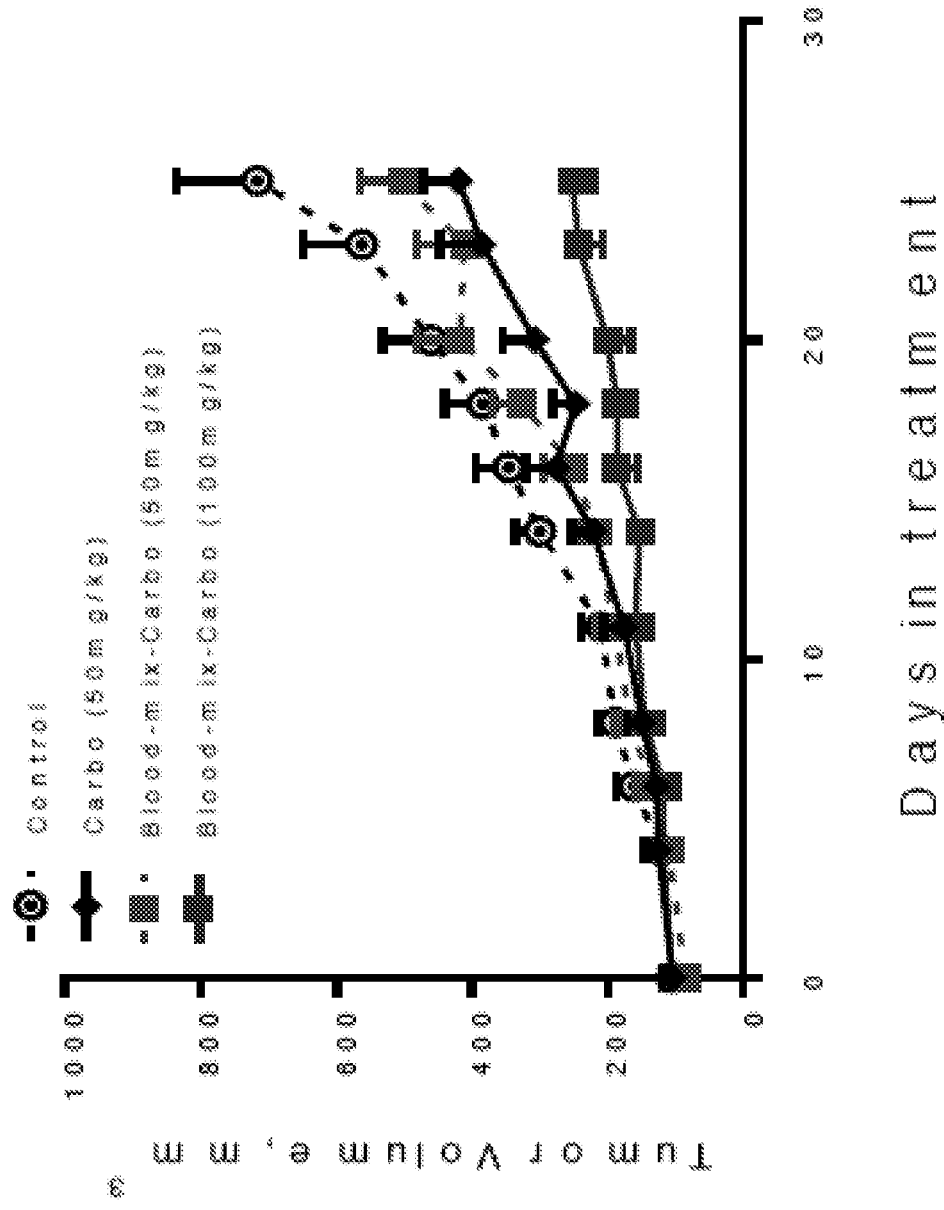
FIG. 1 depicts activity of control, carboplatin (Carbo, 50 mg/kg), and whole blood mixed with carboplatin (Bloodmix-Carbo, either 50 mg/kg or 100 mg/kg) in treating xenografted A549 lung tumor, as measured by tumor volume after each treatment.
Figure 2A:
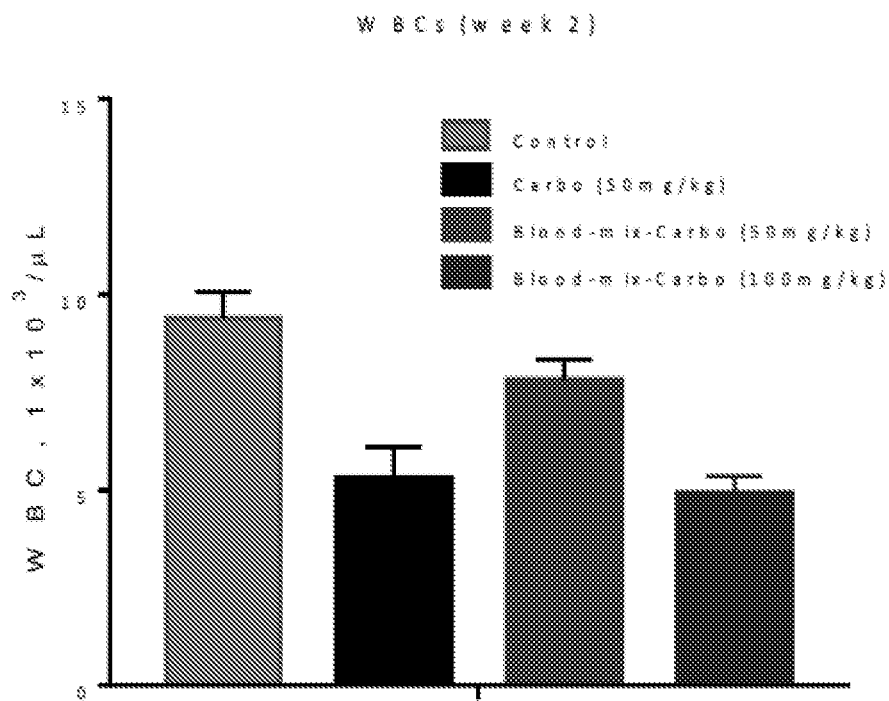
FIGS. 2A and 2B depict myelosuppression toxicity of control, carboplatin (Carbo, 50 mg/kg), and whole blood mixed with carboplatin (Blood-mix-Carbo, either 50 mg/kg or 100 mg/kg) in treating xenografted A549 lung tumor, as measured by white blood cell number either 2 weeks (FIG. 2A) or 3 weeks (FIG. 2B) after each treatment.
Figure 2B:
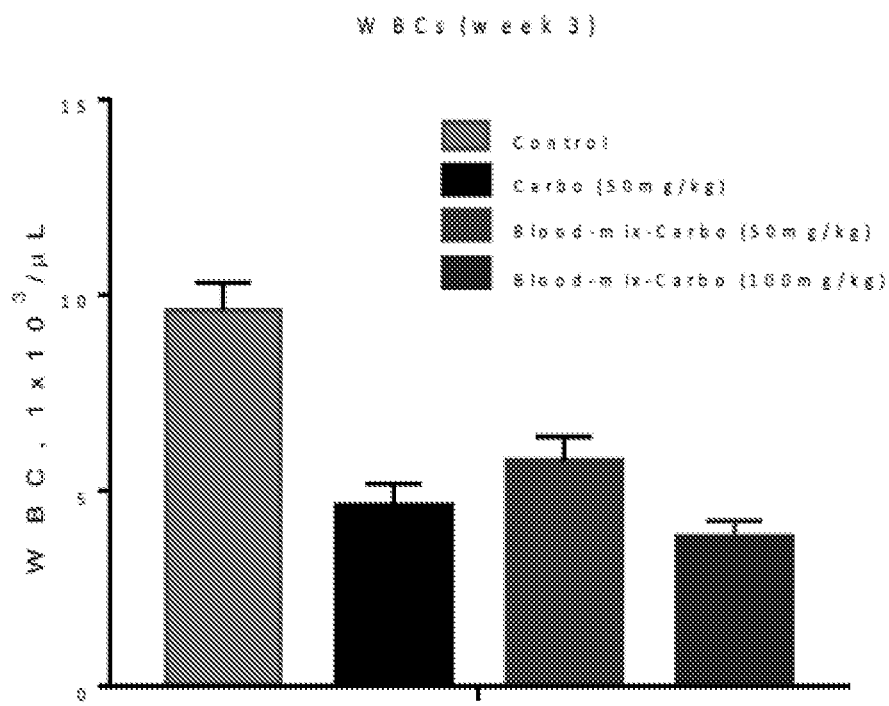
Figure 3A:
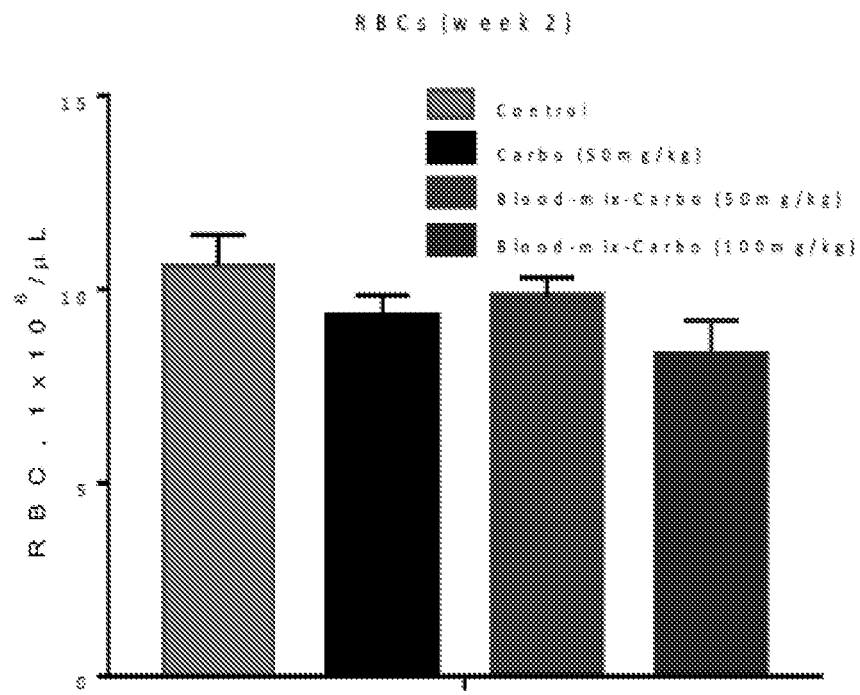
FIGS. 3A and 3B depict myelosuppression toxicity of control, carboplatin (Carbo, 50 mg/kg), and whole blood mixed with carboplatin (Blood-mix-Carbo, either 50 mg/kg or 100 mg/kg) in treating xenografted A549 lung tumor, as measured by red blood cell number either two weeks (FIG. 3A) or three weeks (FIG. 3B) after each treatment.
Figure 3B:
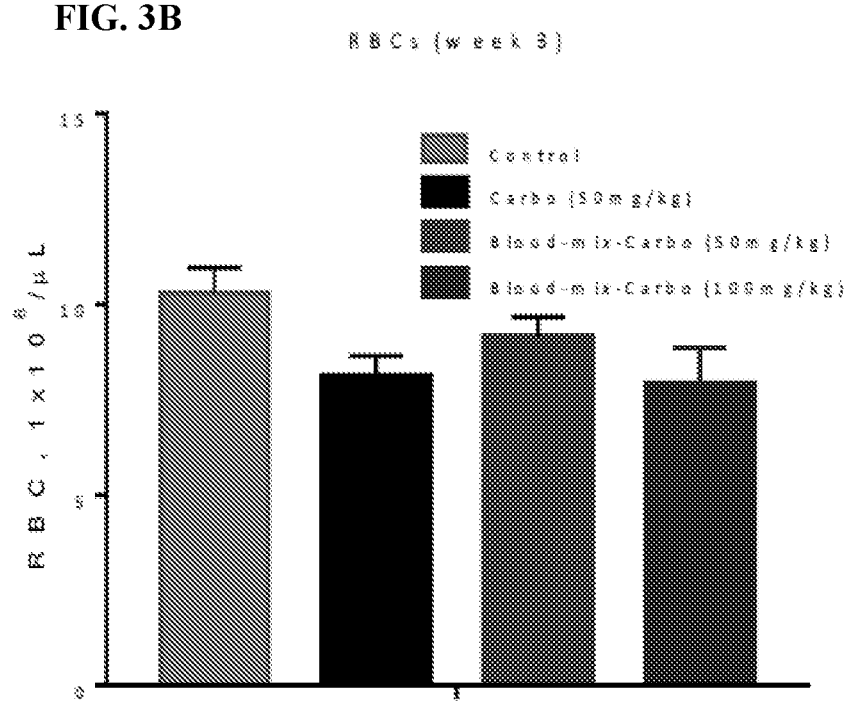
Figure 4A:
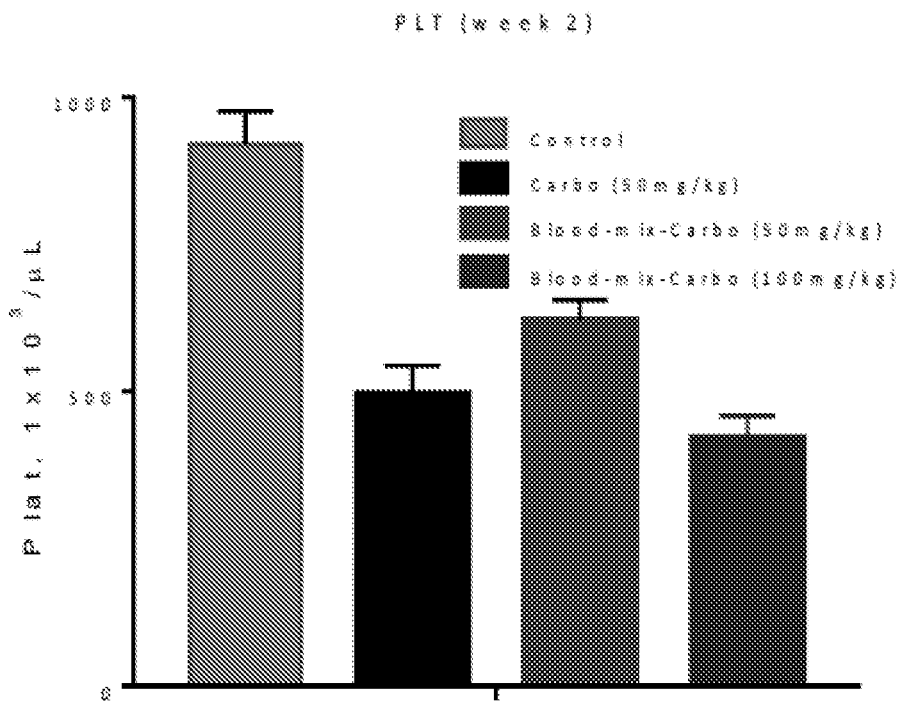
FIGS. 4A and 4B depict myelosuppression toxicity of control, carboplatin (Carbo, 5 mg/kg), and whole blood mixed with carboplatin (Blood-mix-Carbo, either 50 mg/kg or 100 mg/kg) in treating xenografted A549 lung tumor, as measured by platelet number either two weeks (FIG. 4A) or three weeks (FIG. 4B) after each treatment.
Figure 4B:
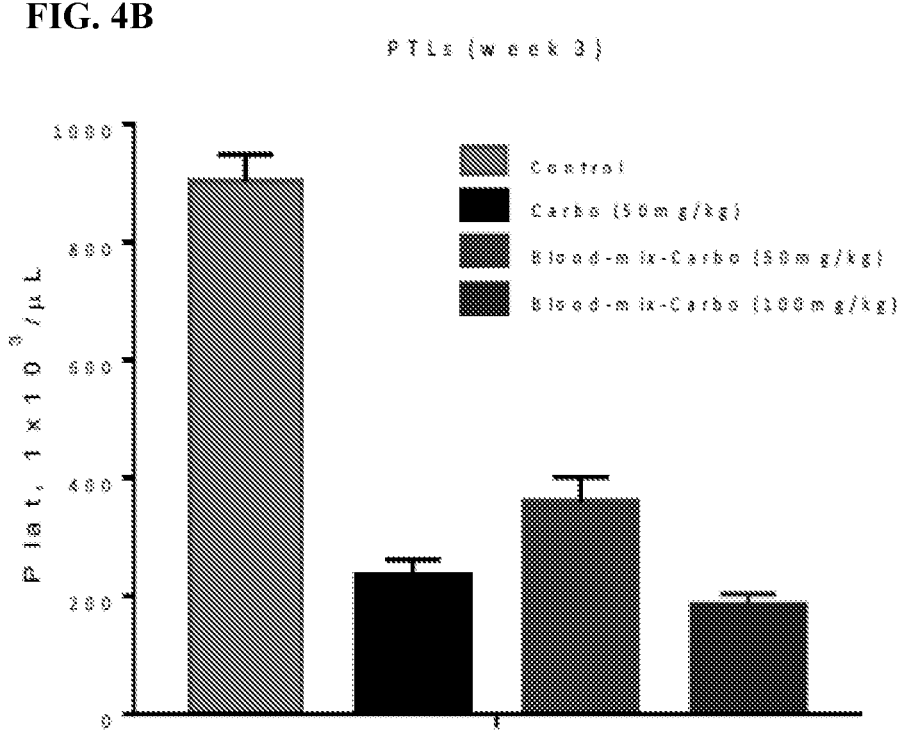

The invention provides compositions and methods for administering a therapeutic agent to a patient, such as pharmaceutical compositions containing a blood product and a therapeutic agent such as an anthracycline anti-cancer agent (e.g., doxorubicin), a topoisomerase inhibitor, an oxazaphosphinanyl anti-cancer agent, a nitro-aryl anti-cancer agent, a thiol-reactive functional-group agent, a nitric oxide modulator, a platinum-based antineoplastic compound, acrylamide, acrylonitrile, bis(4-fluorobenzyl)trisulfide, a cardiac glycoside, an anti-mitotic agent (e.g. paclitaxel), a nucleoside analog, an EGFR inhibitor, or an anti-microbial agent. One exemplary composition contains whole blood and doxorubicin, which may be administered intravenously to a patient, such as for use in treating cancer in a patient. Another exemplary composition contains whole blood and imipenem, which may be administered intravenously to a patient, such as for use in treating a disease or disorder involving infection in a patient (e.g. sepsis). Ex vivo mixing of a therapeutic agent with a blood product to form a pharmaceutical composition can provide benefits to the patient, such as, in certain instances, improvement in the efficacy of the therapeutic agent and/or reduction in adverse side effects.

I. Therapeutic Methods

The invention provides methods for administering a therapeutic agent to a patient and methods for treating disease, such as cancer. The methods generally entail parenterally administering to a patient in need thereof a pharmaceutical composition that comprises (i) a blood product and (ii) a therapeutic agent selected from the group consisting of an anthracycline anti-cancer agent, a topoisomerase inhibitor, an oxazaphosphinanyl anti-cancer agent, a nitro-aryl anti-cancer agent, a thiol-reactive functional-group agent, a nitric oxide modulator, a platinum-based antineoplastic compound, acrylamide, acrylonitrile, bis(4-fluorobenzyl)trisulfide, a cardiac glycoside, an anti-mitotic agent (e.g. paclitaxel), a nucleoside analog, an EGFR inhibitor, and an anti-microbial agent. Ex vivo mixing of a therapeutic agent with a blood product to form a pharmaceutical composition can provide benefits to the patient, such as, in certain instances, improvement in the efficacy of the therapeutic agent and/or reduction in adverse side effects. Various features of the methods are described in sections herein.

Methods for Administering a Therapeutic Agent

One aspect of the invention provides a method for administering a therapeutic agent to a patient. The method generally comprises parenterally administering to a patient in need thereof a pharmaceutical composition that comprises (i) a blood product and (ii) a therapeutic agent selected from the group consisting of an anthracycline anti-cancer agent, a topoisomerase inhibitor, an oxazaphosphinanyl anti-cancer agent, a nitro-aryl anti-cancer agent, a thiol-reactive functional-group agent, a nitric oxide modulator, a platinum-based antineoplastic compound, acrylamide, acrylonitrile, bis(4-fluorobenzyl)trisulfide, a cardiac glycoside, an anti-mitotic agent, a nucleoside analog, an EGFR inhibitor, and an anti-microbial agent.

In various embodiments, the method generally comprises parenterally administering to a patient in need thereof a pharmaceutical composition that comprises (i) a blood product and (ii) a therapeutic agent selected from the group consisting of an anthracycline anti-cancer agent, a topoisomerase inhibitor, an oxazaphosphinanyl anti-cancer agent, a nitro-aryl anti-cancer agent, a thiol-reactive functional-group agent, a nitric oxide modulator, a platinum-based antineoplastic compound, acrylamide, acrylonitrile, bis(4-fluorobenzyl)trisulfide, a cardiac glycoside, an anti-mitotic agent, a nucleoside analog, and an anti-microbial agent.

In various embodiments, the method generally comprises parenterally administering to a patient in need thereof a pharmaceutical composition comprising a blood product and one or more therapeutic agents, wherein the therapeutic agent is an anthracycline anti-cancer agent, a topoisomerase inhibitor, an oxazaphosphinanyl anti-cancer agent, a nitro-aryl anti-cancer agent, a thiol reactive functional group agent, an nitric oxide modulator, a platinum based compound, acrylamide, acrylonitrile, bis(4-fluorobenzyl)trisulfide, a cardiac glycoside, an anti-mitotic agent, an alkylating agent, a nucleoside analog, or an antimicrobial agent.

In various embodiments, the method generally comprises parenterally administering to a patient in need thereof a pharmaceutical composition that comprises (i) a blood product and (ii) a therapeutic agent selected from the group consisting of an anthracycline anti-cancer agent, a topoisomerase inhibitor, an oxazaphosphinanyl anti-cancer agent, a nitro-aryl anti-cancer agent, a thiol-reactive functional-group agent, a nitric oxide modulator, a platinum-based antineoplastic compound, acrylamide, acrylonitrile, bis(4-fluorobenzyl)trisulfide, a cardiac glycoside, an anti-mitotic agent, and an anti-microbial agent.

In various embodiments, the method generally comprises parenterally administering to a patient in need thereof a pharmaceutical composition comprising a blood product and one or more therapeutic agents, wherein the therapeutic agent is an anthracycline anti-cancer agent, a topoisomerase inhibitor, an oxazaphosphinanyl anti-cancer agent, a nitro-aryl anti-cancer agent, a thiol reactive functional group agent, an nitric oxide modulator, a platinum based compound, acrylamide, acrylonitrile, bis(4-fluorobenzyl)trisulfide, a cardiac glycoside, an anti-mitotic agent, an alkylating agent, or an antimicrobial agent.

In various embodiments, the method generally comprises parenterally administering to a patient in need thereof a pharmaceutical composition that comprises (i) a blood product and (ii) a therapeutic agent selected from the group consisting of an anthracycline anti-cancer agent, a topoisomerase inhibitor, an oxazaphosphinanyl anti-cancer agent, a nitro-aryl anti-cancer agent, a thiol-reactive functional-group agent that is a halo-aliphatic alkylating agent, a platinum-based antineoplastic compound, an anti-mitotic agent, acrylamide, acrylonitrile, bis(4-fluorobenzyl)trisulfide, a cardiac glycoside, an anti-malarial agent, and a nitric oxide modulator selected from the group consisting of an organo-nitrate ester compound, sodium nitroprusside, and a phosphodiesterase inhibitor.

In various embodiments, the method generally comprises parenterally administering to a patient in need thereof a pharmaceutical composition that comprises (i) a blood product and (ii) a therapeutically effective amount of an agent selected from the group consisting of an anthracycline anti-cancer agent, a topoisomerase inhibitor, an oxazaphosphinanyl anti-cancer agent, a nitro-aryl anti-cancer agent, a halo-aliphatic alkylating agent, an organo-nitrate ester compound, an organo-platinum compound, an anti-mitotic agent, an alkylating agent, cis-platin, sodium nitroprusside, acrylamide, acrylonitrile, bis(4-fluorobenzyl)trisulfide, a phosphodiesterase inhibitor, a cardiac glycoside, and an anti-malarial agent.

In various embodiments, the method generally comprises parenterally administering to a patient in need thereof a pharmaceutical composition that comprises (i) a blood product and (ii) a therapeutic agent selected from the group consisting of an anthracycline anti-cancer agent, a topoisomerase inhibitor, an oxazaphosphinanyl anti-cancer agent, a nitro-aryl anti-cancer agent, a thiol-reactive functional-group agent that is a halo-aliphatic alkylating agent, a platinum-based antineoplastic compound, acrylamide, acrylonitrile, bis(4-fluorobenzyl)trisulfide, a cardiac glycoside, an anti-malarial agent, and a nitric oxide modulator selected from the group consisting of an organo-nitrate ester compound, sodium nitroprusside, and a phosphodiesterase inhibitor.

In various embodiments, the method generally comprises parenterally administering to a patient in need thereof a pharmaceutical composition that comprises (i) a blood product and (ii) a therapeutic agent selected from the group consisting of an anthracycline anti-cancer agent, a topoisomerase inhibitor, an oxazaphosphinanyl anti-cancer agent, a nitro-aryl anti-cancer agent, a halo-aliphatic alkylating agent, an organo-nitrate ester compound, an organo-platinum compound, cis-platin, sodium nitroprusside, acrylamide, acrylonitrile, bis(4-fluorobenzyl)trisulfide, a phosphodiesterase inhibitor, a cardiac glycoside, and an anti-malarial agent.

In various embodiments, the method generally comprises parenterally administering to a patient a pharmaceutical composition (e.g., a pharmaceutical composition that is formulated for parenteral administration) that comprises (i) a blood product and (ii) a therapeutic agent selected from the group consisting of an anthracycline anti-cancer agent, a topoisomerase inhibitor, a nitro-aryl anti-cancer agent, a halo-aliphatic alkylating agent, an organo-nitrate ester compound, an organo-platinum compound, cis-platin, sodium nitroprusside, acrylamide, acrylonitrile, bis(4-fluorobenzyl)trisulfide, a phosphodiesterase inhibitor, an oxazaphosphinanyl anti-cancer agent, and an anti-malarial agent.

The methods described herein may be characterized based on the identity of the blood product, route of administration, nature of the patient, and other features. For example, in certain embodiments, the blood product comprises erythrocyte cells. In certain embodiments, the blood product is a mixture of packed red blood cells. In certain embodiments, the blood product is whole blood. In certain embodiments, the whole blood is autologous whole blood. In certain embodiments, the whole blood is allogenic whole blood. In certain embodiments, the parenterally administering is intravenous, intramuscular, subcutaneous, intradermal, intratumoral, or intraperitoneal administration. In certain embodiments, the parenterally administering is intravenous administration.

In certain embodiments, the blood product includes one or more types of cells. In certain embodiments, the blood product comprises erythrocyte cells. In certain embodiments, the blood product comprises platelets. In certain embodiments, the blood product comprises white cells. In certain embodiments, the blood product includes one or more of neutrophils, basophils, eosinophils, or dendritic cells. In certain embodiments, the blood product includes any applicable combination of types of cells. By way of examples, in certain embodiments, the blood product includes erythrocytes and platelets. In certain embodiments, the blood product includes erythrocytes and white blood cells. In certain embodiments, the blood product includes packed red blood cells, white blood cells, and platelets.

In certain embodiments, the blood product comprises plasma. In certain embodiments, the blood product comprises or consists of a buffy coat. In certain embodiments, the blood product comprises or consists of platelet rich plasma.

In certain embodiments, no component in the blood product (e.g., the red blood cells) is modified. Modifications of the blood product include, but are not limited to, genetically engineered expression of a target-binding agent or addition of a molecular marker, a fusion molecule, a photosensitive agent, a positive marker, a target recognition moiety, and/or an antibody aptamer; or manipulating the cells by electroporation, conjugation, endocytosis and/or hypo-osmotic dialysis. In certain embodiments, the blood product comprises erythrocyte cells, and the erythrocyte cells have not undergone any manipulation selected from the group consisting of genetic modification, electroporation, conjugation through biotin, conjugation to a cell-penetrating peptide, conjugation to hemoglobin, dimethyl sulfoxide osmotic pulse, endocytosis and hypotonic preswelling, hypotonic dilution, and hypo-osmotic dialysis.

In some embodiments, the pharmaceutical composition is engulfed or phagocytosed by macrophages after administration to a patient. Without wishing to be bound to any particular theory, the therapeutic agent may bind to and/or penetrate into red blood cells, which are engulfed or phagocytosed by macrophages such that the therapeutic agent makes its way into the macrophage via the red blood cells.

In certain embodiments, the patient suffers from cancer. In certain embodiments, the patient suffers from malaria. In certain embodiments, the patient suffers from a microbial infection, sickle cell disease, pulmonary hypertension, or an ischemic condition. In certain embodiments, the patient suffers from sickle cell disease, pulmonary hypertension, or an ischemic condition.

In certain embodiments, the therapeutic agent is an anti-cancer agent. In certain embodiments, the therapeutic agent is an anti-malarial agent. In certain embodiments, the anti-malarial agent is artemisinin.

The therapeutic method can be used to administer therapeutic agents in addition to those listed above. For example, in certain embodiments, the therapeutic agent is selected from:
(a) a phenytoin, pentobarbital, phenothiazine, acetazolamide, chlorthalidone, imipramine, chlorpromazine, arsenic, or carbon monoxide;
(b) a therapeutic agent having anti-babesial activity, anti-*Bartonella* henselae activity, or anti-toxoplasmosis activity;
(c) an oxygen release enhancer, 2,3,-diphosphoglycerate, RSR-13, or RSR-4;
(d) topotecan;
(e) a *Digitalis* glycoside (i.e. cardiac glycoside), such as digoxin, digitoxin, or ouabain; (f) penicillin G, dicloxacillin, tetracycline, or minocycline;
(g) propranolol;
(h) propofol;
(i) a therapeutic agent that partitions into white cells; and
(j) acetylsalicylic acid, N-acetylcystein, 4-aminophenol, azathioprine, bunolol, captopril, chlorpromazine, dapsone, daunorubicin, dehydroepiandrosterone, didanosin, dopamine, epinephrine, esmolol, estradiol, estrone, etoposide, 5-fluorouracil, haloperidol, heroin, insulin, isoproterenol, isosorbide dinitrate, LY 217896, 6-mercaptopurine, misonidazole, nitroglycerin, norepinephrine, para-aminobenzoic acid, para-aminosalicylic acid, penicillamin, pentaerythritol tetranitrate, pentoxyphillin, procainamide, procaine, progesterone, ribavirin, sulfanilamide, testosterone, thioguanine, or thiospirolactone.

Methods of Treating Cancer

Another aspect of the invention provides a method of treating cancer in a patient. The method generally comprises parenterally administering to a patient in need thereof a pharmaceutical composition that comprises (i) a blood product and (ii) a therapeutic agent selected from the group consisting of an anthracycline anti-cancer agent, a topoisomerase inhibitor, an oxazaphosphinanyl anti-cancer agent, a nitro-aryl anti-cancer agent, a thiol-reactive functional-group agent, a nitric oxide modulator, a platinum-based antineoplastic compound, acrylamide, acrylonitrile, bis(4-fluorobenzyl)trisulfide, a cardiac glycoside, an anti-mitotic agent, a nucleoside analog, and an EGFR inhibitor, to thereby treat the cancer. The blood product may be an erythrocyte cell, or may be whole blood. Desirably, the pharmaceutical composition is administered by intravenous administration. Exemplary anthracycline anti-cancer agents include doxorubicin and epirubicin.

In various embodiments, the method generally comprises parenterally administering to a patient in need thereof a pharmaceutical composition that comprises (i) a blood product and (ii) a therapeutic agent selected from the group consisting of an anthracycline anti-cancer agent, a topoisomerase inhibitor, an oxazaphosphinanyl anti-cancer agent, a nitro-aryl anti-cancer agent, a thiol-reactive functional-group agent, a nitric oxide modulator, a platinum-based antineoplastic compound, acrylamide, acrylonitrile, bis(4-fluorobenzyl)trisulfide, a cardiac glycoside, an anti-mitotic agent, and a nucleoside analog, to thereby treat the cancer. The blood product may be an erythrocyte cell, or may be whole blood. Desirably, the pharmaceutical composition is administered by intravenous administration. Exemplary anthracycline anti-cancer agents include doxorubicin and epirubicin.

In various embodiments, the method generally comprises administering to a patient a pharmaceutical composition comprising a blood product and one or more therapeutic agents, wherein the therapeutic agent is an anthracycline anti-cancer agent, a topoisomerase inhibitor, an oxazaphosphinanyl anti-cancer agent, a nitro-aryl anti-cancer agent, a thiol reactive functional group agent, an nitric oxide modulator, a platinum based compound, acrylamide, acrylonitrile, bis(4-fluorobenzyl)trisulfide, a cardiac glycoside, an anti-mitotic agent, an alkylating agent, a nucleoside analog, or an antimicrobial agent.

In various embodiments, the method generally comprises parenterally administering to a patient in need thereof a pharmaceutical composition that comprises (i) a blood product and (ii) a therapeutic agent selected from the group consisting of an anthracycline anti-cancer agent, a topoisomerase inhibitor, an oxazaphosphinanyl anti-cancer agent, a nitro-aryl anti-cancer agent, a thiol-reactive functional-group agent, a nitric oxide modulator, a platinum-based antineoplastic compound, acrylamide, acrylonitrile, bis(4-fluorobenzyl)trisulfide, a cardiac glycoside, and an anti-mitotic agent, to thereby treat the cancer. The blood product may be an erythrocyte cell, or may be whole blood. Desirably, the pharmaceutical composition is administered by intravenous administration. Exemplary anthracycline anti-cancer agents include doxorubicin and epirubicin.

In various embodiments, the method generally comprises administering to a patient a pharmaceutical composition comprising a blood product and one or more therapeutic agents, wherein the therapeutic agent is an anthracycline anti-cancer agent, a topoisomerase inhibitor, an oxazaphosphinanyl anti-cancer agent, a nitro-aryl anti-cancer agent, a thiol reactive functional group agent, an nitric oxide modulator, a platinum based compound, acrylamide, acrylonitrile, bis(4-fluorobenzyl)trisulfide, a cardiac glycoside, an antimitotic agent, an alkylating agent, or an antimicrobial agent.

In various embodiments, the method generally comprises parenterally administering to a patient in need thereof a pharmaceutical composition that comprises (i) a blood product and (ii) a therapeutic agent selected from the group consisting of an anthracycline anti-cancer agent, a topoisomerase inhibitor, an oxazaphosphinanyl anti-cancer agent, a nitro-aryl anti-cancer agent, a thiol-reactive functional-group agent that is a halo-aliphatic alkylating agent, a platinum-based antineoplastic compound, acrylamide, acrylonitrile, bis(4-fluorobenzyl)trisulfide, and a nitric oxide modulator selected from the group consisting of an organo-nitrate ester compound, sodium nitroprusside, and a phosphodiesterase inhibitor, to thereby treat the cancer. The blood product may be an erythrocyte cell, or may be whole blood. Desirably, the pharmaceutical composition is administered by intravenous administration. Exemplary anthracycline anti-cancer agents include doxorubicin and epirubicin.

In various embodiments, the method generally comprises parenterally administering to a patient in need thereof a pharmaceutical composition that comprises (i) a blood product and (ii) a therapeutic agent selected from the group consisting of an anthracycline anti-cancer agent, a topoisomerase inhibitor, an oxazaphosphinanyl anti-cancer agent, a nitro-aryl anti-cancer agent, a halo-aliphatic alkylating agent, an organo-nitrate ester compound, an organo-platinum compound, cis-platin, sodium nitroprusside, acrylamide, acrylonitrile, bis(4-fluorobenzyl)trisulfide, and a phosphodiesterase inhibitor, to thereby treat the cancer.

The methods described herein may be characterized based on the identity of the blood product, route of administration, and other features. For example, in certain embodiments, the blood product comprises erythrocyte cells. In certain embodiments, the blood product is a mixture of packed red blood cells. In certain embodiments, the blood product is whole blood. In certain embodiments, the whole blood is autologous whole blood. In certain embodiments, the whole blood is allogenic whole blood. In certain embodiments, the parenterally administering is intravenous, intramuscular, subcutaneous, intradermal, intratumoral, or intraperitoneal administration. In certain embodiments, the parenterally administering is intravenous administration.

In certain embodiments, the blood product includes one or more types of cells. In certain embodiments, the blood product comprises erythrocyte cells. In certain embodiments, the blood product comprises platelets. In certain embodiments, the blood product comprises white cells. In certain embodiments, the blood product includes one or more of neutrophils, basophils, eosinophils, or dendritic cells. In certain embodiments, the blood product includes any applicable combination of types of cells. By way of examples, in certain embodiments, the blood product includes erythrocytes and platelets. In certain embodiments, the blood product includes erythrocytes and white blood cells. In certain embodiments, the blood product includes packed red blood cells, white blood cells, and platelets.

In certain embodiments, the blood product comprises plasma. In certain embodiments, the blood product comprises or consists of a buffy coat. In certain embodiments, the blood product comprises or consists of platelet rich plasma.

In certain embodiments, no component in the blood product (e.g., the red blood cells) is modified. Modifications of the blood product include but are not limited to genetically engineered expression of a target-binding agent or addition of a molecular marker, a fusion molecule, a photosensitive agent, a positive marker, a target recognition moiety, or an antibody aptamer; or manipulating the cells by electroporation, conjugation, endocytosis or hypo-osmotic dialysis. In certain embodiments, the blood product comprises erythrocyte cells, and the erythrocyte cells have not undergone any manipulation selected from the group consisting of genetic modification, electroporation, conjugation through biotin, conjugation to a cell-penetrating peptide, conjugation to hemoglobin, dimethyl sulfoxide osmotic pulse, endocytosis and hypotonic preswelling, hypotonic dilution, and hypo-osmotic dialysis.

Methods of Treating a Disease or Disorder Involving Infection

Another aspect of the invention provides a method of treating a disease or disorder involving infection in a patient. The method generally comprises parenterally administering to a patient in need thereof a pharmaceutical composition that comprises (i) a blood product and (ii) a therapeutic agent that is an anti-microbial agent, to thereby treat the disease or disorder involving infection.

Another aspect of the invention provides a method of treating a disease or disorder involving infection, or an autoimmune or inflammatory disease, in a patient. The method generally comprises administering to a patient a pharmaceutical composition comprising a blood product and one or more therapeutic agents, wherein the therapeutic agent is an anthracycline anti-cancer agent, a topoisomerase inhibitor, an oxazaphosphinanyl anti-cancer agent, a nitro-aryl anti-cancer agent, a thiol reactive functional group agent, an nitric oxide modulator, a platinum based compound, acrylamide, acrylonitrile, bis(4-fluorobenzyl)trisulfide, a cardiac glycoside, an anti-mitotic agent, an alkylating agent, a nucleoside analog, or an antimicrobial agent. In certain embodiments, the autoimmune or inflammatory disease is rheumatoid arthritis, ulcerative colitis, Crohn's disease, psoriasis, osteomyelitis, multiple sclerosis, atherosclerosis, pulmonary fibrosis, sarcoidosis, systemic sclerosis, organ transplant rejection (GVHD), cystic fibrosis, asthma, chronic obstructive pulmonary disease (COPD), or chronic inflammations.

Another aspect of the invention provides a method of treating a disease or disorder involving infection, or an autoimmune or inflammatory disease, in a patient. The method generally comprises administering to a patient a pharmaceutical composition comprising a blood product and one or more therapeutic agents, wherein the therapeutic agent is an anthracycline anti-cancer agent, a topoisomerase inhibitor, an oxazaphosphinanyl anti-cancer agent, a nitro-aryl anti-cancer agent, a thiol reactive functional group agent, an nitric oxide modulator, a platinum based compound, acrylamide, acrylonitrile, bis(4-fluorobenzyl)trisulfide, a cardiac glycoside, an anti-mitotic agent, an alkylating agent, or an antimicrobial agent.

Another aspect of the invention provides a method of treating malaria in a patient. The method generally comprises parenterally administering to a patient in need thereof a pharmaceutical composition that comprises (i) a blood product and (ii) a therapeutic agent that is an anti-malarial agent, to thereby treat the malaria.

The methods described herein may be characterized based on the identity of the blood product, route of administration, and other features. For example, in certain embodiments, the blood product comprises erythrocyte cells. In certain embodiments, the blood product is a mixture of packed red blood cells. In certain embodiments, the blood product is whole blood. In certain embodiments, the whole blood is autologous whole blood. In certain embodiments, the whole blood is allogenic whole blood. In certain embodiments, the parenterally administering is intravenous, intramuscular, subcutaneous, intradermal, intratumoral, or intraperitoneal administration. In certain embodiments, the parenterally administering is intravenous administration.

In certain embodiments, the blood product includes one or more types of cells. In certain embodiments, the blood product comprises erythrocyte cells. In certain embodiments, the blood product comprises platelets. In certain embodiments, the blood product comprises white cells. In certain embodiments, the blood product includes one or more of neutrophils, basophils, eosinophils, or dendritic cells. In certain embodiments, the blood product includes any applicable combination of types of cells. By way of examples, in certain embodiments, the blood product includes erythrocytes and platelets. In certain embodiments, the blood product includes erythrocytes and white blood cells. In certain embodiments, the blood product includes packed red blood cells, white blood cells, and platelets.

In certain embodiments, the blood product comprises plasma. In certain embodiments, the blood product comprises or consists of a buffy coat. In certain embodiments, the blood product comprises or consists of platelet rich plasma.

In certain embodiments, no component in the blood product (e.g., the red blood cells) is modified. Modifications of the blood product include but are not limited to genetically engineered expression of a target-binding agent or addition of a molecular marker, a fusion molecule, a photosensitive agent, a positive marker, a target recognition moiety, or an antibody aptamer; or manipulating the cells by electroporation, conjugation, endocytosis or hypo-osmotic dialysis. In certain embodiments, the blood product comprises erythrocyte cells, and the erythrocyte cells have not undergone any manipulation selected from the group consisting of genetic modification, electroporation, conjugation through biotin, conjugation to a cell-penetrating peptide, conjugation to hemoglobin, dimethyl sulfoxide osmotic pulse, endocytosis and hypotonic preswelling, hypotonic dilution, and hypo-osmotic dialysis.

In certain embodiments, the autoimmune or inflammatory disease is rheumatoid arthritis, ulcerative colitis, Crohn's disease, psoriasis, osteomyelitis, multiple sclerosis, atherosclerosis, pulmonary fibrosis, sarcoidosis, systemic sclerosis, organ transplant rejection (GVHD), cystic fibrosis, asthma, chronic obstructive pulmonary disease (COPD), or chronic inflammations.

Exemplary Features of the Methods for Administering a Therapeutic Agent and Methods of Treating Cancer The methods for administering a therapeutic agent and for treating cancer may be characterized by additional features, such as the type of cancer, identity of the therapeutic agent, and other features as described in more detail herein.

Type of Cancer

The methods may be characterized according to the type of cancer. Accordingly, in certain embodiments, the cancer is a solid tumor. In certain embodiments, the solid tumor is a sarcoma or carcinoma. In certain embodiments, the cancer is brain cancer, bladder cancer, breast cancer, cervical cancer, cholangiocarcinoma, colon cancer, colorectal cancer, endometrial cancer, esophageal cancer, lung cancer, liver cancer, melanoma, ovarian cancer, pancreatic cancer, prostate cancer, rectal cancer, renal cancer, stomach cancer, testicular cancer, uterine cancer, or Kaposi's sarcoma. In certain embodiments, the cancer is a leukemia or lymphoma. In certain embodiments, the cancer is breast cancer, bladder cancer, or Kaposi's sarcoma. In certain embodiments, the cancer is lymphoma or acute lymphocytic leukemia.

In some embodiments, the cancer is brain cancer, bladder cancer, breast cancer, cervical cancer, cholangiocarcinoma, colon cancer, colorectal cancer, endometrial cancer, esophageal cancer, lung cancer, liver cancer, melanoma, ovarian cancer, pancreatic cancer, prostate cancer, rectal cancer, renal cancer, stomach cancer, testicular cancer, or uterine cancer. In certain embodiments, the cancer is brain cancer. In certain embodiments, the cancer is colorectal cancer. In certain embodiments, the cancer is cholangiocarcinoma or lung cancer.

In certain embodiments, the cancer is lung cancer. In certain embodiments, the lung cancer is small cell lung cancer. In certain embodiments, the cancer is non-small cell lung cancer. In certain embodiments, the cancer is a leukemia or lymphoma. In certain embodiments, the cancer is a B-cell lymphoma or non-Hodgkin lymphoma.

Exemplary cancers for treatment include, for example, bladder cancer, breast cancer, cervical cancer, colon cancer, colorectal cancer, endometrial cancer, esophageal cancer, leukemia, lung cancer, liver cancer, melanoma, ovarian cancer, pancreatic cancer, prostate cancer, rectal cancer, renal cancer, stomach cancer, testicular cancer, and uterine cancer. In some embodiments, the cancer is a vascularized tumor, squamous cell carcinoma, adenocarcinoma, small cell carcinoma, melanoma, glioma, neuroblastoma, sarcoma (e.g., an angiosarcoma or chondrosarcoma), larynx cancer, parotid cancer, bilary tract cancer, thyroid cancer, acral lentiginous melanoma, actinic keratoses, acute lymphocytic leukemia, acute myeloid leukemia, adenoid cystic carcinoma, adenomas, adenosarcoma, adenosquamous carcinoma, anal canal cancer, anal cancer, anorectum cancer, astrocytic tumor, bartholin gland carcinoma, basal cell carcinoma, biliary cancer, bone cancer, bone marrow cancer, bronchial cancer, bronchial gland carcinoma, carcinoid, cholangiocarcinoma, chondosarcoma, choriod plexus papilloma/carcinoma, chronic lymphocytic leukemia, chronic myeloid leukemia, clear cell carcinoma, connective tissue cancer, cystadenoma, digestive system cancer, duodenum cancer, endocrine system cancer, endodermal sinus tumor, endometrial hyperplasia, endometrial stromal sarcoma, endometrioid adenocarcinoma, endothelial cell cancer, ependymal cancer, epithelial cell cancer, Ewing's sarcoma, eye and orbit cancer, female genital cancer, focal nodular hyperplasia, gallbladder cancer, gastric antrum cancer, gastric fundus cancer, gastrinoma, glioblastoma, glucagonoma, heart cancer, hemangiblastomas, hemangioendothelioma, hemangiomas, hepatic adenoma, hepatic adenomatosis, hepatobiliary cancer, hepatocellular carcinoma, Hodgkin's disease, ileum cancer, insulinoma, intaepithelial neoplasia, interepithelial squamous cell neoplasia, intrahepatic bile duct cancer, invasive squamous cell carcinoma, jejunum cancer, joint cancer, Kaposi's sarcoma, pelvic cancer, large cell carcinoma, large intestine cancer, leiomyosarcoma, lentigo maligna melanomas, lymphoma, male genital cancer, malignant melanoma, malignant mesothelial tumors, medulloblastoma, medulloepithelioma, meningeal cancer, mesothelial cancer, metastatic carcinoma, mouth cancer, mucoepidermoid carcinoma, multiple myeloma, muscle cancer, nasal tract cancer, nervous system cancer, neuroepithelial adenocarcinoma nodular melanoma, non-epithelial skin cancer, non-Hodgkin's lymphoma, oat cell carcinoma, oligodendroglial cancer, oral cavity cancer, osteosarcoma, papillary serous adenocarcinoma, penile cancer, pharynx cancer, pituitary tumors, plasmacytoma, pseudosarcoma, pulmonary blastoma, rectal cancer, renal cell carcinoma, respiratory system cancer, retinoblastoma, rhabdomyosarcoma, sarcoma, serous carcinoma, sinus cancer, skin cancer, small cell carcinoma, small intestine cancer, smooth muscle cancer, soft tissue cancer, somatostatin-secreting tumor, spine cancer, squamous cell carcinoma, striated muscle cancer, submesothelial cancer, superficial spreading melanoma, T cell leukemia, tongue cancer, undifferentiated carcinoma, ureter cancer, urethra cancer, urinary bladder cancer, urinary system cancer, uterine cervix cancer, uterine corpus cancer, uveal melanoma, vaginal cancer, verrucous carcinoma, VIPoma, vulva cancer, well differentiated carcinoma, or Wilms tumor.

The methods may be characterized according to the stage of the cancer. Accordingly, in certain embodiments, the cancer is in stage 0. In certain embodiments, the cancer is in stage I. In certain embodiments, the cancer is in stage II. In certain embodiments, the cancer is in stage III. In certain embodiments, the cancer is in stage IV.

Identity of the Therapeutic Agent

The methods may be characterized according to the identity of the therapeutic agent. Accordingly, in certain embodiments, the therapeutic agent is an anthracycline anti-cancer agent. In certain embodiments, the anthracycline anti-cancer agent is doxorubicin, daunorubicin, idarubicin, liposomal doxorubicin, or any combination thereof. In certain embodiments, the anthracycline anti-cancer agent comprises doxorubicin. In certain embodiments, the anthracycline anti-cancer agent comprises epirubicin. In certain embodiments, the therapeutic agent is a topoisomerase inhibitor. In certain embodiments, the topoisomerase inhibitor is irinotecan, topotecan, etoposide, teniposide, mitoxantrone, or any combination thereof. In certain embodiments, the topoisomerase inhibitor comprises topotecan. In certain embodiments, the topoisomerase inhibitor comprises irinotecan. In certain embodiments, the therapeutic agent is an oxazaphosphinanyl anti-cancer agent. In certain embodiments, the oxazaphosphinanyl anti-cancer agent is ifosfamide, cyclophosphamide, trofosfamide, or any combination thereof. In certain embodiments, the oxazaphosphinanyl anti-cancer agent comprises ifosfamide. In certain embodiments, the oxazaphosphinanyl anti-cancer agent is cyclophosphamide. In certain embodiments, the therapeutic agent is a nitro-aryl anti-cancer agent. In certain embodiments, the nitro-aryl anti-cancer agent comprises iniparib or 2,4,6-trinitrotoluene. In certain embodiments, the nitro-aryl anti-cancer agent comprises iniparib. In certain embodiments, the therapeutic agent is a thiol-reactive functional-group agent that is a halo-aliphatic alkylating agent. In certain embodiments, the therapeutic agent is a halo-aliphatic alkylating agent. In certain embodiments, the halo-aliphatic alkylating agent comprises 3-bromopyruvate, 2-iodoacetamide, 2-bromoacetamide, iodoacetic acid, or bromoacetic acid. In certain embodiments, the therapeutic agent is an organo-nitrate ester compound. In certain embodiments, the organo-nitrate ester compound comprises nitroglycerin. In certain embodiments, the therapeutic agent is an organo-platinum compound. In certain embodiments, the organo-platinum compound comprises carboplatinum. In certain embodiments, the therapeutic agent is cis-platin, sodium nitroprusside, acrylamide, acrylonitrile, or bis(4-fluorobenzyl)trisulfide. In certain embodiments, the therapeutic agent is a phosphodiesterase inhibitor. In certain embodiments, the phosphodiesterase inhibitor comprises avanafil, lodenafil, mirodenafil, sildenafil, tadalafil, vardenafil, udenafil, or zaprinast. In certain embodiments, the therapeutic agent is a cardiac glycoside (e.g., digoxin or digitoxin). In certain embodiments, the cardiac glycoside is digoxin, digitoxin, ouabain, or oleandrin.

In certain embodiments, the therapeutic agent is an EGFR inhibitor. In certain embodiments, the EGFR inhibitor is erlotinib, gefitinib, lapatinib, vandetanib, neratinib, or osimertinib. In certain embodiments, the therapeutic agent is a nucleoside analog. In certain embodiments, the nucleoside analog is gemcitabine, didanosine, vidarabine, cytarabin, emtricitabine, lamivudine, zalcitabine, abacavir, acyclovir, entecavir, idoxuridine, trifluridine, or any combination thereof.

In certain embodiments, the therapeutic agent is a thiol-reactive functional-group agent. In certain embodiments, the thiol-reactive functional-group agent is selected from the group consisting of 3-bromopyruvate, 2-iodoacetamide, 2-bromoacetamide, chloroacetic acid, iodoacetic acid, chloroacetamide, bromoacetic acid, maleimide, vinyl pyridine, disulfide, pyridyl disulfide, isocyanate, and isothiocyanate. In certain embodiments, the thiol-reactive functional-group agent is selected from the group consisting of maleimide, vinyl pyridine, disulfide, pyridyl disulfide, isocyanate, and isothiocyanate. In certain embodiments, the therapeutic agent is an anti-mitotic agent. In certain embodiments, the anti-mitotic agent is paclitaxel.

In certain embodiments, the therapeutic agent is a nitric oxide modulator. In certain embodiments, the nitric oxide modulator is nitroglycerin, nitroprusside, diethylamine/NO, diethylenetriamine/NO, amyl nitrite, isosorbide dinitrate, isosorbide 5-mononitrate, nicorandil, nitroaspirins, S-nitroso-NSAIDs, phosphodiesterase inhibitors, ACE inhibitors, calcium channel blockers, statins, or any combination thereof. In certain embodiments, the therapeutic agent is a nitric oxide modulator that is an organo-nitrate ester compound. In certain embodiments, the therapeutic agent is a nitric oxide modulator that is a phosphodiesterase inhibitor. In certain embodiments, the nitric oxide modulator is nitroglycerin, sodium nitroprusside, or a phosphodiesterase inhibitor.

In certain embodiments, the therapeutic agent is a platinum-based antineoplastic compound. In certain embodiments, the platinum-based antineoplastic compound is cisplatin, nedaplatin, triplatin tetranitrate, phenanthriplatin, picoplatin, satraplatin, carboplatin, oxaliplatin, or any combination thereof. In certain embodiments, the platinum-based antineoplastic compound is cisplatin, carboplatin, oxaliplatin, nedaplatin, or any combination thereof. In certain embodiments, the platinum-based antineoplastic compound comprises carboplatinum. In certain embodiments, the platinum-based antineoplastic compound comprises oxaliplatin.

In certain embodiments, the therapeutic agent is a topoisomerase inhibitor. In certain embodiments, the topoisomerase inhibitor is a type I topoisomerase inhibitor. In certain embodiments, the type I topoisomerase inhibitor is irinotecan or topotecan. In certain embodiments, the topoisomerase inhibitor is a type II topoisomerase inhibitor. In certain embodiments, the type II topoisomerase inhibitor is an anthracycline, etoposide, teniposide, or nitoxantrone. In certain embodiments, the type II topoisomerase inhibitor is etoposide, teniposide, or nitoxantrone.

In some embodiments, the therapeutic agent is doxorubicin. In some embodiments, the therapeutic agent is adriamycin. In some embodiments, the therapeutic agent is cisplatin. In some embodiments, the therapeutic agent is paclitaxel. In some embodiments, the therapeutic agent is cyclophosphamide. In some embodiments, the therapeutic agent is topotecan. In some embodiments, the therapeutic agent is ifosfamide. In some embodiments, the therapeutic agent is irinotecan. In some embodiments, the therapeutic agent is digoxin.

Identity of the Therapeutic Agent and Type of Cancer

The methods may be characterized according to both the identity of the therapeutic agent and the type of cancer. Accordingly, in certain embodiments, the therapeutic agent is erlotinib, and the cancer is non-small cell lung cancer or pancreatic cancer. In certain embodiments, the therapeutic agent is gemicitabine, and the cancer is ovarian cancer, breast cancer, non-small cell lung cancer, or pancreatic cancer. In certain embodiments, the therapeutic agent is paclitaxel, and the cancer is ovarian cancer, breast cancer, lung cancer, Kaposi sarcoma, cervical cancer, or pancreatic cancer. In certain embodiments, the therapeutic agent is cyclophosphamide, and the cancer is lymphoma, multiple myeloma, leukemia, ovarian cancer, breast cancer, small cell lung cancer, neuroblastoma, or sarcoma. In certain embodiments, the therapeutic agent is doxorubicin, and the cancer is breast cancer, bladder cancer, Kaposi's sarcoma, lymphoma, or acute lymphocytic leukemia. In certain embodiments, the therapeutic agent is cisplatin, and the cancer is testicular cancer, ovarian cancer, cervical cancer, breast cancer, bladder cancer, head and neck cancer, esophageal cancer, lung cancer, mesothelioma, brain tumors or neuroblastoma. In certain embodiments, the therapeutic agent is carboplatin, and the cancer is ovarian cancer, lung cancer, head and neck cancer, brain cancer, or neuroblastoma. In certain embodiments, the therapeutic agent is oxaliplatin, and the cancer is colorectal cancer. In certain embodiments, the therapeutic agent is irinotecan, and the cancer is colon cancer or small cell lung cancer.

In certain embodiments, the therapeutic agent is epirubicin, and the cancer is breast cancer. In certain embodiments, the therapeutic agent is daunorubicin, and the cancer is acute myeloid leukemia (AML), acute lymphocytic leukemia (ALL), chronic myelogenous leukemia (CML), or Kaposi's sarcoma. In certain embodiments, the therapeutic agent is idarubicin, and the cancer is a leukemia. In certain embodiments, the therapeutic agent is liposomal doxorubicin, and the cancer is Kaposi's sarcoma, ovarian cancer or multiple myeloma. In certain embodiments, the therapeutic agent is ifosfamide, and the cancer is testicular cancer, soft tissue sarcoma, osteosarcoma, bladder cancer, small cell lung cancer, cervical cancer, or ovarian cancer. In certain embodiments, the therapeutic agent is iniparib, and the cancer is breast cancer. In certain embodiments, the therapeutic agent is topotecan, and the cancer is ovarian cancer, cervical cancer, or small cell lung carcinoma. In certain embodiments, the therapeutic agent is etoposide, and the cancer is testicular cancer, lung cancer, lymphoma, leukemia, neuroblastoma, and ovarian cancer. In certain embodiments, the therapeutic agent is teniposide, and the cancer is childhood acute lymphocytic leukemia (ALL), Hodgkin's lymphoma, certain brain tumors, and other types of cancer. In certain embodiments, the therapeutic agent is mitoxantrone, and the cancer is metastatic breast cancer, acute myeloid leukemia, non-Hodgkin's lymphoma, metastatic hormone-refractory prostate cancer, or multiple sclerosis (MS). In certain embodiments, the therapeutic agent is mitoxantrone, and the cancer is metastatic breast cancer, acute myeloid leukemia, non-Hodgkin's lymphoma, or metastatic hormone-refractory prostate cancer.

Characterization of Anti-Cancer Effects

When the pharmaceutical composition is being administered to a cancer patient in order to treat cancer, the therapeutic methods may be characterized according to the anti-cancer effect of the treatment, such as (i) a reduction in the size of at least one tumor in the patient, and/or (ii) reduction in the number of tumors in the patient.

Accordingly, in certain embodiments, the therapeutic method is characterized by at least a 20% reduction in the size of at least one tumor in the patient. In certain embodiments, there is at least a 35% reduction in the size of at least one tumor in the patient. In certain embodiments, there is at least a 50% reduction in the size of at least one tumor in the patient. In certain embodiments, there is at least a 60%, 70%, 80% or 90% reduction in the size of at least one tumor in the patient. In certain embodiments, there is about a 5%-50%, 10%-50%, 20%-50%, 5%-75%, 10%-75%, 20%-75%, or 50%-90% reduction in the size of at least one tumor in the patient.

When the cancer to be treated is a brain metastases, the method may be characterized according to the reduction in number and/or size of the brain metastases. In certain embodiments, there is at least a 20% reduction in the number of brain metastases in the patient. In certain embodiments, there is at least a 35% reduction in the number of brain metastases in the patient. In some embodiments, there is at least a 50% reduction in the number of brain metastases in the patient. In certain embodiments, there is at least a 60%, 70%, 80% or 90% reduction in the number of brain metastases in the patient. In certain embodiments, there is about a 5%-50%, 10%-50%, 20%-50%, 5%-75%, 10%-75%, 20%-75%, or 50%-90% reduction in the number of brain metastases in the patient.

In certain embodiments, the method provides statistically significant therapeutic effect in treating the cancer. In certain embodiments, the method provides a statistically significant increase in therapeutic effect for the treatment of the cancer, compared to that of patients receiving a direct administration of the same therapeutic agent at the same dose without being mixed with the blood product prior to administration.

In certain embodiments, the statistically significant therapeutic effect comprises overall survival (OS), progression-free survival (PFS), time to progression (TTP), time to treatment failure (TTF), event-free survival (EFS), time to next treatment (TTNT), objective response rate (ORR), duration of response (DoR), biomarker levels, reduced treatment cost, reduced cancer cell growth, apoptosis, and/or reduced migration and invasion. In certain embodiments, the statistically significant therapeutic effect has a p-value less than or equal to about 0.05.

Administration of Multiple Doses on Same Day

One or more doses of the pharmaceutical composition may be administered to a patient in a single day. For example, in certain embodiments, the blood product and therapeutic agent are mixed to provide a first pharmaceutical composition that is administered to the patient. Then, on the same day, a second pharmaceutical composition is administered to the patient, wherein the second pharmaceutical composition is formed by mixing the blood product and therapeutic agent. Administration of multiple doses of the pharmaceutical composition to the patient can be useful for administering larger quantities of therapeutic agent to the patient, particularly when it is not feasible to deliver all the desired quantity of therapeutic agent to the patient in the first pharmaceutical composition. Because there may be upper limits on the amount of therapeutic agent that can be mixed with the blood product (without causing undue adverse side effects, such as hemolysis of red blood cells), and it is generally preferred that administration of a composition containing a blood product should be performed promptly (e.g., within four hours after formation of a pharmaceutical composition containing a blood product), it can be preferable in some instances to prepare a first pharmaceutical composition which is administered to the patient, and then while administering the first pharmaceutical composition or after administration of the first pharmaceutical composition is complete, a second pharmaceutical composition is prepared, and the second pharmaceutical composition is administered to the patient after administration of the first pharmaceutical composition is complete.

Reduction in Toxicity of the Therapeutic Agent

When the pharmaceutical composition is being administered to a patient in order to treat cancer, the therapeutic methods may be characterized according to the reduction in toxicity of the therapeutic agent. Accordingly, in certain embodiments, toxicity of the therapeutic agent in the patient receiving the administration is reduced compared to that of patients receiving a direct administration of the same therapeutic agent at the same dose without being mixed with the blood product prior to administration. In certain embodiments, the toxicity is myelosuppression, hepatotoxicity, cardiotoxicity, neurotoxicity, mucocutaneous toxicity, skin toxicity, pulmonary toxicity, ocular toxicity, nephrotoxicity, vascular toxicity, pancreas toxicity, gastrointestinal toxicity, and/or genitourinary toxicity.

Exemplary Features of the Methods for Administering a Therapeutic Agent and Methods of Treating a Disease or Disorder Involving Infection The methods for administering a therapeutic agent and for treating a disease or disorder involving infection may be characterized by additional features, such as the type of disease or disorder involving infection, identity of the therapeutic agent, and other features as described in more detail herein.

Type of Disease or Disorder Involving Infection

The methods may be characterized according to the type of disease or disorder involving infection. Accordingly, in certain embodiments, the disease or disorder involving infection is sepsis. In certain embodiments, the disease or disorder involving infection is an infectious disease that affects macrophages. In certain embodiments, the infectious disease that affects macrophages is *Mycoplasma tuberculosis, Mycoplasma seprae*, leprosy, zika virus infection, Q fever, HIV, leishmaniasis, toxoplasmosis, babesia, or *Bartonella* infection.

In certain embodiments, the disease or disorder involving infection is a microbial infection. In certain embodiments, the microbial infection is a viral infection, a bacterial infection, a fungal infection, or a parasitic infection. In certain embodiments, the microbial infection is an infection with a virus, wherein the virus is hepatitis C virus, hepatitis B virus, hepatitis A virus, dengue virus, west nile virus, yellow fever virus, Japanese encephalitis virus, St. Louis encephalitis virus, human immunodeficiency virus (HIV), zika virus, Ebola virus, Marburg virus, chikungunya virus, Semliki forest virus, pichinde virus, influenza A virus, respiratory syncytial virus, vaccinia virus, herpes simplex virus type 1, herpes simplex virus type 2, human cytomegalovirus, rabies virus, paramyxovirus, varicella-zoster virus, human T cell lymphocytic virus, human herpes virus-6, human herpes virus-7, or human herpes virus-8.

In certain embodiments, the microbial infection is a bacterial infection. In certain embodiments, the microbial infection is an infection with a bacterial genus, wherein the bacterial genus is *Staphylococcus, Streptococcus, Pseudomonas, Escherichia, Salmonella, Helicobacter, Neisseria, Campylobacter, Chlamydia, Clostridium, Vibrio, Treponema, Escherichia coli, Mycobacterium, Klebsiella, Actinomyces, Bacterioides, Bordetella, Borrelia, Brucella, Corynebacterium, Diplococcus, Enterobacter, Fusobacterium, Leptospira, Listeria, Pasteurella, Proteus, Rickettsia, Shigella, Sphaerophorus, Acinetobacter, Aeromonas Burkholderia, Campylobacter, Corynebacterium, Enterococcus, Erwinia, Francisella, Haemophilus, Helicobacter, Legionella, Leptospira, Listeria, Mycoplasma, Neisseria, Veillonella, Vibrio, Coxiella* or *Yersinia*. In certain embodiments, the microbial infection is an infection with a bacterial genus, wherein the bacterial genus is *Pseudomonas, Salmonella, Staphylococcus, Streptococcus*, or *Treponema*. In certain embodiments, the microbial infection is an intracellular infection with a microbial species, wherein the microbial species is *Mycobacterium tuberculosis, Mycobacterium leprae, Mycobacterium bovis, Klebsiella pneumonia, Chlamydia muridarum, Chlamydia pneumonia, Burkholderia cenocepacia, Staphylococcus aureus, Coxiella burnetti*, or *Shigella flexneri*. In certain embodiments, the microbial infection is an infection with *Listeria monocytogenes, Pseudomonas aeruginosa, Serratia marcescens, Clostridium difficile, Staphylococcus aureus, E. coli, Streptococcus pneumoniae, Haemophilus influenzae*, or *Neisseria meningitide*.

In certain embodiments, the microbial infection is treatment-resistant. In certain embodiments, the microbial infection is antibiotic resistant. In certain embodiments, the antibiotic resistant microbial infection is methicillin-resistant *Staphylococcus aureus* (MRSA), vancomycin intermediate resistant *Staphylococcus aureus* (VISA), vancomycin resistant *Staphylococcus aureus* (VRSA), vancomycin-resistant Enterococci (VRE), antibiotic resistant *Neisseria gonorrhoeae*, carbapenem-resistant Enterobacteriaceae (CRE), VRE endocarditis, pan-resistant *Acinetobacter*, drug resistant *Escherichia coli*, chronic osteomyelitis, extensively drug resistant tuberculosis, Shiga toxin-producing *Escherichia coli*, antimicrobial-resistant sepsis, or multi-drug resistant *Pseudomonas*.

In certain embodiments, the microbial infection is a parasitic infection. In certain embodiments, the microbial infection is infection with a parasite genus, wherein the parasite genus is *Plasmodium, Toxoplasma, Neospora, Eimeria, Theileria, Cryptosporidium, Trypanosoma, Bartonella, Babesia*, or *Leishmania*. In certain embodiments, the microbial infection is *Toxoplasma gondii* infection or *Leishmania amazonensis* infection. In certain embodiments, the microbial infection is malaria.

In certain embodiments, the microbial infection is a fungal infection. In certain embodiments, the microbial infection is an infection with a fungus, wherein the fungus is *Candida, Mucorales, Aspergillus, Cryptococcus, Histoplasma*, or *Pneumocystis*. In certain embodiments, the microbial infection is infection with *Histoplasma capsulatum* or *Candida albicans*.

In certain embodiments, the disease or disorder involving infection is sepsis, and the therapeutic agent is a carbapenem antibiotic. In certain embodiments, the disease or disorder involving infection is sepsis, and the therapeutic agent is imipenem.

Identity of the Therapeutic Agent

The methods may be characterized according to the identity of the therapeutic agent. Accordingly, in certain embodiments, the therapeutic agent is an anti-microbial agent. In certain embodiments, the anti-microbial agent is an antibiotic, an antiviral agent, an anti-fungal agent, or an anti-parasitic agent. In certain embodiments, the anti-microbial agent is an antibiotic. In certain embodiments, the antibiotic is vancomycin. In certain embodiments, the antibiotic is a carbapenem antibiotic. In certain embodiments, the antibiotic is imipenem. In certain embodiments, the anti-microbial agent is an antiviral agent. In certain embodiments, the anti-microbial agent is an anti-fungal agent. In certain embodiments, the anti-microbial agent is an anti-parasitic agent. In certain embodiments, the anti-microbial agent is an anti-malarial agent. In certain embodiments, the anti-malarial agent is artemisinin, artesunate, quinine, quinidine, hydroxychloroquine, primaquine, lumefantrine, atovaquone, dapsone, proguanil, chloroquine, sulfadoxine-pyrimethamine, mefloquine, piperaquine, or amodiaquine. In certain embodiments, the anti-malarial agent is artemisinin. In certain embodiments, the therapeutic agent is for sepsis treatment (e.g., imipenem).

In certain embodiments, the antibiotic is aminoglycoside; amikacin; gentamicin; kanamycin; neomycin; netilmicin; steptomycin; tobramycin; ansamycin; geldanamycin; herbimycin; carbacephem; loracarbef; carbacepenem; ertapenem; doripenem; imipenem/cilastatin; meropenem; cephalosporin; cefadroxil; cefazolin; cefalotin or cefalothin; cefalexin; cefaclor; cefamandole; cefoxitin; cefprozil; cefuroxime; cefixime; cefdinir; cefditoren; cefoperazone; cefotaxime; cefpodoxime; ceftazidime; ceftibuten; ceftizoxime; ceftriaxone; cefepime; ceftobiprole; glycopeptide; teicoplanin; vancomycin; macrolides; azithromycin; clarithromycin; dirithromycin; erythromycin; roxithromycin; troleandomycin; telithromycin; spectinomycin; monobactam; aztreonam; penicillins; amoxicillin; ampicillin; azlocillin; carbenicillin; cloxacillin; dicloxacillin; flucloxacillin; mezlocillin; meticillin; nafcillin; oxacillin; penicillin, piperacillin, ticarcillin; bacitracin; colistin; polymyxin B; quinolone; ciprofloxacin; enoxacin; gatifloxacin; levofloxacin; lomefloxacin; moxifloxacin; norfloxacin; ofloxacin; trovafloxacin; sulfonamide; mafenide; prontosil; sulfacetamide; sulfamethizole; sufanilimide; sulfasalazine; sulfisoxazole; trimethoprim; trimethoprim-sulfamethoxazole (co-trimoxazole) (TMP-SMX); tetracycline; demeclocycline; doxycycline; minocycline; oxytetracycline; tetracycline; arsphenamine; chloramphenicol; clindamycin; lincomycin; ethambutol; fosfomycin; fusidic acid; furazolidone; isoniazid; linezolid; metronidazole; mupirocin; nitrofuantoin; platensimycin; purazinamide; quinupristin/dalfopristin; rifampin or rifampicin; tinidazole; or dapsone. In some embodiments, the antibiotic is Aclacinomycin A, Acylovir, Aklomide, Amantadine, Amikacin sulfate, Amoxicillin/clavulanate, Amprolium, Arbekacin, Atovaquone, Avermectin, Azathioprine, Azthromycin, Aztreinam, Bacampicilline-HCL, Arsphenamine, Bambermycin, Bialaphos, Bleomycin sulfate, Bradykinin antagonist, Carbadox, Carbarsone, Carbenicillin indanyl, Carboplatin, carminomycin, Clavulanic acid, Chloramphenicol, Clofazimine, Clopidol, Clotrimazole, Colistmethate sodium, colistin sulfate, cyclophosphamide, cycloserine, cyclospotin, cytaribine, Dactinomycin, Daunorubicin-HCL, Daunorubicin-liposomal, Demeclocycline-HCL, Docetaxel, Doxorubicin-HCL, Efrotomycin, Epirubicin, Ethambutol-HCL, Ethionamide, Etiposide, Famciclovir, Flomoxef, floxacillin, Fluconazole oral, Flucytosine, Fludarabine phosphate, Fluorouracil, Flurithromucin, Fluvastatin, Foscarnet sodium, Fosfomycin, Furazolidone, Ganciclovir sodium, Gentamycin sulfate, Gosserelin acetate, Gramicidin, Halofuginone HBr, Hygromycin B, Idarubicine-HCL, Idoxuridine Ifosfamide, Indinavir, Lincomycin, Ethambutol, Fosfomycin, Fusidic acid, Furazolidone, Isoniazid, Linezolid, Metronidazole, Mezlocillin sodium, Miconazole, Mibemectin, Milbemycins, Minocycline, Miocamycin, Mitomycin C, Mitotane, Mitoxantrone-HCl, Monensin sodium, Mupirocin, Nafcillin, Nalidixic acid, Narasin, Natamycin, Neomycin sulfate, Nevirapine, Nicarbazine, Niclosamide, Nisin, Nitrofurazone, Nitromide, Norfloxacin, Novobiocin sodium, Nystatin, Oleandomycin, Omeprazole, Oxiconazole nitrate, Oxytetracycline, Mupirocin, Nitrofurantoin, Paclitaxel, Pentamidine isethionate, Pentostatin, Phosphinothricin, Plicamycin, Pravastinamycin, Pyrantel tartrate, Pyrazinamide, Platensimycin, Pyrazinamide, Quinupristin/Dalfopristin, Rifampicin (Rifampin in US), Ribavirin, Sulfamethoxazole, Sulfanitran, Sulfathiazole, Sultamicillin, Tacrolimus (FK506), Taxobactam, Tenipocide, Terbinafine-HCl, Thiabendazole, Thiamphenicol, Thioguanine, Thiotepa, Tiamulin H-fumarate, Ticarcillin disodium, Tolnaftate, Topotecan, Trimetrexate glucuronate, troleandomycin, Tylosin phosphate, Tinidazole, Uracil mustard, Valacyclovir-HCl, Vancomycin-HCl, Vidarabene, Vinblastine sulfate, Vincristine sulfate, Vinorelbine tartrate, Virginiamycin, Zalcitabine, Zidovudine, or those described in in Strohl (Biotechnology of antibiotics, Informa Health Care, 1997, ISBN 0824798678, 9780824798673), Laskin et al. (Antibiotics, CRC Press, 1982, ISBN 0849372046, 9780849372049), Hash (Antibiotics, Academic Press, 1975, ISBN 0121819434, 9780121819439), and U.S. Pat. Nos. 5,998,581, 6,166,012, 6,218,138, 6,218,368, 6,224,864, 6,224,891, 6,287,813, 6,316,033, 6,331,540, 6,333,305, 6,337,410, 6,350,738, 6,352,983, 6,379,651, 6,380,172, 6,380,245, 6,380,356, 6,391,851, 6,399,086, 6,410,059, 6,437,119, 6,458,776, 6,462,025, 6,475,522, 6,486,148, 6,514,962, 6,518,243, 6,537,985, 6,544,502, 6,544,555, 6,551,591, 6,552,020, 6,565,882, 6,569,830, 6,586,393, 6,596,338, 6,599,885, 6,610,328, 6,623,757, 6,623,758, 6,623,931, 6,627,222, 6,630,135, 6,632,453, 6,638,532, 6,653,469, 6,663,890, 6,663,891, 6,667,042, 6,667,057, 6,669,842, 6,669,948, 6,716,962, 6,723,341, 6,727,232, 6,730,320, 6,747,012, 6,750,038, 6,750,199, 6,767,718, 6,767,904, 6,780,616, 6,780,639, 6,784,204, 6,784,283, 6,787,568, 6,821,959, 6,858,584, 6,861,230, 6,875,752, 6,913,764, 6,914,045, 6,921,810, 6,930,092, 6,942,993, 6,964,860, 6,974,585, 6,982,247, 6,991,807, 7,008,663, 7,018,996, 7,026,288, 7,030,093, 7,049,097, 7,067,483, 7,078,195, 7,078,377, 7,109,190, 7,115,576, 7,115,753, 7,122,204, 7,122,514, 7,138,487, 7,169,756, 7,202,339, 7,205,412, 7,211,417, 7,244,712, 7,271,147, 7,271,154, 7,273,723, 7,307,057, 7,385,101, 7,396,527, 7,407,654, 7,419,781, 7,485,294, 7,544,364, 7,569,677 or RE39743.

In certain embodiments, the antiviral agent is thiosemicarbazone; metisazone; nucleoside and/or nucleotide; acyclovir; idoxuridine; vidarabine; ribavirin; ganciclovir; famciclovir; valaciclovir; cidofovir; penciclovir; valganciclovir; brivudine; ribavirin, cyclic amines; rimantadine; tromantadine; phosphonic acid derivative; foscarnet; fosfonet; protease inhibitor; saquinavir; indinavir; ritonavir; nelfinavir; amprenavir; lopinavir; fosamprenavir; atazanavir; tipranavir; nucleoside and nucleotide reverse transcriptase inhibitor; zidovudine; didanosine; zalcitabine; stavudine; lamivudine; abacavir; tenofovir disoproxil; adefovir dipivoxil; emtricitabine; entecavir; non-nucleoside reverse transcriptase inhibitor; nevirapine; delavirdine; efavirenz;

neuraminidase inhibitor; zanamivir; oseltamivir; moroxydine; inosine pranobex; pleconaril; or enfuvirtide.

In certain embodiments, the anti-fungal agent is allylamine; terbinafine; antimetabolite; flucytosine; azole; fluconazole; itraconazole; ketoconazole; ravuconazole; posaconazole; voriconazole; glucan synthesis inhibitor; caspofungin; micafungin; anidulafungin; polyenes; amphotericin B; amphotericin B Lipid Complex (ABLC); amphotericin B Colloidal Dispersion (ABCD); liposomal amphotericin B (L-AMB); liposomal nystatin; or griseofulvin.

In certain embodiments, the anti-parasitic agent is eflornithine; furazolidone; melarsoprol; metronidazole; ornidazole; paromomycin sulfate; pentamidine; pyrimethamine; tinidazole; antimalarial agent; quinine; chloroquine; amodiaquine; pyrimethamine; sulphadoxine; proguanil; mefloquine; halofantrine; primaquine; artemesinin and derivatives thereof; doxycycline; clindamycin; benznidazole; nifurtimox; antihelminthic; albendazole; diethylcarbamazine; mebendazole; niclosamide; ivermectin; suramin; thiabendazole; pyrantel pamoate; levamisole; piperazine family; praziquantel; triclabendazole; octadepsipeptide; or emodepside.

Characterization of Therapeutic Effects

When the pharmaceutical composition is being administered to a patient in order to treat a disease or disorder involving infection, the therapeutic methods may be characterized according to the therapeutic effect of the treatment. For example, when the pharmaceutical composition is being administered to a patient in order to treat a microbial infection, the therapeutic method may be characterized according to the anti-microbial effect of the treatment, such as (i) reduction of mortality, and/or (ii) reduction in the level of microbes in the patient, as measured by any suitable marker. In certain embodiments, there is at least about 1%, 2%, 3%, 5%, 10%, 15%, 20%, 25%, 30%, 35%, 40%, 45%, 50%, 55%, 60%, 65%, 70%, 75%, 80%, 85%, 90%, 95%, 100%, 1.5 times, 2 times, 3 times, 4 times, 5 times, 10 times, 15 times, 20 times, 30 times, 40 times, 50 times, 60 times, 70 times, 80 times, 90 times, 100 times, or more, reduction of microbe level in the patient.

In certain embodiments, the method provides statistically significant therapeutic effect for the treatment of the disease or disorder involving infection. In certain embodiments, the method provides statistically significant therapeutic effect in treating a microbial infection. In certain embodiments, the method provides a statistically significant increase in therapeutic effect for the treatment of the disease or disorder involving infection, compared to that of patients receiving a direct administration of the same therapeutic agent at the same dose without being mixed with the blood product prior to administration.

In certain embodiments, the statistically significant therapeutic effect comprises reduced mortality rate, changes in biomarker levels, antibiotic- or organ-failure-free days, changes of microbial level, changes in white blood cells, reduced treatment cost, increased circulating half-life, shortened duration of symptoms, reduced opportunity of occurrence, reduced hospital stay time, ICU free days, duration of ventilation, and/or ventilation free days. In certain embodiments, the statistically significant therapeutic effect has a p-value less than or equal to about 0.05.

In certain embodiments, the methods provide statistically significant therapeutic effect in treating a severe infection, such as sepsis, endocarditis or osteomyelitis, an antibiotic-resistant infection, such as vancomycin resistant *Enterococcus* (VRE), methicillin resistant staph aureus (MRSA), or vancomycin resistant staph aureus (VRSA). In certain embodiments, the statistically significant therapeutic effect comprises 28-day overall mortality, over-all survival (OS), longer circulation half-life, event-free survival (EFS), changes in biomarker levels, increased circulating half-life, reduced treatment cost, shortened duration of symptoms, reduced opportunity of occurrence, reduced hospital stay time, ICU free days, duration of ventilation, and/or ventilation free days. In certain embodiments, biomarkers that can be used for efficacy analysis include, but are not limited to, bacterial levels, serum lactate levels, IL-6 levels, dopamine levels, plasma noradrenaline levels, central venous pressure, CVP, mean arterial pressure, MAP, and central venous oxygen saturation, ScvO2.

Reduction in Toxicity of the Therapeutic Agent

When the pharmaceutical composition is being administered to a patient in order to treat a disease or disorder involving infection, the therapeutic methods may be characterized according to the reduction in toxicity of the therapeutic agent. Accordingly, in certain embodiments, toxicity of the therapeutic agent in the patient receiving the administration is reduced compared to that of patients receiving a direct administration of the same therapeutic agent at the same dose without being mixed with the blood product prior to administration. In certain embodiments, the toxicity is diarrhea, upset stomach, allergy, yeast infection, anaphylaxis, skin toxicity, pulmonary toxicity, ototoxicity, myelosuppression, cardiotoxicity, neurotoxicity, and/or nephrotoxicity.

Exemplary Features of the Methods for Administering a Therapeutic Agent, Methods of Treating Cancer, and Methods of Treating a Disease or Disorder Involving Infection The methods described herein may be characterized by additional features, such as the method for preparation of the pharmaceutical composition, rate of infusion of the pharmaceutical composition, the concentration of therapeutic agent in the pharmaceutical composition, the identity of components in the pharmaceutical composition, the amount of whole blood in the pharmaceutical composition, the volume of pharmaceutical composition administered to patient, and/or other features as described in more detail herein.

Preparation of the Pharmaceutical Composition

The pharmaceutical composition (i.e., the pharmaceutical composition that comprises (i) a blood product and (ii) a therapeutic agent) may be prepared by mixing the blood product and therapeutic agent. The mixing may be performed under aerobic conditions or under anaerobic conditions. The condition may be characterized according to the whether the conditions are hypoxic or not hypoxic. The mixing may be performed at warm temperature (e.g., 37 degrees C.), room temperature, or at refrigerated conditions. In particular embodiments, the blood product is derived from the patient who is to receive the pharmaceutical composition containing the blood product and therapeutic agent.

The methods and the pharmaceutical composition can be characterized according to the duration of time between (i) mixing the blood product and therapeutic agent and (ii) the start of administration of the pharmaceutical composition to the patient. Such duration of time is known as the incubation time. The incubation time may be adjusted based on the identity of the therapeutic agent, with some therapeutic agents requiring a longer incubation time to provide a pharmaceutical composition having the best medicinal properties. Accordingly, in certain embodiments, the incubation time ranges from 1 minutes to 4 hours. In certain embodiments, the incubation time ranges from 1 minute to 1 hr, 1 minute to 5 minutes, 5 minutes to 10 minutes, 10 minutes to 15, 15 minutes to 20 minutes, 20 minutes to 25 minutes, 25 minutes to 30 minutes, 30 minutes to 35 minutes 35 minutes to 45 minutes, 45 minutes to 60 minutes, or 15 minutes to 30 minutes. In certain embodiments, the incubation time ranges from 30 minutes to 1 hr, 1 hr to 1.5 hrs, 2 hrs to 2.5 hrs, 2.5 hrs to 3 hrs, or longer. In certain embodiments, the incubation time is about 20 minutes.

In certain embodiments, the pharmaceutical composition is incubated after mixing before being administered to the patient for about 15 minutes, 20 minutes, 25 minutes, 30 minutes, 35 minutes, 40 minutes, 45 minutes, 50 minutes, 55 minutes, 60 minutes, 70 minutes, 80 minutes, 90 minutes, 100 minutes, 110 minutes, 120 minutes, 150 minutes, 180 minutes, 210 minutes, 240 minutes, or more at a temperature that ranges from about 18° C. to about 25° C., such as about 18° C., 19° C., 20° C., 21° C., 22° C., 23° C., 24° C., 25° C., 26° C., or more. In certain embodiments, the pharmaceutical composition is incubated for about 30 minutes to about 240 minutes at a temperature that ranges from about 18° C. to about 25° C. after mixing before being administered to the patient. In certain embodiments, the pharmaceutical composition is incubated after mixing before being administered to the patient at a lower temperature for longer time, such as for over 1, 2, 3, 4, 5, 6 hours or more at a temperature that ranges from 2° C. to about 4° C. In certain embodiments, the pharmaceutical composition is incubated for over 4 hours at a refrigerated condition. In certain embodiments, the pharmaceutical composition is incubated after mixing before being administered to the patient at a higher temperature for a shorter time, such as for up to about 1, 2, 5, 10, 15, 20, 30, 45, or 60 minutes at a temperature that ranges from 25° C. to about 40° C. In certain embodiments, the pharmaceutical composition is incubated for up to about 60 minutes at about 37° C., after mixing before being administered to the patient.

In certain embodiments, the pharmaceutical composition is irradiated by UV light before being administered to the patient. In certain embodiments, the blood product is irradiated before, during, or after mixing with the therapeutic agent for about 1 minute to about 60 minutes, such as about 5-30 minutes with UVA light and/or UVB light. In some embodiments, the light is a LED light or a bulb. In some embodiments, the light shines through a reservoir of the blood product before, during, or after mixing. Without wishing to be bound by any particular theory, UV light may both sterilize the blood and oxidize the blood components, such as erythrocytes, making them more "sticky" on hypoxic vasculature, which is present on or in tumors, abscesses, and granulomas.

In certain embodiments, the pharmaceutical composition can include an anti-oxidant. Exemplary anti-oxidants include glutathione, N-acetyl-cysteine, α-lipoid acid, vitamin A, vitamin C, and vitamin E. The anti-oxidant can be present in an amount sufficient to prevent oxidation of the blood product or its components such as red blood cells. For example, vitamin C can be present in a pharmaceutical composition in an amount between about 250 mg to about 1000 mg. In some embodiments, the pharmaceutical composition can include a bisphosphonate. Instead of or in addition to an anti-oxidant or a bisphosphonate being present in the pharmaceutical composition, a patient for whom the methods of the present invention are intended may have the anti-oxidant or the bisphosphonate present systemically, for example, via a separate administration. Without wishing to be bound by any particular theory, the presence of an anti-oxidant can prevent the oxidation of the blood product (e.g., red blood cells) thereby preventing monocytes/macrophages from engulfing the oxidized blood product or component, which engulfment would take the oxidized blood product or its components and possibly the therapeutic agent out of circulation before reaching their intended target. Again without wishing to be bound by any particular theory, the presence of a bisphosphonate can inhibit monocytes/macrophages from engulfing oxidized blood product or its components and possibly the therapeutic agent thereby permitting the therapeutic agent to reach its intended target.

Rate of Infusion of Pharmaceutical Composition

The methods may be characterized according to the rate at which the pharmaceutical composition is administered to the patient. Accordingly, in certain embodiments, the pharmaceutical composition is intravenously administered to the patient at a rate of at least 30 mL/hour. In certain embodiments, the pharmaceutical composition is intravenously administered to the patient at a rate of at least 60 mL/hour. In certain embodiments, the pharmaceutical composition is intravenously administered to the patient at a rate of at least 90 mL/hour. In certain embodiments, the pharmaceutical composition is intravenously administered to the patient at a rate of at least 120 mL/hour. In some embodiments, the pharmaceutical composition is intravenously administered to the patient at a rate of at least 150 mL/hour, 180 mL/hour, 210 mL/hour, 240 mL/hour, 270 mL/hour, 300 mL/hour, 330 mL/hour, or 360 mL/hour. In some embodiments, the pharmaceutical composition is intravenously administered to the patient at a rate in the range of from about 100 mL/hour to about 150 mL/hour, from about 150 mL/hour to about 200 mL/hour, from about 180 mL/hour to about 220 mL/hour, from about 200 mL/hour to about 250 mL/hour, from about 250 mL/hour to about 300 mL/hour, from about 275 mL/hour to about 325 mL/hour, or from about 300 mL/hour to about 350 mL/hour.

Concentration of Therapeutic Agent in the Pharmaceutical Composition

The methods may be characterized according to the concentration of therapeutic agent in the pharmaceutical composition. Accordingly, in certain embodiments, the pharmaceutical composition contains at least one therapeutic agent at a concentration of at least 10 µg/mL. In certain embodiments, the pharmaceutical composition contains at least one therapeutic agent at a concentration of at least 20 µg/mL. In certain embodiments, the pharmaceutical composition contains at least one therapeutic agent at a concentration of at least 50 µg/mL. In certain embodiments, the pharmaceutical composition contains at least one therapeutic agent at a concentration of at least 100 µg/mL. In certain embodiments, the pharmaceutical composition contains at least one therapeutic agent at a concentration of at least 150 µg/mL. In certain embodiments, the pharmaceutical composition contains at least one therapeutic agent at a concentration in the range of about 10 µg/mL to about 1 mg/mL. In certain embodiments, the pharmaceutical composition contains at least one therapeutic agent at a concentration in the range of about 10 µg/mL to about 0.5 mg/mL. In certain embodiments, the pharmaceutical composition contains at least one therapeutic agent at a concentration in the range of about 10 µg/mL to about 250 µg/mL. In certain embodiments, the pharmaceutical composition contains at least one therapeutic agent at a concentration in the range of about 20 µg/mL to about 200 µg/mL. In certain embodiments, the pharmaceutical composition contains at least one therapeutic agent at a concentration in the range of about 200 µg/mL to about 750 µg/mL. In certain embodiments, the pharmaceutical composition contains at least one therapeutic agent at a concentration in the range of about 200 µg/mL to about 400 µg/mL, about 400 µg/mL to about 600 µg/mL, about 500 µg/mL to about 700 µg/mL, or about 600 µg/mL to about 700 µg/mL. In certain embodiments, the pharmaceutical composition contains the therapeutic agent at a concentration in the range of about 1 µg/mL to about 10 µg/mL, about 10 µg/mL to about 50 µg/mL, about 50 µg/mL to about 100 µg/mL, about 100 µg/mL to about 200 µg/mL, 200 µg/mL to about 400 µg/mL, about 400 µg/mL to about 600 µg/mL, about 500 µg/mL to about 700 µg/mL, about 600 µg/mL to about 700 µg/mL, about 700 µg/mL to about 900 µg/mL, about 900 µg/mL to about 1100 µg/mL, about 1100 µg/mL to about 1500 µg/mL, about 1500 µg/mL to about 2000 µg/mL, or about 2000 µg/mL to about 2500 µg/mL.

The concentration of the therapeutic agent may depend upon the choice of therapeutic agent. Accordingly, in certain embodiments when the pharmaceutical composition comprises a therapeutic agent that is topotecan or irinotecan, the pharmaceutical composition can contain a concentration of the therapeutic agent of at least 0.1 µg/mL, at least 0.5 µg/mL, at least 1 µg/mL, at least 1.5 µg/mL, at least 2 µg/mL, at least 2.5 µg/mL, at least 3 µg/mL, at least 3.5 µg/mL, at least 4 µg/mL, at least 4.5 µg/mL, at least 5 µg/mL, at least 5.5 µg/mL, at least 6 µg/mL, at least 6.5 µg/mL, at least 7 µg/mL, at least 7.5 µg/mL, at least 8 µg/mL, at least 8.5 µg/mL, at least 9 µg/mL, at least 10 µg/mL, at least 15 µg/mL, at least 20 µg/mL, at least 30 µg/mL, at least 40 µg/mL, at least 50 µg/mL, at least 60 µg/mL, at least 70 µg/mL, at least 80 µg/mL, at least 90 µg/mL, at least 100 µg/mL, at least 110 µg/mL, at least 120 µg/mL, at least 130 µg/mL, at least 140 µg/mL, at least 150 µg/mL, at least 160 µg/mL, at least 170 µg/mL, at least 180 µg/mL, at least 190 µg/mL, at least 200 µg/mL, at least 250 µg/mL, at least 300 µg/mL, at least 300 µg/mL, at least 300 µg/mL, at least 300 µg/mL, at least 300 µg/mL, or more, inclusive of all ranges and subranges therebetween. In certain embodiments, the pharmaceutical composition can contain a topotecan concentration of at least 0.5 µg/mL. In certain embodiments, the pharmaceutical composition can contain an irinotecan concentration of at least 2.8 µg/mL.

In certain embodiments when the pharmaceutical composition comprises a therapeutic agent that is doxorubicin, paclitaxel, or cisplatin, the pharmaceutical composition can contain a concentration of the therapeutic agent of at least 0.5 µg/mL, at least 1 µg/mL, at least 1.5 µg/mL, at least 2 µg/mL, at least 2.5 µg/mL, at least 3 µg/mL, at least 3.5 µg/mL, at least 4 µg/mL, at least 4.5 µg/mL, at least 5 µg/mL, at least 5.5 µg/mL, at least 6 µg/mL, at least 6.5 µg/mL, at least 7 µg/mL, at least 7.5 µg/mL, at least 8 µg/mL, at least 8.5 µg/mL, at least 9 µg/mL, at least µg/mL, or more, inclusive of all ranges and subranges therebetween. In certain embodiments, the pharmaceutical composition can contain a doxorubicin concentration of at least 1 µg/mL. In certain embodiments, the pharmaceutical composition can contain a paclitaxel concentration of at least 1.2 µg/mL. In certain embodiments, the pharmaceutical composition can contain a cisplatin concentration of at least 1 µg/mL.

In certain embodiments when the pharmaceutical composition comprises a therapeutic agent that is ifosfamide or cyclophosphamide, the pharmaceutical composition can contain a concentration of the therapeutic agent of at least 0.1 µg/mL, at least 0.5 µg/mL, at least 1 µg/mL, at least 2 µg/mL, at least 3 µg/mL, at least 4 µg/mL, at least 5 µg/mL, at least 6 µg/mL, at least 7 µg/mL, at least 8 µg/mL, at least 9 µg/mL, at least 10 µg/mL, at least 11 µg/mL, at least 12 µg/mL, at least 13 µg/mL, at least 14 µg/mL, at least 15 µg/mL, at least 16 µg/mL, at least 17 µg/mL, at least 18 µg/mL, at least 19 µg/mL, at least 20 µg/mL, at least 21 µg/mL, at least 22 µg/mL, at least 23 µg/mL, at least 24 µg/mL, at least 25 µg/mL, or more, inclusive of all ranges and subranges therebetween. In certain embodiments, the pharmaceutical composition can contain an ifosfamide concentration of at least 20 µg/mL. In certain embodiments, the pharmaceutical composition can contain a cyclophosphamide concentration of at least 20 µg/mL.

In certain embodiments when the pharmaceutical composition comprises a therapeutic agent that is carboplatin or oxaliplatin, the pharmaceutical composition can contain a concentration of the therapeutic agent of at least 0.5 µg/mL, at least 1 µg/mL, at least 1.5 µg/mL, at least 2 µg/mL, at least 2.5 µg/mL, at least 3 µg/mL, at least 3.5 µg/mL, at least 4 µg/mL, at least 4.5 µg/mL, at least 5 µg/mL, at least 5.5 µg/mL, at least 6 µg/mL, at least 6.5 µg/mL, at least 7 µg/mL, at least 7.5 µg/mL, at least 8 µg/mL, at least 8.5 µg/mL, at least 9 µg/mL, at least 10 µg/mL, at least 15 µg/mL, at least 20 µg/mL, at least 30 µg/mL, at least 40 µg/mL, at least 50 µg/mL, at least 60 µg/mL, at least 70 µg/mL, at least 80 µg/mL, at least 90 µg/mL, at least 100 µg/mL, or more, inclusive of all ranges and subranges therebetween. In certain embodiments, the pharmaceutical composition can contain a cisplatin concentration of at least 1 µg/mL. In certain embodiments, the pharmaceutical composition can contain an oxaliplatin concentration of at least 1 µg/mL.

In certain embodiments when the pharmaceutical composition comprises a therapeutic agent that is digoxin or vancomycin, the pharmaceutical composition can contain a concentration of the therapeutic agent of at least 0.1 µg/mL, at least 0.5 µg/mL, at least 1 µg/mL, at least 1.5 µg/mL, at least 2 µg/mL, at least 2.5 µg/mL, at least 3 µg/mL, at least 3.5 µg/mL, at least 4 µg/mL, at least 4.5 µg/mL, at least 5 µg/mL, at least 5.5 µg/mL, at least 6 µg/mL, at least 6.5 µg/mL, at least 7 µg/mL, at least 7.5 µg/mL, at least 8 µg/mL, at least 8.5 µg/mL, at least 9 µg/mL, at least µg/mL, at least 15 µg/mL, at least 20 µg/mL, at least 25 µg/mL, at least 30 µg/mL, at least 35 µg/mL, at least 40 µg/mL, at least 45 µg/mL, at least 50 µg/mL, or more.

In certain embodiments when the pharmaceutical composition comprises a therapeutic agent that is imipenem, the pharmaceutical composition can contain a concentration of the therapeutic agent of at least 10 µg/mL, at least 50 µg/mL, at least 100 µg/mL, at least 150 µg/mL, at least 200 µg/mL, at least 250 µg/mL, at least 300 µg/mL, at least 350 µg/mL, at least 350 µg/mL, at least 400 µg/mL, at least 450 µg/mL, at least 500 µg/mL, at least 550 µg/mL, at least 600 µg/mL, at least 650 µg/mL, at least 700 µg/mL, at least 750 µg/mL, at least 800 µg/mL, at least 850 µg/mL, at least 900 µg/mL, at least 950 µg/mL, at least 1000 µg/mL, or more.

Anticoagulant

The methods may be characterized according to the identity and/or amount of the anticoagulant. Accordingly, in certain embodiments, the pharmaceutical composition comprises an anticoagulant. In certain embodiments, the anticoagulant comprises one or more of heparin and a citrate salt. In certain embodiments, the anticoagulant is present in the pharmaceutical composition in an amount ranging from about 0.1% wt/wt to about 15% wt/wt. In certain embodiments, the anticoagulant is present in the pharmaceutical composition in an amount ranging from about 1% wt/wt to about 10% wt/wt. In certain embodiments, the anticoagulant is present in the pharmaceutical composition in an amount ranging from about 2% wt/wt to about 8% wt/wt. In certain embodiments, the pharmaceutical composition consists essentially of the blood product, the therapeutic agent, and an anticoagulant.

Osmolality Adjusting Agent and/or Excipient

The methods may be characterized according to the identity and/or amount of an osmolality adjusting agent. Accordingly, in certain embodiments, the pharmaceutical composition contains an osmolality adjusting agent to increase the osmolality. In certain embodiments, the osmolality adjusting agent is sodium chloride.

The methods may be characterized according to the identity and/or amount of an excipient. Accordingly, in certain embodiments, the pharmaceutical composition contains an excipient. In certain embodiments, the excipient is N-methyl-2-pyrrolidone, dimethylacetamide, dimethylsulfoxide (DMSO), glycerol, urea, water, propylene glycol, urea, ethanol, Cremophor EL, Cremophor RH 40, Cremophor RH 60, d-alpha-tocopherol polyethylene glycol 1000 succinate, polysorbate 20, polysorbate 80, Solutol HS 15, sorbitan monooleate, poloxamer 407, Labrafil M-1944CS, Labrafil M-2125CS, Labrasol, Gellucire 44/14, Softigen 767, and mono- and di-fatty acid esters of PEG 300, 400, or 1750, glyceryl monooleate, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil and palm seed oil, beeswax, d-alpha-tocopherol, oleic acid, medium-chain mono- and diglycerides, hydrogenated soy phosphatidylcholine, distearoylphosphatidylglycerol, L-alpha-dimyristoylphosphatidylcholine, and/or L-alpha-dimyristoylphosphatidylglycerol.

Amount of Blood Product in the Pharmaceutical Composition

The methods may be characterized according to the amount of blood product (e.g., whole blood) in the pharmaceutical composition. Accordingly, in certain embodiments, the blood product constitutes at least 30% wt/wt of the pharmaceutical composition. In certain embodiments, the blood product constitutes at least 40% wt/wt of the pharmaceutical composition. In certain embodiments, the blood product constitutes at least 50% wt/wt of the pharmaceutical composition. In certain embodiments, the blood product constitutes at least 60% wt/wt of the pharmaceutical composition. In certain embodiments, the blood product constitutes at least 75% wt/wt of the pharmaceutical composition. In certain embodiments, the blood product constitutes at least 90% wt/wt of the pharmaceutical composition.

In certain embodiments, the blood product constitutes from about 30% wt/wt to about 99.99% wt/wt of the pharmaceutical composition. In certain embodiments, the blood product constitutes from about 30% wt/wt to about 99.9% wt/wt of the pharmaceutical composition. In certain embodiments, the blood product constitutes from about 60% wt/wt to about 99% wt/wt of the pharmaceutical composition. In certain embodiments, the blood product constitutes from about 70% wt/wt to about 98% wt/wt of the pharmaceutical composition. In certain embodiments, the blood product constitutes from about 70% wt/wt to about 95% wt/wt of the pharmaceutical composition. In certain embodiments, the blood product constitutes from about 75% wt/wt to about 90% wt/wt of the pharmaceutical composition. In certain embodiments, the blood product constitutes from about 80% wt/wt to about 98% wt/wt of the pharmaceutical composition.

In certain embodiments, the blood product constitutes about 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, 99.91%, 99.92%, 99.93%, 99.94%, 99.95%, 99.96%, 99.97%, 99.98%, 99.99%, or more, by weight of the pharmaceutical composition.

In certain embodiments, there is from about 1 mL to about 100 mL of blood product in the pharmaceutical composition. In certain embodiments, there is from about 1 mL to about 25 mL of blood product in the pharmaceutical composition. In certain embodiments, there is from about 25 mL to about 50 mL of blood product in the pharmaceutical composition. In certain embodiments, there is from about 50 mL to about 75 mL of blood product in the pharmaceutical composition. In certain embodiments, there is from about 75 mL to about 100 mL of blood product in the pharmaceutical composition.

In certain embodiments, there is from about 5 mL to about 10 mL of blood product in the pharmaceutical composition, from about 10 mL to about 15 mL of blood product in the pharmaceutical composition, from about 9 mL to about 11 mL of blood product in the pharmaceutical composition, from about 10 mL to about 20 mL of blood product in the pharmaceutical composition, from about 20 mL to about 30 mL of blood product in the pharmaceutical composition, from about 30 mL to about 50 mL of blood product in the pharmaceutical composition, from about 50 mL to about 70 mL of blood product in the pharmaceutical composition, or from about 70 mL to about 90 mL of blood product in the pharmaceutical composition. In certain embodiments, there is from about 90 mL to about 110 mL of blood product in the pharmaceutical composition. In certain embodiments, there is from about 95 mL to about 105 mL of blood product in the pharmaceutical composition. In certain embodiments, there is about 100 mL of blood product in the pharmaceutical composition. In certain embodiments, there is about 150 mL, about 200 mL, about 250 mL, about 300 mL, about 350 mL, about 400 mL, about 450 mL, about 500 mL, or more of blood product in the pharmaceutical composition. In certain embodiments, there is about 100 mL to about 500 mL of blood product in the pharmaceutical composition.

In certain embodiments, whole blood constitutes at least 30% wt/wt of the pharmaceutical composition. In certain embodiments, whole blood constitutes at least 40% wt/wt of the pharmaceutical composition. In certain embodiments, whole blood constitutes at least 50% wt/wt of the pharmaceutical composition. In certain embodiments, whole blood constitutes at least 60% wt/wt of the pharmaceutical composition. In certain embodiments, whole blood constitutes at least 75% wt/wt of the pharmaceutical composition. In certain embodiments, whole blood constitutes at least 90% wt/wt of the pharmaceutical composition. In certain embodiments, whole blood constitutes from about 60% wt/wt to about 99% wt/wt of the pharmaceutical composition. In certain embodiments, whole blood constitutes from about 70% wt/wt to about 95% wt/wt of the pharmaceutical composition. In certain embodiments, whole blood constitutes from about 75% wt/wt to about 90% wt/wt of the pharmaceutical composition. In certain embodiments, there is from about 5 mL to about 10 mL of whole blood in the pharmaceutical composition, from about 10 mL to about 15 mL of whole blood in the pharmaceutical composition, from about 9 mL to about 11 mL of whole blood in the pharmaceutical composition, from about 10 mL to about 20 mL of whole blood in the pharmaceutical composition, from about 20 mL to about 30 mL of whole blood in the pharmaceutical composition, from about 30 mL to about 50 mL of whole blood in the pharmaceutical composition, from about 50 mL to about 70 mL of whole blood in the pharmaceutical composition, or from about 70 mL to about 90 mL of whole blood in the pharmaceutical composition. In certain embodiments, there is from about 90 mL to about 110 mL of whole blood in the pharmaceutical composition. In certain embodiments, there is from about 95 mL to about 105 mL of whole blood in the pharmaceutical composition. In certain embodiments, there is about 100 mL of whole blood in the pharmaceutical composition.

In certain embodiments, whole blood is present in the pharmaceutical composition in an amount of from about 2-15 mL of whole blood per kg of the patient's weight. In certain embodiments, whole blood is present in the pharmaceutical composition in an amount of from about 5-10 mL of whole blood per kg of the patient's weight. In certain embodiments, whole blood is present in the pharmaceutical composition in an amount of from about 10-15 mL of whole blood per kg of the patient's weight.

Volume of Pharmaceutical Composition Administered to Patient

The methods may be characterized according to the volume of pharmaceutical composition administered to the patient. Accordingly, in certain embodiments, the pharmaceutical composition has a volume in the range of about 1 mL to about 200 mL. In certain embodiments, the pharmaceutical composition has a volume in the range of about 1 mL to about 100 mL. In certain embodiments, the pharmaceutical composition has a volume in the range of about 10 mL to about 15 mL, about 15 mL to about 20 mL, about 20 mL to about 30 mL, or about 30 mL to about 50 mL. In certain embodiments, the pharmaceutical composition has a volume in the range of about 1 mL to about 100 mL. In certain embodiments, the pharmaceutical composition has a volume in the range of about 1 mL to about 25 mL. In certain embodiments, the pharmaceutical composition has a volume in the range of about 25 mL to about 50 mL. In certain embodiments, the pharmaceutical composition has a volume in the range of about 50 mL to about 75 mL. In certain embodiments, the pharmaceutical composition has a volume in the range of about 75 mL to about 100 mL. In certain embodiments, the pharmaceutical composition has a volume in the range of about 100 mL to about 125 mL. In certain embodiments, the pharmaceutical composition has a volume in the range of about 125 mL to about 150 mL, about 150 mL to about 200 mL, about 200 mL to about 250 mL, about 300 mL to about 350 mL, about 350 mL to about 450 mL, or about 450 mL to about 500 mL. In certain embodiments, the pharmaceutical composition has a volume of about 500 mL, about 600 mL, about 700 mL, about 800 mL, about 900 mL, about 1000 mL, or more.

Timeline for Administering the Pharmaceutical Composition

The methods may be characterized according to the timeline for administering the pharmaceutical composition to the patient. Accordingly, in certain embodiments, intravenous administration of the pharmaceutical composition commences within about 1 hour after formation of the pharmaceutical composition. In certain embodiments, intravenous administration of the pharmaceutical composition commences within about 30 minutes after formation of the pharmaceutical composition. In certain embodiments, intravenous administration of the pharmaceutical composition commences within about 20 minutes after formation of the pharmaceutical composition. In certain embodiments, intravenous administration of the pharmaceutical composition is complete within about 6 hours after formation of the pharmaceutical composition. In certain embodiments, intravenous administration of the pharmaceutical composition is complete within about 4 hours after formation of the pharmaceutical composition.

Obtaining Whole Blood for the Pharmaceutical Composition

The methods may comprise obtaining an aliquot of whole blood from the patient, and then using said aliquot to prepare the pharmaceutical composition for administration to the patient.

Location of Intravenous Administration

The methods may be characterized according to the location of intravenous administration to the patient. In certain embodiments, the intravenous administration is central intravenous administration. In certain embodiments, the intravenous administration is peripheral intravenous administration.

Patients for Treatment

The therapeutic methods may be characterized according to the patient to be treated. In certain embodiments, the patient is an adult human. In certain embodiments, the patient is a pediatric human.

In certain embodiments, the patient does not suffer from anemia or have reduced blood volume. In certain embodiments, the patient has at least 95% of the amount of their average daily blood volume.

In certain embodiments, the patient is immuno-deficient, e.g., the patient has reduced capacity to fight infectious disease, or has reduced capacity to respond to pathogen exposure. In some embodiments, the patient is a leukemic or neutropenic patient, a patient on hemodialysis, patient receiving immunosuppressant therapy, an AIDS patient, a diabetic patient, or a patient receiving chemotherapy or radiation therapy for cancer. In certain embodiments, the patient has immunodeficiency caused by a genetic defect, malnutrition, drug abuse, alcoholism, and/or another immunocompromising illness or condition. In certain embodiments, the patient is over the age of 50, 55, 60, 65, 70, 75, 80, 85, 90, or older. In certain embodiments, the patient is a newborn.

In certain embodiments, the patient has sepsis, or is at risk of getting sepsis. In certain embodiments, the sepsis is severe sepsis or septic shock. In certain embodiments, the infection is associated with sepsis, severe sepsis or septic shock. In certain embodiments, the patient is scheduled for an invasive surgical procedure that may lead to sepsis.

In certain embodiments, the patient is an animal. In certain embodiments, the animal is a companion animal or a farm animal. In certain embodiments, the animal is a companion animal.

In certain embodiments, the companion animal is a dog, a cat, or a bird. In certain embodiments, the animal is a farm animal. In certain embodiments, the farm animal is a horse, a goat, a sheep, a swine, or a cattle.

Determination of Statistically Significant Therapeutic Effect

In some embodiments, methods of the present invention provide a statistically significant therapeutic effect for the treatment of a condition. In certain embodiments, the statistically significant therapeutic effect is determined based on one or more standards or criteria provided by one or more regulatory agencies in the United States, e.g., FDA or other countries. In various embodiments, the statistically significant therapeutic effect is determined based on results obtained from regulatory agency approved clinical trial set up and/or procedure.

In some embodiments, the statistically significant therapeutic effect is determined based on a patient population of at least 300, 400, 500, 600, 700, 800, 900, 1000 or 2000. In some embodiments, the statistically significant therapeutic effect is determined based on data obtained from randomized and double-blinded clinical trial set up. In some embodiments, the statistically significant therapeutic effect is determined based on data with a p value of less than or equal to about 0.05, 0.04, 0.03, 0.02 or 0.01. In some embodiments, the statistically significant therapeutic effect is determined based on data with a confidence interval greater than or equal to 95%, 96%, 97%, 98% or 99%. In some embodiments, the statistically significant therapeutic effect is determined on approval of Phase III clinical trial of the methods provided by the present invention, e.g., by FDA in the US.

In general, statistical analysis can include any suitable method permitted by a regulatory agency, e.g., FDA in the US or China or any other country. In some embodiments, statistical analysis includes non-stratified analysis, log-rank analysis, e.g., from Kaplan-Meier, Jacobson-Truax, Gulliken-Lord-Novick, Edwards-Nunnally, Hageman-Arrindel and Hierarchical Linear Modeling (HLM) and Cox regression analysis.

Reduction in Side Effects of the Therapeutic Agent

A therapeutic agent may cause significant side effects or toxicity when administered to the patient at a therapeutically effective dose, without the blood mix of the present invention. Methods of the present invention can provide improved efficacy and/or reduced toxicity when a therapeutic agent is administered to a patient by a blood-based delivery. Therefore, with the present invention, a therapeutic agent can be administered to a patient in a blood mix at a higher, more therapeutically effective dose, but still has comparable or reduced toxicity compared to the situation where the therapeutic agent is administered to the patient without the blood mix.

Accordingly, in certain embodiments, the patient has reduced incidence and/or severity of side effects compared to patients receiving a direct administration of the same therapeutic agent at the same dose without being mixed with the blood product prior to administration. In certain embodiments, the patient has reduced side effects compared to patients receiving a direct administration of the same therapeutic agent at the same dose without being mixed with the blood product prior to administration. In certain embodiments, the dose of the therapeutic agent in the pharmaceutical composition is at least about 10% to about 300% more than the dose recommended for a direct administration of the same therapeutic agent without being mixed with the blood product prior to administration. In certain embodiments, the dose of the therapeutic agent in the pharmaceutical composition is at least 1%, at least 5%, at least 10%, at least 20%, at least 30%, at least 40%, at least 50%, at least 60%, at least 70%, at least 80%, at least 90%, at least 100%, at least 200%, at least 300%, at least 400%, at least 500%, at least 600%, at least 700%, at least 800%, at least 900%, at least 1000%, or higher, inclusive of all ranges and subranges therebetween, more than the dose recommended for a direct administration of the same therapeutic agent without being mixed with the blood product prior to administration.

In certain embodiments, the therapeutic agent has a longer circulating half-life in the patient compared to direct administration of the same therapeutic agent at the same dose without being mixed with the blood product prior to administration. In certain embodiments, the circulating half-life of the therapeutic agent is at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 100%, 110%, 110%, 120%, 130%, 140%, 150%, 160%, 170%, 180%, 190%, 200%, 250%, 300%, 350%, 400%, 450%, 500%, 600%, 700%, 800%, 900%, 1000%, or more, longer than the circulating half-life of the same therapeutic agent at the same dose without being mixed with the blood product before administration.

In certain embodiments, the method protects normal tissues in the patient in the form of chemoprotection, radioprotection or radiochemoprotection, compared to patients receiving a direct administration of the same therapeutic agent at the same dose without being mixed with the blood product prior to administration. In certain embodiments, the method protects normal tissues in the patient in the form of chemoprotection, compared to patients receiving a direct administration of the same therapeutic agent at the same dose without being mixed with the blood product prior to administration. In certain embodiments, use of a therapeutic agent mixed with a blood product prior to administration results in protection of normal tissues in the form of chemoprotection, radioprotection or radiochemoprotection. In certain embodiments, use of a therapeutic agent mixed with a blood product prior to administration results in protection of normal tissues in the form of chemoprotection.

In some embodiments, the side effects/toxicities include, but are not limited to, pulmonary toxicity (e.g., interstitial infiltrates, noncardiogenic pulmonary edema, pulmonary hemorrhage), cardiovascular toxicity (e.g., cardiac, hypertension), vascular toxicity (e.g., arteriothromboembolic, venous, pericardial effusions), hepatotoxicity (e.g., fatty liver, veno-occlusive disease, pseudocirrhosis, bilary stricture), pancreas toxicity, pancreatitis toxicity, gastrointestinal toxicity (e.g., enteritis, neutropenic colitis, pneumatosis or perforation, megacolon), genitourinary toxicity (e.g., hemorrhagic cystitis, neurogenic bladder), peritoneum, mesentery, or soft tissues toxicity (e.g., ascites), and neurologic toxicity (e.g., peripheral neuropathy, central nervous system), ocular toxicity, and ototoxicity (e.g. hearing loss).

In some embodiments, the side effect is pulmonary toxicity. The toxicity can be detected and measured by any suitable method. In some embodiments, the toxicity is rated by histology, high-resolution computed tomography (HRCT), 18F-fluorodeoxyglucose positron emission tomography, serum markers (KL-6, ADAM8), bronchoscopy and bronchoalveolar lavage (BAL).

In some embodiments, the side effect is cardiotoxcity. The toxicity can be detected and measured by any suitable method. In some embodiments, the toxicity is rated by left ventricular ejection fraction (LVEF), and molecular markers, such as cardiac troponins, natriuretic peptides, heart-type fatty acid-binding protein, glycogen phosphorylase isoenzyme BB, C-reactive protein, myeloperoxidase, and nitric oxide, see Tian et al. (2014, Front Oncol. 2014; 4: 277).

In some embodiments, the side effect is vascular toxicity. The toxicity can be detected and measured by any suitable method. In some embodiments, the toxicity may include, but is not limited to, hypertension (high blood pressure), pulmonary hypertension, venous spasm (e.g., Raynaud's disease) and acute arterial ischemic events, e.g., myocardial infarction and cerebrovascular accidents. Methods to diagnose and monitor, depending on the symptoms/signs and risk factors, may include EKGs, echocardiograms, periodic lipid profiling and blood glucose examinations, as well as blood pressure monitoring. In some embodiments, the toxicity is rated by histopathology (e.g., histomorphologic lexicon, endothelium, degeneration/apoptosis/necrosis, endothelium, hypertrophy/hyperplasia, vacular smooth muscle cell hyalinization, vascular smooth muscle apoptosis/necrosis, vascular smooth muscle hypertrophy/hyperplasia), or by molecular markers, which include, but are not limited to, smooth muscle action (ACTA2), transgelin (TGLN), miR-145, high-molecular weight caldesmon 1 (h-CALD1), angpt2, Edn1, Elam, thrombospondin-1, vascular endothelial growth factor, alpha, calponin-1, inhibitor of metalloproteinases 1, lipocalin 2, growth-regulated alpha protein, alpha-1 acid glycoprotein 1, and total nitric oxide, biomarkers for ECactivation/damage, such as VCAM1, ICAM1, E-selectin, prostacyclin, angiopoietin 2, vascular endothelial growth factor A, thrombospndin 1; and biomarkers for VSMC damage (such as ACTA2, smoothelin, TGLN, CNN1, caeolin 1 (CAV1), and h-CALD1), and biomarkers for inflammation (such as CXCL1, lipocalin-2, interleukin-1, IL6, MCP1, MIP3A, AGP1, TIMP1), endothelial microparticles, and microRNAs (e.g., miR-17-92). More markers are described in Mikaelian et al. (Toxicologic Pathology, 42: 635-657, 2014).

In some embodiments, the side effect is hepatotoxicity. The toxicity can be detected and measured by any suitable method. In some embodiments, the toxicity is rated by ceruloplsmin, copper in 24-hour urine, ABCB7 genetic testing, MRI/ERCP, towering AST/ALT, echocardiogram, T3, T4, TSH test, liver biopsy, serology, and biomarkers, such as HLA-B*5701, microRNA (e.g., miR-122 and miR-192), HMGB-1, cytokeratin-18), Alanine aminotransferase (ALT), Alkaline phosphatase (ALP), Total bile acids (TBA), Creatinine (CREA), Blood urea nitrogen (BUN), Aspartate aminotransferase (AST), Sorbitol dehydrogenase (SDH), Albumin (ALB), Total protein (TP), Total bilirubin (TBIL), Lactate dehydrogenase (LDH), 5'-Nucleotidase (5'-NT), and Glutamate dehydrogenase (GLDH), Cyp21a1, Mfap3, MVD, and PTPRG. For detail, see Chang et al. (Int J Mol Sci. 2011; 12(7): 4609-4624) and Kullak-Ublicke al. (Gut 2017; 0:1-11. doi:10.1136/gutjnl-2016-313369).

In some embodiments, the side effect is pancreatic toxicity. The toxicity can be detected and measured by any suitable method. In some embodiments, the toxicity is rated by levels of serum amylase, serum lipase, RA1609, and/or RT2864. In some embodiments, the toxicity can be measured and monitored with the pancreatic enzymes, such as serum lipase and amylase, which are released into the bloodstream during damage.

In some embodiments, the side effect is gastrointestinal (GI) toxicity. The toxicity can be detected and measured by any suitable method. In some embodiments, the toxicity is rated by degree of mucositis, epithelium damage, sugar permeability test, blood test, or breath test. The toxicity refers to toxicities in the gut from the mouth through the stomach, small intestine, colon, and anus. Symptoms of GI toxicities include stomatitis, dysphagia, dyspepsia, diarrhea, nausea/vomiting, abdominal distension, constipation and abdominal pain. Clinical monitoring for these toxicities would include routine oral and abdominal examination, radiologic examination if warranted, blood tests to look for dehydration in case of symptoms of diarrhea or to look for anemia in case of symptoms of weakness or fatigue or dizziness or signs of rectal bleeding, and liver function tests in case of right-sided abdominal pain, etc.

In some embodiments, the side effect is nephrotoxicity or renal toxicity. The toxicity can be detected and measured by any suitable method. In some embodiments, the toxicity is rated by serum blood urea nitrogen (BUN) and creatinine levels, glomerular filtration rate (GFR), blood and/or protein in the urine, blood pressure, frequent and painful urination, swelling of hands and fee, puffiness around the eyes, urine parameters (coloration, glucose, ketones, leukocyte esterase, nitrites, protein, phosphates, urinary casts and crystals, hyaline, erythrocyte, leukocyte, etc.), biomarkers, such as cystaitin C, KIM-1, beta2-microglobulin, albumin, Tff3, clusterin, RPA-1, alphl-microglobulin, MIF, podocin, osteopontin, GST-alpha, VEGF, NGAL, Timp-1, NAG, netrin-1, RBP, IL-18, HGF, Cyr61, NHE-3, L-FABP, TFF-3, NHE-3, and calbindinD28.

In some embodiments, the side effect is neurotoxicity. The toxicity can be detected and measured by any suitable method. In some embodiments, the toxicity is rated by composite datasets of functional assessments (e.g., behavioral and electrophysiological measures, coupled with histopathological assessment of neural tissues), and biomarkers, such as levels of F2-IsoPs, GFAP, MAP-2, MBP, microtubule-associated protefin tau, neurofilament, spectrin breakdown product SBDP-145, translocator protein, ubiquitin C-terminal hydrolase, MRI T2 releaxation, and microPET, see Roberts et al. (Toxicol Sci. 2015 December; 148(2): 332-340).

In some embodiments, the side effect is ocular toxicity including but not limited to keratitis, visual loss, epiphora, conjunctivitis, photophobia, periorbital and eyelid edema, blepharitis and meibomitis, trichomegaly, retinal detachment, retinal vein occlusion. These toxicities can be detected with review of eye symptoms and vision issues in regular assessments. Some can be diagnosed on routine physical examination (e.g., conjunctivitis, blepharitis), whereas others require a dedicated ophthalmologic examination (e.g., retinal detachment, altered visual acuity).

In some embodiments, the side effect is ototoxicity (e.g., hearing loss). The toxicity can be detected and measured by any suitable method. In some embodiments, the toxicity is rated by behavioral score to sound stimulation.

In some embodiments, the toxicity is cutaneous toxicity. The toxicity can be detected and measured by any suitable method. In some embodiments, the toxicity is rated by visual and patient-reported side effects in the form of redness, itching, pain or blistering, peeling and open wounds (ulcerations), and particular examination of sun-exposed areas since some drugs may cause photosensitivity in response to sunlight.

In some embodiments, the toxicity is mucocutaneous toxicity. The toxicity can be detected and measured by any suitable method. In some embodiments, the toxicity is rated by visual observation, such as hyperpigmentation, nail discoloration, alopecia, scaling, rashes and oral apthosis (ulcers) or stomatitis.

In some embodiments, the toxicity is genitourinary toxicity. The toxicity can be detected and measured by any suitable method. The toxicity may include urinary urgency, incontinence, difficulty voiding, nocturne (urination at night), hematuria (blood in the urine), dysuria (painful urination), erectile dysfunction, bladder or kidney infection or infertility. These signs and symptoms can be monitored with a focused history, assessment of urine, measurement of sex hormones LH and FSH, measurement of estrogen or testosterone, and radiologic imaging or scopes inserted into the bladder or kidneys.

In addition to the standard clinical approaches described herein for evaluating toxicities mentioned in patients, clinicians would know what toxicities of a particular drug are and how to monitor them in view of patient history of taking the drugs and physical examination.

Administration of One or More Additional Therapeutic Agents

The methods may further comprise administering one or more additional therapeutic agents to the patient. Accordingly, in certain embodiments, the method further comprises administering at least one additional therapeutic agent to the patient. In certain embodiments, the additional pharmaceutical agent has been or will be administered to the patient at the time when the pharmaceutical composition comprising the first therapeutic agent is administered to the patient. In certain embodiments, the patient is administered the pharmaceutical composition comprising the first therapeutic agent and at least one additional, second therapeutic agent that is different from the first therapeutic agent. In certain embodiments, the patient is administered a pharmaceutical composition comprising the first therapeutic agent and at least two additional therapeutic agents (e.g., the second and the third therapeutic agents) that are different from the first therapeutic agent. In certain embodiments, the patient is administered a pharmaceutical composition comprising the first therapeutic agent and at least three, four, five, six, or seven additional therapeutic agents that are different from the first therapeutic agent.

In certain embodiments, the additional therapeutic agent is administered to the patient prior to the administration of the pharmaceutical composition comprising the first therapeutic agent. In certain embodiments, the additional therapeutic agent is administered to the patient subsequent to the administration of the pharmaceutical composition comprising the first therapeutic agent. In certain embodiments, the pharmaceutical agent is administered to the patient concurrently with the administration of the pharmaceutical composition comprising the first therapeutic agent. In certain embodiments, the additional therapeutic agent and the pharmaceutical composition comprising the first therapeutic agent can be administered in any manner that is suitable for therapeutic purposes.

In certain embodiments, the duration of time between administering the pharmaceutical composition comprising the first therapeutic agent and the additional therapeutic agent can be less than about 1 minute, about 1 minute, about 5 minutes, about 10 minutes, about 20 minutes, about 30 minutes, about 40 minutes, about 50 minutes, about 60 minutes, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 24 hours, about 2 days, about 3 days, about 4 days, about 5 days, about 10 days, about 15 days, about 20 days, about 25 days, about 30 days, about 35 days, about 40 days, about 45 days, about 50 days, about 55 days, or about 60 days, inclusive of all ranges and subranges therebetween. In certain embodiments, the duration of time can be any time so long as both the first therapeutic agent administered as part of the pharmaceutical composition and the additional therapeutic agent are concurrently in the patient.

In certain embodiments, the one or more additional therapeutic agents include but are not limited to paclitaxel, progesterone, verapamil, cyclosporine, dexrazoxane, cytarabine, cyclophosphamide, phenobarbital, phenytoin, streptozocin, saquinavir, etoposide, live vaccines, oral adenovirus types 4 and 7 live, amphotericin b deoxycholate, bacitracin, cidofovir, adjuvanted influenza virus vaccine trivalent, palifermin, pyridoxine, tofacitinib, acyclovir, adefovir, amikacin, belatacept, bendamustine, bumetanide, busulfan, capreomycin, carboplatin, carmustine, chlorambucil, cholera vaccine, colistin, dacarbazine, deflazacort, denosumab, dichlorphenamide, didanosine, elvitegravir, cobicistat, emtricitabine, tenofovir, ethotoin, fingolimod, foscarnet, fosphenytoin, furosemide, gentamicin, hydroxyurea, ifosfamide, influenza virus vaccine (h5n1), adjuvanted influenza virus vaccine (h5n1), ioversol, kanamycin, lomustine, mechlorethamine, melphalan, meningococcal group b vaccine, methotrexate, neomycin, nitazoxanide, ospemifene, oxaliplatin, paromomycin, pentamidine, peramivir, polymyxin b, rituximab, sipuleucel-t, sodium sulfate, potassium sulfate, magnesium sulfate, polyethylene glycol, streptomycin, tacrolimus, thiotepa, tobramycin, topotecan, vancomycin, zidovudine, magnesium oxide, paclitaxel protein bound, vinorelbine, vitamin A, vitamin E, taxanes, docetaxel, doxorubicin, epirubicin, anticonvulsants, carbamazepine, etanercept, hydrochlorothiazide, idarubicin, idelalisib, ivacaftor, allopurinol, antithrombin iii, argatroban, axitinib, bivalirudin, butabarbital, crofelemer, dabrafenib, dalteparin, daunorubicin liposomal, digoxin, doxorubicin liposomal, enoxaparin, flibanserin, fondaparinux, heparin, iloperidone, lomitapide, lumacaftor, meningococcal group b vaccine, mifepristone, mitotane, ocrelizumab, pentobarbital, primidone, ritonavir, secobarbital, sorafenib, succinylcholine, tinzaparin, warfarin, lepirudin, ruxolitinib, abiraterone, amiodarone, atorvastatin, azithromycin, captopril, carvedilol, clarithromycin, conivaptan, crizotinib, darunavir, dipyridamole, dronedarone, erythromycin base, erythromycin ethylsuccinate, erythromycin lactobionate, erythromycin stearate, felodipine, itraconazole, ketoconazole, lapatinib, ledipasvir, sofosbuvir, lopinavir, mefloquine, nelfinavir, nicardipine, nilotinib, quercetin, quinidine, quinine, ranolazine, velpatasvir, tamoxifen, ticagrelor, tolvaptan, vandetanib, vemurafenib, daclatasvir, diltiazem, eliglustat, eltrombopag, eluxadoline, ombitasvir, paritaprevir, osimertinib, ponatinib, regorafenib, rolapitant, safinamide, efavirenz, palifermin, atazanavir, eslicarbazepine acetate, etravirine, fosamprenavir, indinavir, tipranavir, clozapine, delavirdine, fosamprenavir, st john's wort, armodafinil, bosentan, cimetidine, clobazam, dasabuvir, enzalutamide, gemfibrozil, isoniazid, milk thistle, modafinil, nafcillin, nefazodone, nevirapine, oxcarbazepine, rifabutin, rifampin, rifapentine, sertraline, telithromycin, tetracycline, voriconazole, aprepitant, bevacizumab, bicalutamide, bosutinib, ceritinib, clotrimazole, desipramine, dexamethasone, fluconazole, imatinib, norfloxacin, schisandra, haloperidol, metronidazole, netupitant, palonosetron, and valerian.

Reduction in Drug-Drug Interactions of the Therapeutic Agent

In certain embodiments, when the method further comprises administering one or more additional therapeutic agents to the patient, the therapeutic agent in the pharmaceutical composition is subject to a reduced incidence of drug-drug interaction. Accordingly, in certain embodiments, the therapeutic agent in the pharmaceutical composition is subject to a reduced incidence of drug-drug interaction compared to direct administration of the same therapeutic agent at the same dose without being mixed with the blood product prior to administration. In certain embodiments, the reduced incidence of drug-drug interaction permits the use of a second therapeutic agent that would have otherwise been contraindicated.

By way of examples, the patient can be administered a pharmaceutical composition containing doxorubicin with verapamil. The patient can be administered a pharmaceutical composition containing cisplatin with cidofovir. The patient can be administered a pharmaceutical composition containing cyclophosphamide with etanercept. The patient can be administered a pharmaceutical composition containing topotecan with abiraterone. The patient can be administered a pharmaceutical composition containing ifosfamide with ivacaftor. The patient can be administered a pharmaceutical composition containing irinotecan with clozapine.

Therapeutic Agents—Indications, Doses, and Side Effects

Cardiac glycosides are a class of organic compounds that increase the output force of the heart and decrease its rate of contractions by acting on the cellular sodium-potassium ATPase pump. Their beneficial medical uses are as treatments for congestive heart failure and cardiac arrhythmias; however, their relative toxicity prevents them from being widely used.

Doxorubicin, or adriamycin, is a cytotoxic anthracycline antibiotic isolated from cultures of Streptomyces peucetius var. caesius. Doxorubicin binds to nucleic acids, presumably by specific intercalation of the planar anthracycline nucleus with the DNA double helix, and therefore, interfering with the function of DNA. It has been used as a chemotherapy medication for cancers including acute lymphoblastic leukemia, acute myeloblastic leukemia, Wilms' tumor, neuroblastoma, soft tissue and bone sarcomas, breast carcinoma, ovarian carcinoma, transitional cell bladder carcinoma, thyroid carcinoma, gastric carcinoma, Hodgkin's disease, malignant lymphoma and bronchogenic carcinoma, and the small cell histologic type. In some embodiments, doxorubicin is used to treat breast cancer, bladder cancer, Kaposi's sarcoma, lymphoma, or acute lymphocytic leukemia. In some embodiments, doxorubicin administered to a patient according to methods of the present invention provides comparable or increased therapeutic effect compared to other administration methods, but with reduced side effect or toxicity. Normally, the dose for doxorubicin is 40-75, such as 40-60 mg/m$^2$ IV or 60-75 mg/m$^2$ IV once 21 or 28 days in breast cancer treatment; 40-60 mg/m2 IV every 21 to 28 days in neuroblastoma treatment; 40 to 60 mg/m$^2$ IV every 21 to 27 days, or 60-75 mg/m2 IV every 21 to 28 days in Hodgkin's disease, ovarian cancer, Wilms' tumor, stomach cancer, acute lymphoblastic leukemia, lymphoma, osteosarcoma, acute myeloblastic leukemia, thyroid cancer, bronchogenic carcinoma, soft tissue sarcoma; 9 mg/m$^2$/day OV continuous infusion on days 1 to 4 for multiple myeloma; 35 to 75 mg/m$^2$ every 21 days for malignant disease. Methods of the present invention can allow using higher doses than the normal doses described herein, or using the same doses but with less side effects/toxicity. In some embodiments, the therapeutic effective amount of doxorubicin can be at least about 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1 mg/kg, 1.5 mg/kg, 2 mg/kg, 2.5 mg/kg, 3.0 mg/kg, 3.5 mg/kg, 4.0 mg/kg, 4.5 mg/kg, 5.0 mg/kg, 5.5 mg/kg, 6.0 mg/kg, 6.5 mg/kg, 7.0 mg/kg, 7.5 mg/kg, 8.0 mg/kg, 8.5 mg/kg, 9.0 mg/kg, 9.5 mg/kg, 10.0 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, or more, inclusive of all ranges and subranges therebetween, per intravenous dose. Side effects associated with doxorubicin include, but are not limited to, dilated cardiomyopathy, congestive heart failure, typhlitis, chemotherapy-induced acral erythema, reactivation of hepatitis B, and dyspigmentation.

Liposomal doxorubicin is a PEGylated liposome-encapsulated form of doxorubicin, sold as Doxil. In some embodiments, liposomal doxorubicin is used to treat Kaposi's sarcoma. Normally, the dose for liposomal doxorubicin is about 50 mg/m$^2$ IV per 28 days. Methods of the present invention can allow using higher doses than the normal doses described herein, or using the same doses but with less side effects/toxicity. In some embodiments, the therapeutic effective amount of liposomal doxorubicin can be at least about 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1 mg/kg, 1.5 mg/kg, 2 mg/kg, 2.5 mg/kg, 3.0 mg/kg, 3.5 mg/kg, 4.0 mg/kg, 4.5 mg/kg, 5.0 mg/kg, 5.5 mg/kg, 6.0 mg/kg, 6.5 mg/kg, 7.0 mg/kg, 7.5 mg/kg, 8.0 mg/kg, 8.5 mg/kg, 9.0 mg/kg, 9.5 mg/kg, 10.0 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, or more, inclusive of all ranges and subranges therebetween, per intravenous dose. Side effects associated with liposome doxorubicin include, but are not limited to, palmar plantar erythrodysesthesia (PPE), more commonly known as hand-foot syndrome.

Daunorubicin (a.k.a., daunomycin) is a chemotherapy medication for cancer treatment. In some embodiments, daunorubicin is used to treat acute myeloid leukemia (AML), acute lymphocytic leukemia (ALL), chronic myelogenous leukemia (CML), and Kaposi's sarcoma. Normally, the dose for daunorubicin is about 30 to 45 mg/m$^2$ IVP for 7 days in a first course, and for 5 days in a subsequent course. In the first course, it is administered at day 1, 2, and 3; in the second course, it is administered at day 1 and 2. Methods of the present invention can allow using higher doses than the normal doses described herein, or using the same doses but with less side effects/toxicity. In some embodiments, the therapeutic effective amount of daunorubicin can be at least about 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1 mg/kg, 1.5 mg/kg, 2 mg/kg, 2.5 mg/kg, 3.0 mg/kg, 3.5 mg/kg, 4.0 mg/kg, 4.5 mg/kg, 5.0 mg/kg, 5.5 mg/kg, 6.0 mg/kg, 6.5 mg/kg, 7.0 mg/kg, 7.5 mg/kg, 8.0 mg/kg, 8.5 mg/kg, 9.0 mg/kg, 9.5 mg/kg, 10.0 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, or more, inclusive of all ranges and subranges therebetween, per intravenous dose. Side effects associated with daunorubicin include, but are not limited to, hair loss, vomiting, bone marrow suppression, inflammation, tissue death, cardiotoxicity, renal toxicity, and hepatotoxicity.

Idarubicin, or 4-demethoxydaunorubicin, is an anthracycline antileukemic drug. It inserts itself into DNA and prevents DNA unwinding by interfering with the enzyme topoisomerase II. In some embodiments, idarubicin is used to treat acute myeloid leukemia (AML), acute lymphocytic leukemia (ALL), chronic myelogenous leukemia (CML), and Kaposi's sarcoma. Normally, the dose for idarubicin is about 12 mg/m$^2$ IV a day over 10-15 min for 3 days. Methods of the present invention can allow using higher doses than the normal doses described herein, or using the same doses but with less side effects/toxicity. In some embodiments, the therapeutic effective amount of idarubicin can be at least about 0.1 mg/kg, 0.15 mg/kg, 0.2 mg/kg, 0.25 mg/kg, 0.3 mg/kg, 0.35 mg/kg, 0.4 mg/kg, 0.45 mg/kg, 0.5 mg/kg, 0.55 mg/kg, 0.6 mg/kg, 0.65 mg/kg, 0.7 mg/kg, 0.75 mg/kg, 0.8 mg/kg, 0.85 mg/kg, 0.9 mg/kg, 0.95 mg/kg, 1 mg/kg, 1.5 mg/kg, 2 mg/kg, 2.5 mg/kg, 3.0 mg/kg, 3.5 mg/kg, 4.0 mg/kg, 4.5 mg/kg, 5.0 mg/kg, 5.5 mg/kg, 6.0 mg/kg, 6.5 mg/kg, 7.0 mg/kg, 7.5 mg/kg, 8.0 mg/kg, 8.5 mg/kg, 9.0 mg/kg, 9.5 mg/kg, 10.0 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, or more, or more. Side effects associated with daunorubicin include, but are not limited to, vomiting, mucositis, diarrhea, myocardial toxicity, renal toxicity, and hepatotoxicity.

Cisplatin, or cisplatin, is an alkylating agent that can be used as a chemotherapy drug for cancers include but are not limited to advanced bladder cancer, metastatic ovarian cancer, and metastatic testicular cancer, testicular, ovarian, bladder, head and neck, esophageal, small and non-small cell lung, breast, cervical, stomach and prostate cancers, Hodgkin's and non-Hodgkin's lymphomas, neuroblastoma, sarcomas, multiple myeloma, melanoma, and mesothelioma. Cisplatin can interferes with DNA replication and thereby inhibit DNA synthesis. It can disrupt DNA function by covalently binding to DNA bases and can also produce DNA intrastrand cross-linking and breakages. Cisplatin can have half-life elimination time from about 24 hours to 47 days. In some embodiments, cisplatin is used to treat testicular cancer, ovarian cancer, cervical cancer, breast cancer, bladder cancer, head and neck cancer, esophageal cancer, lung cancer, mesothelioma, brain tumors or neuroblastoma, among others. In some embodiments, cisplatin administered to a patient according to methods of the present invention provides comparable or increased therapeutic effect compared to other administration methods, but with reduced side effect or toxicity. Normally, the dose for cisplatin is about 20 mg/m$^2$ to 300 mg/m$^2$, such as 20 mg/m$^2$/day IV in a 5 day cycle for metastatic testicular tumors; 50-70 mg/m$^2$ IV in a cycle of 3-4 weeks for bladder cancer; 75-100 mg/m$^2$ IV in a cycle of 4 weeks, or 90-270 mg/m$^2$ intraperitoneal for metastatic ovarian carcinoma; 75-100 mg/m$^2$ IV q4 weeks when used with cyclophosphamide. Methods of the present invention can allow using higher doses than the normal doses described herein, or using the same doses but with less side effects/toxicity. In some embodiments, the therapeutic effective amount of cisplatin can be at least about 0.1 mg/kg, 0.15 mg/kg, 0.2 mg/kg, 0.25 mg/kg, 0.3 mg/kg, 0.35 mg/kg, 0.4 mg/kg, 0.45 mg/kg, 0.5 mg/kg, 0.55 mg/kg, 0.6 mg/kg, 0.65 mg/kg, 0.7 mg/kg, 0.75 mg/kg, 0.8 mg/kg, 0.85 mg/kg, 0.9 mg/kg, 0.95 mg/kg, 1 mg/kg, 1.5 mg/kg, 2 mg/kg, 2.5 mg/kg, 3.0 mg/kg, 3.5 mg/kg, 4.0 mg/kg, 4.5 mg/kg, 5.0 mg/kg, 5.5 mg/kg, 6.0 mg/kg, 6.5 mg/kg, 7.0 mg/kg, 7.5 mg/kg, 8.0 mg/kg, 8.5 mg/kg, 9.0 mg/kg, 9.5 mg/kg, 10.0 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, or more, inclusive of all ranges and subranges therebetween, per intravenous dose. Side effects associated with cisplatin include, but are not limited to, bone marrow suppression, nerve damage (neurotoxicity), hearing problems (ototoxicity), kidney problems (nephrotoxicity), nausea and vomiting, electrolyte disturbance, numbness, trouble walking, allergic reactions, hemolytic anemia, and heart disease (cardiotoxicity).

Carboplatin (e.g., paraplatin), is a platinum based antineoplastic compound that can be used for treating cancer. Without wishing to be bound by theory, the mechanisms of carboplatin are similar to cisplatin. In some embodiments, carboplatin is used to treat ovarian cancer, lung cancer, head and neck cancer, brain cancer, or neuroblastoma, among others. Normally, the dose is 150-600 mg/m$^2$ by intravenous injection, such as 300 mg/m$^2$ for ovarian cancer, 200 mg/m$^2$ for cervical cancer in a 21 day cycle; the dose is 175 mg/m$^2$ once weekly for 4 weeks in brain tumor treatment. Methods of the present invention can allow using higher doses than the normal doses described herein, or using the same doses but with less side effects/toxicity. In some embodiments, the therapeutic effective amount of carboplatin can be at least about 1 mg/kg, 1.5 mg/kg, 2 mg/kg, 2.5 mg/kg, 3.0 mg/kg, 3.5 mg/kg, 4.0 mg/kg, 4.5 mg/kg, 5.0 mg/kg, 5.5 mg/kg, 6.0 mg/kg, 6.5 mg/kg, 7.0 mg/kg, 7.5 mg/kg, 8.0 mg/kg, 8.5 mg/kg, 9.0 mg/kg, 9.5 mg/kg, 10.0 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 21 mg/kg, 22 mg/kg, 23 mg/kg, 24 mg/kg, 25 mg/kg, 26 mg/kg, 27 mg/kg, 28 mg/kg, 29 mg/kg, 30 mg/kg, 40 mg/kg, 50 mg/kg, 60 mg/kg, 70 mg/kg, 80 mg/kg, 90 mg/kg, 100 mg/kg, 110 mg/kg, 120 mg/kg, 130 mg/kg, 140 mg/kg, 150 mg/kg, 160 mg/kg, 170 mg/kg, 180 mg/kg, 190 mg/kg, 200 mg/kg, or more, inclusive of all ranges and subranges therebetween, per intravenous dose. Side effects associated with carboplatin include, but are not limited to, myelosuppression (e.g., reduced blood cell), electrolyte disturbance, nausea, allergic reactions, and increased risk of other cancers.

Oxaliplatin (e.g., eloxatin) is a platinum based antineoplastic compound that can be used for treating cancer, Without wishing to be bound by theory, the mechanisms of oxaliplatin through non-targeted cytotoxic effects. Like other platinum compounds, its cytotoxicity is thought to result from inhibition of DNA synthesis in cells. In particular, oxaliplatin forms both inter- and intra-strand cross links in DNA, which prevent DNA replication and transcription, causing cell death. In some embodiments, oxaliplatin is used to treat colorectal cancer, among others. Normally, the dose is 75-85 mg/m$^2$ IV infused over 2 hr. Methods of the present invention can allow using higher doses than the normal doses described herein, or using the same doses but with less side effects/toxicity. In some embodiments, the therapeutic effective amount of oxaliplatin can be at least about 1 mg/kg, 1.5 mg/kg, 2 mg/kg, 2.5 mg/kg, 3.0 mg/kg, 3.5 mg/kg, 4.0 mg/kg, 4.5 mg/kg, 5.0 mg/kg, 5.5 mg/kg, 6.0 mg/kg, 6.5 mg/kg, 7.0 mg/kg, 7.5 mg/kg, 8.0 mg/kg, 8.5 mg/kg, 9.0 mg/kg, 9.5 mg/kg, 10.0 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 21 mg/kg, 22 mg/kg, 23 mg/kg, 24 mg/kg, 25 mg/kg, 26 mg/kg, 27 mg/kg, 28 mg/kg, 29 mg/kg, 30 mg/kg, 40 mg/kg, 50 mg/kg, 60 mg/kg, 70 mg/kg, 80 mg/kg, 90 mg/kg, 100 mg/kg, 110 mg/kg, 120 mg/kg, 130 mg/kg, 140 mg/kg, 150 mg/kg, 160 mg/kg, 170 mg/kg, 180 mg/kg, 190 mg/kg, 200 mg/kg, or more, inclusive of all ranges and subranges therebetween, per intravenous dose. Side effects associated with oxaliplatin include, but are not limited to, neurotoxicity (e.g., chemotherapy induced peripheral neuropathy), nephrotoxicity, fatigue, nausea, vomiting or diarrhea, neutropenia (e.g., reduced number of a blood cell), ototoxicity (e.g., hearing loss), extravasation (e.g., damage to connective tissues), hypokalemia (e.g., low blood potassium), persistent hiccups, and rhabdomyolysis.

Paclitaxel (i.e., Taxol), is known as an anti-mitotic agent, a plant alkaloid, a taxane, or an anti-microtubule agent that can be used for treating breast, ovarian, cervical, pancreatic, prostate, bladder, lung, esophageal, and head and neck cancers, Kappsi sarcoma, and melanoma. Without wishing to be bound by theory, the mechanisms of paclitaxel are through disrupting the functions of microtubule structures during cell divisions, and thereby causing defects in mitotic spindle assembly, chromosome segregation, and cell division. Normally, the dose for ovarian cancer is about 100-200 mg/m$^2$ IV, such as 175 mg/m$^2$ IV over 3 hours q3 weeks, or 135 mg/m$^2$ IV over 24 hours q3 weeks; the dose for breast cancer is 175 mg/m$^2$ IV over 3 hours q3 Weeks 4 times; the dose for non-small cell lung cancer is 135 mg/m2 IV over 3 hours q3 weeks, or 100 mg/m$^2$ IV over 3 hours q2 weeks; the dose for pancreatic cancer is 125 mg/m$^2$ IV with gemcitabine. Methods of the present invention can allow using higher doses than the normal doses described herein, or using the same doses but with less side effects/toxicity. In some embodiments, the therapeutic effective amount of paclitaxel can be at least about 1 mg/kg, 1.5 mg/kg, 2 mg/kg, 2.5 mg/kg, 3.0 mg/kg, 3.5 mg/kg, 4.0 mg/kg, 4.5 mg/kg, 5.0 mg/kg, 5.5 mg/kg, 6.0 mg/kg, 6.5 mg/kg, 7.0 mg/kg, 7.5 mg/kg, 8.0 mg/kg, 8.5 mg/kg, 9.0 mg/kg, 9.5 mg/kg, 10.0 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 21 mg/kg, 22 mg/kg, 23 mg/kg, 24 mg/kg, 25 mg/kg, 26 mg/kg, 27 mg/kg, 28 mg/kg, 29 mg/kg, 30 mg/kg, 40 mg/kg, 50 mg/kg, or more, inclusive of all ranges and subranges therebetween, per intravenous dose. Side effects associated with paclitaxel include, but are not limited to, hair loss, myelosuppression (e.g., bone marrow suppression), numbness, allergic reactions, muscle pains, diarrhea, cardiotoxicity (e.g., heart problems), increased risk of infection, and pulmonary toxicity (e.g., lung inflammation).

Cyclophosphamide, or cytophosphane, is an alkylating agent that can be used for treating cancer such as brain cancer, neuroblastoma, leukemia, non-Hodgkin lymphoma, breast cancer, and autoimmune diseases such as rheumatoid arthritis. The metabolites of cyclophosphamide, which include but are not limited to phosphoramide mustard, interfere with malignant cell growth by cross-linking tumor cell DNA, and lead to apoptosis. Cyclophosphamide can also have immunomodulatory capabilities. Without wishing to be bound by theory, cyclophosphamide can induce T cell growth factors. The elimination time of the drug can range from 3 to 12 hours. Normally, the dose for cyclophosphamide is about 100-2000 mg/m$^2$, such as 40-50 mg/kg (400-1800 mg/m$^2$) divided over 2-5 days, which may be repeated at intervals of 2-4 weeks, or 60-120 mg/m$^2$ (1-2.5 mg/kg/day) IV for continuous daily therapy; 400-1000 mg/m2 PO divided over 4-5 days for intermittent therapy; or 50-100 mg/m$^2$/day or 1-5 mg/kg/day PO for continuous daily therapy; the dose for nephrotic syndrome is 2-3 mg/kg/day for up to 12 weeks; the dose for non-Hodgkin lymphoma is 600-1500 mg/m$^2$ IV with other anti-neoplastic; the dose for breast cancer is 600 mg/m$^2$ IV with other anti-neoplastic; the dose for juvenile idiopathic arthritis is 10 mg/kg IV every 2 weeks; the dose for lupus nephritis is 500 mg/m$^2$-1000 mg/m$^2$ IV every 2 weeks for 6 doses plus corticosteroids. Methods of the present invention can allow using higher doses than the normal doses described herein, or using the same doses but with less side effects/toxicity. In some embodiments, the therapeutic effective amount of cyclophosphamide can be at least about 1 mg/kg, 1.5 mg/kg, 2 mg/kg, 2.5 mg/kg, 3.0 mg/kg, 3.5 mg/kg, 4.0 mg/kg, 4.5 mg/kg, 5.0 mg/kg, 5.5 mg/kg, 6.0 mg/kg, 6.5 mg/kg, 7.0 mg/kg, 7.5 mg/kg, 8.0 mg/kg, 8.5 mg/kg, 9.0 mg/kg, 9.5 mg/kg, 10.0 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 21 mg/kg, 22 mg/kg, 23 mg/kg, 24 mg/kg, 25 mg/kg, 26 mg/kg, 27 mg/kg, 28 mg/kg, 29 mg/kg, 30 mg/kg, 40 mg/kg, 50 mg/kg, 60 mg/kg, 70 mg/kg, 80 mg/kg, 90 mg/kg, 100 mg/kg, 110 mg/kg, 120 mg/kg, 130 mg/kg, 140 mg/kg, 150 mg/kg, 160 mg/kg, 170 mg/kg, 180 mg/kg, 190 mg/kg, 200 mg/kg, or more, inclusive of all ranges and subranges therebetween, per intravenous dose. Side effects associated with cyclophosphamide include, but are not limited to, low white blood cell counts, loss of appetite, vomiting, hair loss, bleeding from the bladder, increased future risk of cancer, infertility, allergic reactions, and pulmonary fibrosis.

Topotecan can be classified as a topoisomerase inhibitor and is used as a chemotherapeutic agent to treat ovarian cancer, cervical cancer, and small cell lung carcinoma Topotecan can be derived from camptothecin, an extract from *Camptotheca acuminate*, and binds to topoisomerase I to produce double-strand breaks in DNA. The elimination time of the drug can range from 2 to 3 hours. Normally, the dose for ovarian cancer is about 0.5 to 2 mg/m$^2$ IV, such as 1.5 mg/m$^2$ IV over 30 minutes once a day for 5 consecutive days; the dose for cervical cancer is 0.75 mg/m$^2$ IV over 30 minutes on days 1, 2, and 3 of each 21 day cycle; the dose for small cell lung cancer is 1.5 mg/m$^2$ IV over 30 minutes once a day for 4 consecutive days of a 21 day cycle. Methods of the present invention can allow using higher doses than the normal doses described herein, or using the same doses but with less side effects/toxicity. In some embodiments, the therapeutic effective amount of topotecan can be at least about 0.01 mg/kg, 0.02 mg/kg, 0.03 mg/kg, 0.04 mg/kg, 0.05 mg/kg, 0.06 mg/kg, 0.07 mg/kg, 0.08 mg/kg, 0.09 mg/kg, 0.1 mg/kg, 0.15 mg/kg, 0.2 mg/kg, 0.25 mg/kg, 0.3 mg/kg, 0.35 mg/kg, 0.4 mg/kg, 0.45 mg/kg, 0.5 mg/kg, 0.6 mg/kg, 0.7 mg/kg, 0.8 mg/kg, 0.9 mg/kg, 1 mg/kg, 1.5 mg/kg, 2 mg/kg, 2.5 mg/kg, 3 mg/kg, 3.5 mg/kg, 4 mg/kg, 4.5 mg/kg, 5 mg/kg, 5.5 mg/kg, 6 mg/kg, 7 mg/kg, 8 mg/kg, 9 mg/kg, 10 mg/kg, or more, inclusive of all ranges and subranges therebetween, per intravenous dose. Side effects associated with topotecan include, but are not limited to, myelosuppression (e.g., neutropenia, leukopenia, anemia, and thrombocytopenia), diarrhea, nausea, vomiting, stomatitis, constipation, susceptibility to infections, and asthenia.

Ifosfamide is an oxazaphosphinanyl chemotherapy medication, which treats testicular cancer, soft tissue sarcoma, osteosarcoma, bladder cancer, small cell lung cancer, cervical cancer, lymphoma, and ovarian cancer. Ifosfamide can be categorized as an alkylating agent and a member of the nitrogen mustard family of medications. The mechanisms of actions of ifosfamide can include but are not limited to the disruption of DNA duplication and the cross-linking of DNA strands, and thereby lead to the inhibition of DNA and protein synthesis. The elimination time of ifosfamide can range from 7 to 15 hours, depending on the level of dosages. Normally, the dose is about 0.5 to 1.5 mg/m$^2$/day IV infusion over 30 minutes on days 1-5 q3-4 weeks, or 2 g/m$^2$/day IV infusion on days 1-3, or 5 g/m$^2$ over 24 hr via continues IV infusion in combination with other antineoplastic compounds. Methods of the present invention can allow using higher doses than the normal doses described herein, or using the same doses but with less side effects/toxicity. In some embodiments, the therapeutic effective amount of ifosfamide can be at least about 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 21 mg/kg, 22 mg/kg, 23 mg/kg, 24 mg/kg, 25 mg/kg, 26 mg/kg, 27 mg/kg, 28 mg/kg, 29 mg/kg, 30 mg/kg, 40 mg/kg, 50 mg/kg, 60 mg/kg, 70 mg/kg, 80 mg/kg, 90 mg/kg, 100 mg/kg, 110 mg/kg, 120 mg/kg, 130 mg/kg, 140 mg/kg, 150 mg/kg, 160 mg/kg, 170 mg/kg, 180 mg/kg, 190 mg/kg, 200 mg/kg, 210 mg/kg, 220 mg/kg, 230 mg/kg, 240 mg/kg, 250 mg/kg, 260 mg/kg, 270 mg/kg, 280 mg/kg, 290 mg/kg, 300 mg/kg, 310 mg/kg, 320 mg/kg, 330 mg/kg, 340 mg/kg, 350 mg/kg, 360 mg/kg, 370 mg/kg, 380 mg/kg, 390 mg/kg, 400 mg/kg, or more, inclusive of all ranges and subranges therebetween, per intravenous dose. Side effects associated with ifosfamide include, but are not limited to, hair loss, vomiting, blood in the urine, infections, kidney problems, bone marrow suppression, decreased level of consciousness.

Irinotecan is a topoisomerase inhibitor that can be used to treat colorectal cancer, pancreatic cancer, ovarian cancer, and small cell lung cancer. Irinotecan binds to topoisomerase I to produce double-strand breaks in DNA and inhibit DNA replication and transcription. Alternatively, before binding to topoisomerase I, irinotecan can be first hydrolyzed to SN-38, an active metabolite of Irinotecan. The half-life of irinotecan can range from 6 to 12 hours. Normally, the dose is about 100 to 500 mg/m$^2$ IV, such as 125 mg/m$^2$ IV infusion over 90 minutes on days 1, 8, 15, 22, then 2 weeks off, then repeat, or 350 mg/m$^2$ IV infusion over 30-90 minutes q3 weeks. Methods of the present invention can allow using higher doses than the normal doses described herein, or using the same doses but with less side effects/toxicity. In some embodiments, the therapeutic effective amount of irinotecan can be at least about 1 mg/kg, 1.5 mg/kg, 2 mg/kg, 2.5 mg/kg, 3.0 mg/kg, 3.5 mg/kg, 4.0 mg/kg, 4.5 mg/kg, 5.0 mg/kg, 5.5 mg/kg, 6.0 mg/kg, 6.5 mg/kg, 7.0 mg/kg, 7.5 mg/kg, 8.0 mg/kg, 8.5 mg/kg, 9.0 mg/kg, 9.5 mg/kg, 10.0 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 21 mg/kg, 22 mg/kg, 23 mg/kg, 24 mg/kg, 25 mg/kg, 26 mg/kg, 27 mg/kg, 28 mg/kg, 29 mg/kg, 30 mg/kg, 40 mg/kg, 50 mg/kg, or more, inclusive of all ranges and subranges therebetween, per intravenous dose. Side effects associated with irinotecan include, but are not limited to, diarrhea, vomiting, bone marrow suppression (low white blood cell count and red blood cell count), hair loss, shortness of breath, fever, blood clots, colon inflammation, and allergic reactions.

Etoposide, e.g., etopophos, is a chemotherapy drug. Conditions that can be treated by etoposide include, but are not limited to, testicular cancer, lung cancer, lymphoma, leukemia, neuroblastoma, and ovarian cancer. Normally, the dose for etoposide is about 50 to 100 mg/m$^2$ IV on day 1 to day 5, or 100 mg/m$^2$ once a day on days 1, 3, and 5 for testicular cancer; 35 mg/m2 IV once a day for 4 days to 50 mg/m$^2$ UV once a day for 5 days. Methods of the present invention can allow using higher doses than the normal doses described herein, or using the same doses but with less side effects/toxicity. In some embodiments, the therapeutic effective amount of etoposide can be at least about 1 mg/kg, 1.5 mg/kg, 2 mg/kg, 2.5 mg/kg, 3.0 mg/kg, 3.5 mg/kg, 4.0 mg/kg, 4.5 mg/kg, 5.0 mg/kg, 5.5 mg/kg, 6.0 mg/kg, 6.5 mg/kg, 7.0 mg/kg, 7.5 mg/kg, 8.0 mg/kg, 8.5 mg/kg, 9.0 mg/kg, 9.5 mg/kg, 10.0 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 21 mg/kg, 22 mg/kg, 23 mg/kg, 24 mg/kg, 25 mg/kg, 26 mg/kg, 27 mg/kg, 28 mg/kg, 29 mg/kg, 30 mg/kg, 40 mg/kg, 50 mg/kg, or more, inclusive of all ranges and subranges therebetween, per intravenous dose. Side effects associated with etoposide include, but are not limited to, bone marrow suppression (low blood cell count), vomiting, loss of appetite, diarrhea, hair loss, fever, allergic reactions, and low blood pressure.

Teniposide (e.g., vumon) is a chemotherapeutic medication used in the treatment of childhood acute lymphocytic leukemia (ALL), Hodgkin's lymphoma, certain brain tumors, and other types of cancer. Normally, the dose for teniposide is about 100 to 300 mg/m$^2$ IV for patients having acute lymphocytic leukemia, or about 30 mg/m$^2$/day for 10 days, 50 to 100 mg/m$^2$ once a week, or 60-70 mg/m$^2$/day once a week in patients having non-Hodgkin's lymphoma. Methods of the present invention can allow using higher doses than the normal doses described herein, or using the same doses but with less side effects/toxicity. In some embodiments, the pharmaceutical composition can contain a teniposide concentration of at least about 0.5 mg/kg, 0.6 mg/kg, 0.7 mg/kg, 0.8 mg/kg, 0.9 mg/kg, 1 mg/kg, 1.5 mg/kg, 2 mg/kg, 2.5 mg/kg, 3.0 mg/kg, 3.5 mg/kg, 4.0 mg/kg, 4.5 mg/kg, 5.0 mg/kg, 5.5 mg/kg, 6.0 mg/kg, 6.5 mg/kg, 7.0 mg/kg, 7.5 mg/kg, 8.0 mg/kg, 8.5 mg/kg, 9.0 mg/kg, 9.5 mg/kg, 10.0 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 21 mg/kg, 22 mg/kg, 23 mg/kg, 24 mg/kg, 25 mg/kg, 26 mg/kg, 27 mg/kg, 28 mg/kg, 29 mg/kg, 30 mg/kg, 40 mg/kg, 50 mg/kg, or more, inclusive of all ranges and subranges therebetween, per intravenous dose. Side effects associated with teniposide include, but are not limited to, bone marrow suppression, gastrointestinal toxicity, hypersensitivity reactions, hypotension, and reversible alopecia.

Mitoxantrone (e.g., mitozantrone, novantrone) is an anthracenedione antineoplastic compound, which is a type II topoisomerase inhibitor. In some embodiments, mitoxantrone is used to treat metastatic breast cancer, acute myeloid leukemia, acute lymphoblastic leukemia relapse, prostate cancer, multiple sclerosis (MS), and non-Hodgkin's lymphoma. It disrupts DNA synthesis and DNA repair in both healthy cells and cancer cells by intercalation between DNA bases. Normally, the dose for mitoxantrone is about 12-14 mg/m$^2$ IV infusion q3 months. Methods of the present invention can allow using higher doses than the normal doses described herein, or using the same doses but with less side effects/toxicity. In some embodiments, the pharmaceutical composition can contain a mitoxantrone concentration of at least about 0.1 mg/kg, 0.15 mg/kg, 0.2 mg/kg, 0.25 mg/kg, 0.3 mg/kg, 0.35 mg/kg, 0.4 mg/kg, 0.45 mg/kg, 0.5 mg/kg, 0.6 mg/kg, 0.7 mg/kg, 0.8 mg/kg, 0.9 mg/kg, 1 mg/kg, 1.5 mg/kg, 2 mg/kg, 2.5 mg/kg, 3 mg/kg, 3.5 mg/kg, 4 mg/kg, 4.5 mg/kg, 5 mg/kg, 5.5 mg/kg, 6 mg/kg, 7 mg/kg, 8 mg/kg, 9 mg/kg, 10 mg/kg, or more, inclusive of all ranges and subranges therebetween, per intravenous dose. Side effects associated with mitroxanthrone include, but are not limited to nausea, vomiting, hair loss, heart damage, immunosuppression, and cardiotoxicity.

Digoxin is in the cardiac glycoside family of medications. It was isolated from the foxglove plant, *Digitalis lanata*. It is a medication used to treat various heart conditions, such as for atrial fibrillation, atrial flutter, and heart failure. Digoxin's primary mechanism of action involves inhibition of the sodium potassium adenosine triphosphatase (Na+/K+ ATPase), mainly in the myocardium. This inhibition causes an increase in intracellular sodium levels, resulting in decreased activity of the sodium-calcium exchanger, which normally imports three extracellular sodium ions into the cell and transports one intracellular calcium ion out of the cell. The inaction of this exchanger causes an increase in the intracellular calcium concentration that is available to the contractile proteins. Increased intracellular calcium lengthens phase 4 and phase 0 of the cardiac action potential, which leads to a decrease in heart rate. Normally, the dose for rapid digitalizing regimen is 8-12 μg/kg IV or 10-15 μg/kg PO (administer 50% initially; then may cautiously give ¼ the loading dose q6-8 hr twice); the dose for maintenance is about 3.4-5.1 mcg/kg/day or 0.125-0.5 mg/day PO, or 0.1-0.4 mg qDay IV/IM; and the dose for heart failure is 0.125-0.25 mg PO/IV qDay. Methods of the present invention can allow using higher doses than the normal doses described herein, or using the same doses but with less side effects/toxicity. In some embodiments, the therapeutic effective amount of digoxin can be at least about 1 μg/kg, 2 μg/kg, 3 μg/kg, 4 μg/kg, 5 μg/kg, 6 μg/kg, 7 μg/kg, 8 μg/kg, 9 μg/kg, 10 μg/kg, at least about 11 μg/kg, at least about 12 μg/kg, at least about 13 μg/kg, at least about 14 μg/kg, at least about 15 μg/kg, at least about 16 μg/kg, at least about 17 μg/kg, at least about 18 μg/kg, at least about 19 μg/kg, at least about 20 μg/kg, at least about 21 μg/kg, at least about 22 μg/kg, at least about 23 μg/kg, at least about 24 μg/kg, at least about 25 μg/kg, at least about 26 μg/kg, at least about 27 μg/kg, at least about 28 μg/kg, at least about 29 μg/kg, at least about 30 μg/kg, or more inclusive of all ranges and subranges therebetween, per intravenous dose. Side effects associated with digoxin include, but are not limited to, breast enlargement, loss of appetite, nausea, trouble seeing, confusion, and an irregular heartbeat.

Vancomycin is used to treat bacterial infections, such as skin infections, bloodstream infections, endocarditis, bone and joint infection, severe *Clostridium difficile* colitis, and meningitis caused by methicillin resistant *S. aureus*. Vancomycin is considered a last resort medication for the treatment of septicemia and lower respiratory tract, skin, and bone infections caused by Gram-positive bacteria. The minimum inhibitory concentration susceptibility data for a few medically significant bacteria are, 0.25 μg/mL to 4.0 μg/mL for *Staphylococcus aureus*, 1 μg/mL to 138 μg/mL for *Staphylococcus aureus* (methicillin resistant or MRSA), and ≤0.12 μg/mL to 6.25 μg/mL for *Staphylococcus epidermidis*. The recommended trough level is about 10 to 15 mg/l or 15 to 20 mg/l. Normally, the dose for pseudomembranous colitis or Staphylococcal enterocolitis is about 125 mg PO q6 hr for 10 days, or 0.5-2 g/day PO divided q6-8 hr for 7-10 days; the dose for endocarditis is about 500 mg IV q6 hr or 1 g IV q12 hr; the dose for gastrointestinal and genitourinary procedures is about 1 g IV by slow infusion over 1 hour, and not to exceed 120 mg UV r IM<30 minutes before procedure; the dose for surgical prophylaxis is about 15 mg/kg IV over 1-2 hr. Normally, recommended peak value is 18-26 mg/L, and the trough value is about 5-10 mg/L. Methods of the present invention can allow using higher doses than the normal doses described herein, or using the same doses but with less side effects/toxicity. In some embodiments, the therapeutic effective amount of vancomycin can be at least about 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, at least about 11 mg/kg, at least about 12 mg/kg, at least about 13 mg/kg, at least about 14 mg/kg, at least about 15 mg/kg, at least about 16 mg/kg, at least about 17 mg/kg, at least about 18 mg/kg, at least about 19 mg/kg, at least about 20 mg/kg, at least about 21 mg/kg, at least about 22 mg/kg, at least about 23 mg/kg, at least about 24 mg/kg, at least about 25 mg/kg, at least about 26 mg/kg, at least about 27 mg/kg, at least about 28 mg/kg, at least about 29 mg/kg, at least about 30 mg/kg, or more inclusive of all ranges and subranges therebetween, per intravenous dose. Side effects associated with vancomycin include, but are not limited to, local pain, thrombophlebitis, allergic reactions, ototoxicity (hearing loss), nephrotoxicity (kidney damage), low blood pressure, bone marrow suppression, anaphylaxis, toxic epidermal necrolysis, erythema multiforme, red man syndrome, super-infection, thrombocytopenia, neutropenia, leukopenia, tinnitus, dizziness and/or ototoxicity, DRESS syndrome, thrombocytopenia and bleeding with florid petechial hemorrhages, ecchymoses, and wet purpura.

Imipenem (e.g., primaxin) is an intravenous β-lactam antibiotic, a member of the carbapenem class of antibiotics. Carbapenems are highly resistant to the β-lactamase enzymes produced by many multiple drug-resistant Gram-negative bacteria, thus play a key role in the treatment of infections not readily treated with other antibiotics. Imipenem acts as an anti-microbial through inhibiting cell wall synthesis of various Gram-positive and Gram-negative bacteria. The spectrum of bacterial susceptible to imipenem includes, *Acinetobacter anitratus, Acinetobacter calcoaceticus, Actinomyces odontolyticus, Aeromonas hydrophila, Bacteroides distasonis, Bacteroides uniformis*, and *Clostridium perfringens. Acinetobacter baumannii*, some *Acinetobacter* spp., *Bacteroides fragilis*, and *Enterococcus faecalis* have developed resistance to imipenem to varying degrees. Imipenem can also be used to treat sepsis, abdominal infections, complicated urinary tract infections, pneumonia, blood stream infections. Normally, the dose is about 200-1000 mg IV, such as, for lower respiratory tract, skin/skin structure, and gynecologic infections, the dose is about 500-750 mg IV q12 hr; the dose for intra-abdominal infections is about 250-500 mg IV q6 hr; the dose for infections is about 500 mg IV q6 hr; the dose for urinary tract infections is about 250-500 mg IV q6 hr; the dose for mild infections is about 250-500 mg IV q6-8 hr; the dose for moderate infections is about 500 mg to 1 g IV q6-8 hr, and the dose for severe infections is about 500 mg to 1 g q 6 hr, and not to exceed 50 mg/kg/day or 4 g/day. Methods of the present invention can allow using higher doses than the normal doses described herein, or using the same doses but with less side effects/toxicity. In some embodiments, the therapeutic effective amount of imipenem can be at least about 10 mg/kg, at least about 1 mg/kg, 2 mg/kg, 3 mg/kg, 4 mg/kg, 5 mg/kg, 6 mg/kg, 7 mg/kg, 8 mg/kg, 9 mg/kg, 11 mg/kg, at least about 12 mg/kg, at least about 13 mg/kg, at least about 14 mg/kg, at least about 15 mg/kg, at least about 16 mg/kg, at least about 17 mg/kg, at least about 18 mg/kg, at least about 19 mg/kg, at least about 20 mg/kg, at least about 21 mg/kg, at least about 22 mg/kg, at least about 23 mg/kg, at least about 24 mg/kg, at least about 25 mg/kg, at least about 26 mg/kg, at least about 27 mg/kg, at least about 28 mg/kg, at least about 29 mg/kg, at least about 30 mg/kg, least about 35 mg/kg, least about 40 mg/kg, least about 45 mg/kg, least about 50 mg/kg, least about 55 mg/kg, least about 60 mg/kg, least about 65 mg/kg, least about 70 mg/kg, least about 75 mg/kg, least about 80 mg/kg, or more inclusive of all ranges and subranges therebetween, per intravenous dose. Side effects associated with imipenem include, but are not limited to, nausea, vomiting, allergic reactions, and seizure (at high doses).

Gemcitabine (marked as GEMZAR), is a nucleoside metabolic inhibitor. It is indicated for treatment of ovarian cancer, breast cancer, non-small cell lung cancer, and pancreatic cancer. Normally, the dose is 250-2000 mg/m$^2$ IV. Methods of the present invention can allow using higher doses than the normal doses described herein, or using the same doses but with less side effects/toxicity. In some embodiments, the therapeutic effective amount of doxorubicin can be at least about 10 mg/kg, at least about 1 mg/kg, 2 mg/kg, 3 mg/kg, 4 mg/kg, 5 mg/kg, 6 mg/kg, 7 mg/kg, 8 mg/kg, 9 mg/kg, 11 mg/kg, at least about 12 mg/kg, at least about 13 mg/kg, at least about 14 mg/kg, at least about 15 mg/kg, at least about 16 mg/kg, at least about 17 mg/kg, at least about 18 mg/kg, at least about 19 mg/kg, at least about 20 mg/kg, at least about 21 mg/kg, at least about 22 mg/kg, at least about 23 mg/kg, at least about 24 mg/kg, at least about 25 mg/kg, at least about 26 mg/kg, at least about 27 mg/kg, at least about 28 mg/kg, at least about 29 mg/kg, at least about 30 mg/kg, least about 35 mg/kg, least about 40 mg/kg, least about 45 mg/kg, least about 50 mg/kg, least about 55 mg/kg, least about 60 mg/kg, least about 65 mg/kg, least about 70 mg/kg, least about 75 mg/kg, least about 80 mg/kg, or more inclusive of all ranges and subranges therebetween, per intravenous dose. Side effects associated with gemcitabine include, but are not limited to, flu-like symptoms, fever, fatigue, nausea (mild), vomiting, poor appetite, skin rash, and low blood counts.

Erlotinib (marked as TARCEVA), is an EGFR inhibitor. It is indicated for non-small cell lung cancer (NSCLC) and pancreatic cancer. Normally, the dose is 25-150 mg/day. Methods of the present invention can allow using higher doses than the normal doses described herein, or using the same doses but with less side effects/toxicity. In some embodiments, the therapeutic effective amount of doxorubicin can be at least about 1 mg/kg, 1.5 mg/kg, 2 mg/kg, 2.5 mg/kg, 3.0 mg/kg, 3.5 mg/kg, 4.0 mg/kg, 4.5 mg/kg, 5.0 mg/kg, 5.5 mg/kg, 6.0 mg/kg, 6.5 mg/kg, 7.0 mg/kg, 7.5 mg/kg, 8.0 mg/kg, 8.5 mg/kg, 9.0 mg/kg, 9.5 mg/kg, 10.0 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 21 mg/kg, 22 mg/kg, 23 mg/kg, 24 mg/kg, 25 mg/kg, 26 mg/kg, 27 mg/kg, 28 mg/kg, 29 mg/kg, 30 mg/kg, 40 mg/kg, 50 mg/kg, or more, inclusive of all ranges and subranges therebetween, per intravenous dose. Side effects associated with erlotinib include, but are not limited to, nausea, stomach upset, vomiting, loss of appetite, weight loss, diarrhea, mouth sores, and dry skin.

Methods of Attenuating Drug-Drug Interactions

The present invention can provide methods of attenuating interactions of a first drug (e.g., a first therapeutic agent) and a second drug (e.g., a second therapeutic agent) in a patient. As described herein, interactions of drugs, or drug-drug interactions, can refer to the changes of the effects of a drug or a pharmaceutical composition on a patient when the pharmaceutical composition is taken together with a second drug or second pharmaceutical composition. In some embodiments, the interactions can occur when more than two drugs are concurrently in a patient, regardless of the time between the administrations of the two or more drugs and thereby, and react with each other.

In some embodiments, as described herein, "attenuating interactions" of drugs refers to actions that result in reducing or preventing any types of interactions between two or more drugs or reducing the hypersensitivity, the toxicity, or adverse effects that are caused by the interactions of two or more drugs. In some embodiments, the interactions can include, but are not limited to, synergistic or antagonistic interactions. By way of examples, attenuating interactions of the drugs can be at least any one of the following scenarios: reducing and/or preventing drug-drug physical interactions, reducing and/or preventing drug-drug pharmacokinetic interactions, reducing and/or preventing the hypersensitivity caused by co-existence of the drugs, reducing and/or preventing the toxicity caused by co-existence of drugs, or reducing and/or preventing the antagonistic interactions of drugs.

In some embodiments, the effects of the attenuated interactions can be delayed, decreased, or enhanced absorption of either pharmaceutical composition, and thereby decreases or increases the action of either or both therapeutic agents or both pharmaceutical compositions. In some embodiments, the attenuated interactions can impact the transport or the distribution of the therapeutic agents or the pharmaceutical compositions. In some embodiments, such effects of interactions can occur between a drug and a food product including herbs. In some embodiments, such effects of interactions can occur between a drug and a vitamin.

In some embodiments, the present invention can attenuate the interactions of the drugs in a patient by administering to the patient a pharmaceutical composition comprising the first therapeutic agent. In some embodiments, the pharmaceutical compositions comprise therapeutically effective amounts of the first therapeutic agent that is mixed with blood products for a period of time (i.e., incubation time). In some embodiments, after the incubation, the mixtures of the first therapeutic agent and the blood products can be parenterally administered to the patient. In some embodiments, the parenteral administration is intravenous administration.

In some embodiments, the patient can be administered with at least a second drug (e.g., a second therapeutic agent). In some embodiments, the second drug can be administered to the patient prior to the administration of the pharmaceutical compositions of the invention. In some embodiments, the second drug can be administered to the patient subsequent to the administration of the pharmaceutical compositions. In some embodiments, the second drug can be administered to the patient concurrently with the administration of the pharmaceutical compositions. In some embodiments, the pharmaceutical agents and the pharmaceutical compositions can be administered in any manners that are suitable for therapeutic purposes. In some embodiments, the administrations of both the first drug and the second drug directly can induce drug-drug interactions. In some embodiments, the pharmaceutical compositions comprising a blood product and the first drug when administered with the second drug can reduce the occurrence of adverse effects. In some embodiments, the adverse effects can be caused by drug-drug interactions.

In some embodiments, the duration of time for incubating a blood product and the first drug can range any time as suitable so that the first drug is well mixed with the blood product by any means. In some embodiments, the duration time ranges from 1 minute to 4 hours, from 10 minutes to 3 hours, from 20 minutes to 2 hours, from 30 minutes to 1 hour, from 5 minutes to 3 hours, from 15 minutes to 4 hours, from 25 minutes to 3 hours, inclusive of all ranges and subranges therebetween. In some embodiments, the duration of time is about 20 minutes.

In some embodiments, a patient as described herein can have cancer. In some embodiments, the cancer can include, but is not limited to, brain cancer, bladder cancer, breast cancer, cervical cancer, cholangiocarcinoma, colon cancer, colorectal cancer, endometrial cancer, esophageal cancer, lung cancer, liver cancer, melanoma, ovarian cancer, pancreatic cancer, prostate cancer, rectal cancer, renal cancer, stomach cancer, testicular cancer, uterine cancer, Kaposi's sarcoma, leukemia, lymphoma, and acute lymphocytic leukemia. In some embodiments, the patient can have a microbial infection. In some embodiments, the patient suffers from sickle cell disease, pulmonary hypertension, or an ischemic condition.

In some embodiments, the reduction of the drug interactions can allow the administration of a higher therapeutic effective amount of the therapeutic agents. In some embodiments, the therapeutic effective amounts can be at least 10%, at least 20%, at least 30%, at least 40%, at least 50%, at least 60%, at least 70%, at least 80%, at least 90%, at least 100%, at least 200%, at least 300%, at least 400%, at least 500%, at least 600%, at least 700%, at least 800%, at least 900%, at least 1000%, or higher, inclusive of all ranges and subranges therebetween, higher than the administered amount of the therapeutic agents without incubation with the blood products.

In some embodiments, a first therapeutic agent in the pharmaceutical compositions of the present invention can have drug interactions with a second therapeutic agents as disclosed herein. By way of examples, doxorubicin can interact with verapamil when both drugs are concurrently in a patient and can cause acute toxicity of doxorubicin that lead to higher incidence and severity of degenerative changes in cardiac tissue. Doxorubicin can interact with cyclosporine when both drugs are concurrently in a patient and can result in increases in AUC (area under the curve) for both doxorubicin and doxorubicinol, the main toxic metabolite of doxorubicin, and thereby can cause profound and prolonged hematologic toxicity compared to doxorubicin when administered alone. Paclitaxel can interact with anti-convulsant therapy and cause the induction of cytochrome p450 enzyme and thereby leads to decreased paclitaxel plasma steady state concentrations.

In some embodiments, agents that can interact with doxorubicin include but are not limited to paclitaxel, progesterone, verapamil, cyclosporine, dexrazoxane, cytarabine, cyclophosphamide, phenobarbital, phenytoin, streptozocin, saquinavir, etoposide, and live vaccines. In some embodiments, the therapeutic effective amount of doxorubicin can be at least about 1.3 mg/m$^2$ to at least about 50 mg/m$^2$, at least about 1.5 mg/m$^2$ to at least about 45 mg/m$^2$, at least about 2.0 mg/m$^2$ to at least about 40 mg/m$^2$, at least about 2.5 mg/m$^2$ to at least about 35 mg/m$^2$, at least about 3.0 mg/m$^2$ to at least about 30 mg/m$^2$, at least about 3.5 mg/m$^2$ to at least about 25 mg/m$^2$, at least about 4.5 mg/m$^2$ to at least about 20 mg/m$^2$, at least about 5.5 mg/m$^2$ to at least about 15 mg/m$^2$, at least about 7.5 mg/m$^2$ to at least about 10 mg/m$^2$, at least about 15 mg/m$^2$, at least about 20 mg/m$^2$, at least about 30 mg/m$^2$, at least about 40 mg/m$^2$, at least about 50 mg/m$^2$, at least about 60 mg/m$^2$, at least about 70 mg/m$^2$, at least about 80 mg/m$^2$, at least about 90 mg/m$^2$, at least about 100 mg/m$^2$, or more, inclusive of all ranges and subranges therebetween, per intravenous dose.

In some embodiments, the adverse effects caused by the drug interactions between doxorubicin and the pharmaceutical agents can be cardiotoxicity, neutropenia, thrombocytopenia, degenerative changes in cardiac tissue, hematologic toxicity, lower tumor response rate, necrotizing colitis, cecal inflammation, bloody stools, infections, hemorrhagic cystitis, and acute myeloid leukemia. In some embodiments, the blood products that are incubated with doxorubicin can be erythrocytes, a mixture of packed red blood cells, a platelet, or whole blood. In some embodiments, the blood products that are incubated with doxorubicin are a mixture of packed red blood cells.

In some embodiments, agents that can interact with cisplatin include but are not limited to oral adenovirus types 4 and 7 live, adenovirus type 2 and type 5, amphotericin b deoxycholate, bacitracin, cidofovir, adjuvanted influenza virus vaccine trivalent, palifermin, pyridoxine, tofacitinib, acyclovir, adefovir, amikacin, belatacept, bendamustine, bumetanide, busulfan, capreomycin, carboplatin, carmustine, chlorambucil, cholera vaccine, cyclophosphamide, cyclosporine, colistin, dacarbazine, deflazacort, denosumab, dichlorphenamide, didanosine, elvitegravir, cobicistat, emtricitabine, tenofovir, ethotoin, fingolimod, foscarnet, fosphenytoin, furosemide, gentamicin, hydroxyurea, ifosfamide, influenza virus vaccine (h5n1), adjuvanted influenza virus vaccine (h5n1), ioversol, kanamycin, lomustine, mechlorethamine, melphalan, meningococcal group b vaccine, methotrexate, neomycin, nitazoxanide, ospemifene, oxaliplatin, paromomycin, pentamidine, peramivir, polymyxin b, polymyxin b, pyridoxine, rituximab, sipuleucel-t, sodium sulfate, potassium sulfate, magnesium sulfate, polyethylene glycol, streptomycin, streptozocin, tacrolimus, thiotepa, tobramycin, topotecan, vancomycin, zidovudine, magnesium oxide, paclitaxel protein bound, vinorelbine, vitamin A, vitamin E, taxanes, docetaxel, doxorubicin, epirubicin, and anticonvulsants.

In some embodiments, the therapeutic effective amount of cisplatin can be at least about 20 mg/m$^2$ to at least about 120 mg/m$^2$, at least about 25 mg/m$^2$ to at least about 110 mg/m$^2$, at least about 30 mg/m$^2$ to at least about 100 mg/m$^2$, at least about 35 mg/m$^2$ to at least about 95 mg/m$^2$, at least about 40 mg/m$^2$ to at least about 90 mg/m$^2$, at least about 45 mg/m$^2$ to at least about 85 mg/m$^2$, at least about 50 mg/m$^2$ to at least about 80 mg/m$^2$, at least about 55 mg/m$^2$ to at least about 75 mg/m$^2$, at least about 60 mg/m$^2$ to at least about 70 mg/m$^2$, at least about 35 mg/m$^2$ to at least about 100 mg/m$^2$, at least about 45 mg/m$^2$ to at least about 110 mg/m$^2$, at least about 65 mg/m$^2$ to at least about 120 mg/m$^2$, at least about 200 mg/m$^2$, at least about 300 mg/m$^2$, at least about 400 mg/m$^2$, at least about 500 mg/m$^2$, at least about 600 mg/m$^2$, at least about 700 mg/m$^2$, at least about 800 mg/m$^2$, at least about 900 mg/m$^2$, at least about 1000 mg/m$^2$, or more, inclusive of all ranges and subranges therebetween, per intravenous dose. In some embodiments, the adverse effects caused by the drug interactions between cisplatin and the pharmaceutical agents can be nephrotoxicity and ototoxicity. In some embodiments, the blood products that are incubated with cisplatin can be erythrocytes, a mixture of packed red blood cells, a platelet, or whole blood.

In some embodiments, agents that can interact with paclitaxel include but are not limited to taxanes, docetaxel, doxorubicin, epirubicin, anticonvulsants, phenytoin, carbamazepine, and phenobarbital. In some embodiments, the therapeutic effective amount of doxorubicin can be at least about 50 mg/m$^2$ to at least about 175 mg/m$^2$, at least about 60 mg/m$^2$ to at least about 160 mg/m$^2$, at least about 70 mg/m$^2$ to at least about 150 mg/m$^2$, at least about 80 mg/m$^2$ to at least about 140 mg/m$^2$, at least about 90 mg/m$^2$ to at least about 130 mg/m$^2$, at least about 100 mg/m$^2$ to at least about 120 mg/m$^2$, at least about 55 mg/m$^2$ to at least about 130 mg/m$^2$, at least about 75 mg/m$^2$ to at least about 115 mg/m$^2$, at least about 95 mg/m$^2$ to at least about 175 mg/m$^2$, at least about 200 mg/m$^2$, at least about 300 mg/m$^2$, at least about 400 mg/m$^2$, at least about 500 mg/m$^2$, at least about 600 mg/m$^2$, at least about 700 mg/m$^2$, at least about 800 mg/m$^2$, at least about 900 mg/m$^2$, at least about 1000 mg/m$^2$, or more, inclusive of all ranges and subranges therebetween, per intravenous dose.

In some embodiments, the blood products that are incubated with paclitaxel can be erythrocytes, a mixture of packed red blood cells, a platelet, or whole blood. In some embodiments, the blood products that are incubated with paclitaxel are platelets.

In some embodiments, agents that can interact with cyclophosphamide include, but are not limited to, oral adenovirus types 4 and 7 live, carbamazepine, etanercept, hydrochlorothiazide, idarubicin, idelalisib, adjuvanted influenza virus vaccine trivalent, ivacaftor, palifermin, tofacitinib, allopurinol, antithrombin iii, argatroban, axitinib, belatacept, bendamustine, bivalirudin, butabarbital, carboplatin, carmustine, chlorambucil, cholera vaccine, cisplatincrofelemer, dabrafenib, decarbazine, dalteparin, daunorubicin liposomal, digoxin, doxorubicin liposomal, elvitegravir/cobicistat/emtricitabine/tenofovir, enoxaparin, fingolimod, flibanserin, fondaparinux, heparin, hydroxyurea, ifosfamide, iloperidone, influenza virus vaccine (h5n1), influenza virus vaccine (h5n1), adjuvanted, lomitapide, lomustine, lumacaftor/ivacaftor, mechlorethamine, melphalan, meningococcal group b vaccine, mifepristone, mitotane, ocrelizumab, oxaliplatin, pentobarbital, phenobarbital, primidone, ritonavir, secobarbital, sipuleucel-t, sorafenib, streptozocin, succinylcholine, thiotepa, tinzaparin, warfarin, lepirudin, and ruxolitinib.

In some embodiments, the therapeutic effective amount of cyclophosphamide can be at least about 1 mg/kg body weight per day, at least about 2 mg/kg body weight per day, at least 3 mg/kg body weight per day, at least about 4 mg/kg body weight per day, or at least about 5 mg/kg body weight per day, at least about 10 mg/kg body weight per day, at least about 15 mg/kg body weight per day, at least about 20 mg/kg body weight per day, at least about 25 mg/kg body weight per day, at least about 30 mg/kg body weight per day, at least about 35 mg/kg body weight per day, at least about 40 mg/kg body weight per day, at least about 45 mg/kg body weight per day, at least about 50 mg/kg body weight per day, inclusive of all ranges and subranges therebetween. In some embodiments, the blood products that are incubated with cyclophosphamide can be erythrocytes, a mixture of packed red blood cells, a platelet, or whole blood.

In some embodiments, agents that can interact with topotecan include, but are not limited to, abiraterone, oral adenovirus types 4 and 7 live, amiodarone, atorvastatin, azithromycin, captopril, carvedilol, clarithromycin, cobicistat, conivaptan, crizotinib, cyclosporine, darunavir, dipyridamole, dronedarone, erythromycin base, erythromycin ethylsuccinate, erythromycin lactobionate, erythromycin stearate, felodipine, influenza virus vaccine trivalent, adjuvanted, itraconazole, ivacaftor, ketoconazole, Lapatinib, ledipasvir/sofosbuvir, lomitapide, lopinavir, mefloquine, nelfinavir, nicardipine, Nilotinib, quercetin, quinidine, quinine, ranolazine, Ritonavir, saquinavir, sofosbuvir/velpatasvir, tacrolimus, tamoxifen, ticagrelor, tolvaptan, vandetanib, vemurafenib, verapamil, belatacept, cholera vaccine, cisplatin, daclatasvir, denosumab, diltiazem, eliglustat, eltrombopag, eluxadoline, fingolimod, hydroxyurea, meningococcal group b vaccine, ombitasvir/paritaprevir/ritonavir, osimertinib, ponatinib, regorafenib, rolapitant, safinamide, sipuleucel-t, vitamin A, vitamin D, and vitamin E.

In some embodiments, the therapeutic effective amount of topotecan can be at least about 0.75 mg/m$^2$ to at least about 1.5 mg/m$^2$, at least about 1 mg/m$^2$ to at least about 1.3 mg/m$^2$, at least about 0.9 mg/m$^2$ to at least about 1.1 mg/m$^2$, at least about 0.8 mg/m$^2$ to at least about 1 mg/m$^2$, at least about 5 mg/m$^2$, at least about 10 mg/m$^2$, at least about 15 mg/m$^2$, at least about 20 mg/m$^2$, at least about 25 mg/m$^2$, at least about 30 mg/m$^2$, inclusive of all ranges and subranges therebetween, per intravenous dose. In some embodiments, the blood products that are incubated with cisplatin can be erythrocytes, a mixture of packed red blood cells, a platelet, or whole blood.

In some embodiments, agents that can interact with ifosfamide include, but are not limited to, oral adenovirus types 4 and 7 live, bacitracin, efavirenz, idelalisib, adjuvanted influenza virus vaccine trivalent, ivacaftor, palifermin, tofacitinib, atazanavir, axitinib, belatacept, bendamustine, busulfan, carboplatin, carmustine, chlorambucil, cholera vaccine, cisplatin, crizotinib, cyclophosphamide, dabrafenib, dacarbazine, darunavir, denosumab, dichlorphenamide, elvitegravir/cobicistat/emtricitabine/tenofovir, eslicarbazepine acetate, etravirine, fingolimod, flibanserin, fosamprenavir, hydroxyurea, iloperidone, indinavir, influenza virus vaccine (h5n1), influenza virus vaccine (h5n1), adjuvanted, lomitapide, lomustine, lopinavir, lumacaftor/ivacaftor, mechlorethamine, melphalan, meningococcal group b vaccine, mitotane, nelfinavir, oxaliplatin, paclitaxel, paclitaxel protein bound, peramivir, ritonavir, saquinavir, sipuleucel-t, streptozocin, thiotepa, tipranavir, ruxolitinib, vitamin A, vitamin D, and vitamin E.

In some embodiments, the therapeutic effective amount of ifosfamide can be at least about 0.5 mg/m$^2$, at least about 1 mg/m$^2$, at least about 1.5 mg/m$^2$, at least about 2.0 mg/m$^2$, at least about 3.0 mg/m$^2$, at least about 4.0 mg/m$^2$, at least about 5.0 mg/m$^2$, at least about 6.0 mg/m$^2$, at least about 7.0 mg/m$^2$, at least about 8.0 mg/m$^2$, at least about 9.0 mg/m$^2$, at least about 10 mg/m$^2$, at least about 15 mg/m$^2$, inclusive of all ranges and subranges therebetween, per intravenous dose. In some embodiments, the therapeutic effective amount of topotecan is at least about 1.2 grams/m$^2$ per intravenous dose. In some embodiments, the blood products that are incubated with ifosfamide can be erythrocytes, a mixture of packed red blood cells, a platelet, or whole blood.

In some embodiments, agents that can interact with irinotecan include, but are not limited to, clozapine, conivaptan, darunavir, delavirdine, fosamprenavir, indinavir, itraconazole, lopinavir, ritonavir, st john's wort, adenovirus types 4 and 7 live, oral, armodafinil, atazanavir, bosentan, carbamazepine, cimetidine, clarithromycin, clobazam, crizotinib, dasabuvir, efavirenz, eliglustat, enzalutamide, erythromycin base, erythromycin ethylsuccinate, erythromycin lactobionate, eslicarbazepine acetate, etravirine, fosphenytoin, gemfibrozil, idelalisib, indinavir, influenza virus vaccine trivalent, adjuvanted, isoniazid, ivacaftor, ketoconazole, milk thistle, mitotane, modafinil, nafcillin, nefazodone, nelfinavir, nevirapine, ombitasvir/paritaprevir/ritonavir & dasabuvir, oxcarbazepine, phenobarbital, phenytoin, posaconazole, primidone, rifabutin, rifampin, rifapentine, ritonavir, saquinavir, sertraline, st john's wort, telithromycin, tetracycline, tipranavir, verapamil, voriconazole, Monitor Closely (54), Amiodarone, Aprepitant, Atorvastatin, Bevacizumab, Bicalutamide, Bosutinib, Ceritinib, cholera vaccine, clotrimazole, crizotinib, cyclosporine, dabrafenib, daclatasvir, denosumab, desipramine, dexamethasone, dichlorphenamide, diltiazem, dronedarone, eluxadoline, elvitegravir/cobicistat/emtricitabine/tenofovir, erythromycin base, erythromycin ethylsuccinate, erythromycin lactobionate, erythromycin stearate, fingolimod, fluconazole, hydroxyurea, imatinib, ketoconazole, lapatinib, lomitapide, lumacaftor/ivacaftor, meningococcal group b vaccine, mifepristone, nicardipine, nilotinib, norfloxacin, ombitasvir/paritaprevir/ritonavir, osimertinib, pentobarbital, ponatinib, ranolazine, regorafenib, rifampin, rolapitant, safinamide, schisandra, sipuleucel-t, sofosbuvir/velpatasvir, sorafenib, tacrolimus, vemurafenib, verapamil, Minor (7), Haloperidol, Iloperidone, Metronidazole, netupitant/palonosetron, valerian, vitamin A, and vitamin E.

In some embodiments, the blood products that are incubated with irinotecan can be erythrocytes, a mixture of packed red blood cells, plasma, platelets, or whole blood.

In some embodiments, the present methods of attenuating drug interactions can have chemoprotective effects. In some embodiments, "chemoprotection" can refer to the capability of reducing or protecting normal tissues from the adverse effects of anti-cancer agents. In some embodiments, chemoprotection can refer to reducing the adverse effects in a patient administered with an anti-cancer agent by at least 10%, at least 15%, at least 20%, at least 30%, at least 40%, at least 50%, at least 60%, at least 70%, at least 80%, at least 90%, at least 100%, at least 300%, at least 400%, or more, inclusive of all ranges and subranges therebetween, compared to the patient under conventional circumstances.

In some embodiments, the present methods of attenuating drug interactions can have radioprotective effects. In some embodiments, "radioprotection" can refer to the capabilities of reducing or protecting normal tissues from the adverse effects of anti-cancer radioactive therapies. In some embodiments, radioprotection can refer to reducing the adverse effects in a patient administered with an radioactive therapy by at least 10%, at least 15%, at least 20%, at least 30%, at least 40%, at least 50%, at least 60%, at least 70%, at least 80%, at least 90%, at least 100%, at least 300%, at least 400%, or more, inclusive of all ranges and subranges therebetween, compared to the patient under conventional circumstances.

In some embodiments, the present methods of attenuating drug interactions can have radiochemoprotective effects. In some embodiments, "radiochemoprotection" can refer to the capability of reducing or protecting normal tissues from the adverse effects of combination of a chemotherapy and a radioactive therapy. In some embodiments, radiochemoprotection can refer to reducing the adverse effects in a patient administered with a chemotherapy and an radioactive therapy by at least 10%, at least 15%, at least 20%, at least 30%, at least 40%, at least 50%, at least 60%, at least 70%, at least 80%, at least 90%, at least 100%, at least 300%, at least 400%, or more, inclusive of all ranges and subranges therebetween, compared to the patient under conventional circumstances.

III. Exemplary Pharmaceutical Compositions for Administration

Another aspect of the invention provides a pharmaceutical composition, comprising a blood product and one or more therapeutic agents, wherein the therapeutic agent is an anthracycline anti-cancer agent, a topoisomerase inhibitor, an oxazaphosphinanyl anti-cancer agent, a nitro-aryl anti-cancer agent, a thiol-reactive functional-group agent, a nitric oxide modulator, a platinum-based antineoplastic compound, acrylamide, acrylonitrile, bis(4-fluorobenzyl)trisulfide, a cardiac glycoside, an anti-mitotic agent, a nucleoside analog, an EGFR inhibitor, or an anti-microbial agent.

Another aspect of the invention provides a pharmaceutical composition, comprising a blood product and one or more therapeutic agents, wherein the therapeutic agent is an anthracycline anti-cancer agent, a topoisomerase inhibitor, an oxazaphosphinanyl anti-cancer agent, a nitro-aryl anti-cancer agent, a thiol-reactive functional-group agent, a nitric oxide modulator, a platinum-based antineoplastic compound, acrylamide, acrylonitrile, bis(4-fluorobenzyl)trisulfide, a cardiac glycoside, an anti-mitotic agent, a nucleoside analog, or an anti-microbial agent.

Another aspect of the invention provides a pharmaceutical composition comprising a blood product and one or more therapeutic agents, wherein the therapeutic agent is an anthracycline anti-cancer agent, a topoisomerase inhibitor, an oxazaphosphinanyl anti-cancer agent, a nitro-aryl anti-cancer agent, a thiol reactive functional group agent, an nitric oxide modulator, a platinum based compound, acrylamide, acrylonitrile, bis(4-fluorobenzyl)trisulfide, a cardiac glycoside, an anti-mitotic agent, an alkylating agent, a nucleoside analog, or an antimicrobial agent.

Another aspect of the invention provides a pharmaceutical composition, comprising a blood product and one or more therapeutic agents, wherein the therapeutic agent is an anthracycline anti-cancer agent, a topoisomerase inhibitor, an oxazaphosphinanyl anti-cancer agent, a nitro-aryl anti-cancer agent, a thiol-reactive functional-group agent, a nitric oxide modulator, a platinum-based antineoplastic compound, acrylamide, acrylonitrile, bis(4-fluorobenzyl)trisulfide, a cardiac glycoside, an anti-mitotic agent, or an anti-microbial agent.

Another aspect of the invention provides a pharmaceutical composition, comprising a blood product and one or more therapeutic agents, wherein the therapeutic agent is an anthracycline anti-cancer agent, a topoisomerase inhibitor, an oxazaphosphinanyl anti-cancer agent, a nitro-aryl anti-cancer agent, a thiol reactive functional group agent, an nitric oxide modulator, a platinum based compound, acrylamide, acrylonitrile, bis(4-fluorobenzyl)trisulfide, a cardiac glycoside, an anti-mitotic agent, an alkylating agent, or an antimicrobial agent.

Another aspect of the invention provides a pharmaceutical composition formulated for parenteral administration, comprising (i) a blood product and (ii) a therapeutic agent selected from the group consisting of an anthracycline anti-cancer agent, a topoisomerase inhibitor, an oxazaphosphinanyl anti-cancer agent, a nitro-aryl anti-cancer agent, a halo-aliphatic alkylating agent, an organo-nitrate ester compound, an organo-platinum compound, cis-platin, sodium nitroprusside, acrylamide, acrylonitrile, bis(4-fluorobenzyl) trisulfide, a phosphodiesterase inhibitor, a cardiac glycoside, and an anti-malarial agent.

In some embodiments, the invention provides a pharmaceutical composition comprising:
a. whole blood in an amount of at least 60% v/v of the formulation;
b. at least one therapeutic agent (described herein) in an amount of at least 10 µg/mL in the pharmaceutical composition; and
c. an anticoagulant.

The pharmaceutical compositions described herein may be characterized based on the identity of the blood product, identity of the therapeutic agent, and other features. For example, in certain embodiments, the blood product comprises erythrocyte cells. In certain embodiments, the blood product is a mixture of packed red blood cells. In certain embodiments, the blood product is whole blood. In certain embodiments, the whole blood is autologous whole blood. In certain embodiments, the whole blood is allogenic whole blood.

In certain embodiments, the blood product includes one or more types of cells. In certain embodiments, the blood product comprises erythrocyte cells. In certain embodiments, the blood product comprises platelets. In certain embodiments, the blood product comprises white cells. In certain embodiments, the blood product includes one or more of neutrophils, basophils, eosinophils, or dendritic cells. In certain embodiments, the blood product includes any applicable combination of types of cells. By way of examples, in certain embodiments, the blood product includes erythrocytes and platelets. In certain embodiments, the blood product includes erythrocytes and white blood cells. In certain embodiments, the blood product includes packed red blood cells, white blood cells, and platelets.

In certain embodiments, the blood product comprises plasma. In certain embodiments, the blood product comprises or consists of a buffy coat. In certain embodiments, the blood product comprises or consists of platelet rich plasma.

In certain embodiments, no component in the blood product (e.g., the red blood cells) is modified. Modifications of the blood product include but are not limited to genetically engineered expression of a target-binding agent or addition of a molecular marker, a fusion molecule, a photosensitive agent, a positive marker, a target recognition moiety, or an antibody aptamer; or manipulating the cells by electroporation, conjugation, endocytosis or hypo-osmotic dialysis. In certain embodiments, the blood product comprises erythrocyte cells, and the erythrocyte cells have not undergone any manipulation selected from the group consisting of genetic modification, electroporation, conjugation through biotin, conjugation to a cell-penetrating peptide, conjugation to hemoglobin, dimethyl sulfoxide osmotic pulse, endocytosis and hypotonic preswelling, hypotonic dilution, and hypo-osmotic dialysis.

Exemplary Features of the Pharmaceutical Compositions

The pharmaceutical compositions may be characterized according to, for example, the identity of the therapeutic agent, anticoagulant, concentration of therapeutic agent, amount of whole blood and other features described herein.

Identity of the Therapeutic Agent

The pharmaceutical compositions may be characterized according to the identity of the therapeutic agent. Accordingly, in certain embodiments, the therapeutic agent is an anthracycline anti-cancer agent. In certain embodiments, the anthracycline anti-cancer agent is doxorubicin, daunorubicin, idarubicin, liposomal doxorubicin, or any combination thereof. In certain embodiments, the anthracycline anti-cancer agent comprises doxorubicin. In certain embodiments, the anthracycline anti-cancer agent comprises epirubicin. In certain embodiments, the therapeutic agent is a topoisomerase inhibitor. In certain embodiments, the topoisomerase inhibitor is irinotecan, topotecan, etoposide, teniposide, mitoxantrone, or any combination thereof. In certain embodiments, the topoisomerase inhibitor comprises topotecan. In certain embodiments, the topoisomerase inhibitor comprises irinotecan. In certain embodiments, the therapeutic agent is an oxazaphosphinanyl anti-cancer agent. In certain embodiments, the oxazaphosphinanyl anti-cancer agent is ifosfamide, cyclophosphamide, trofosfamide, or any combination thereof. In certain embodiments, the oxazaphosphinanyl anti-cancer agent comprises ifosfamide. In certain embodiments, the oxazaphosphinanyl anti-cancer agent is cyclophosphamide. In certain embodiments, the therapeutic agent is a nitro-aryl anti-cancer agent. In certain embodiments, the nitro-aryl anti-cancer agent comprises iniparib or 2,4,6-trinitrotoluene. In certain embodiments, the nitro-aryl anti-cancer agent comprises iniparib. In certain embodiments, the therapeutic agent is a thiol-reactive functional-group agent that is a halo-aliphatic alkylating agent. In certain embodiments, the therapeutic agent is a halo-aliphatic alkylating agent. In certain embodiments, the halo-aliphatic alkylating agent comprises 3-bromopyruvate, 2-iodoacetamide, 2-bromoacetamide, iodoacetic acid, or bromoacetic acid. In certain embodiments, the therapeutic agent is an organo-nitrate ester compound. In certain embodiments, the organo-nitrate ester compound comprises nitroglycerin. In certain embodiments, the therapeutic agent is an organo-platinum compound. In certain embodiments, the organo-platinum compound comprises carboplatinum. In certain embodiments, the therapeutic agent is cis-platin, sodium nitroprusside, acrylamide, acrylonitrile, or bis(4-fluorobenzyl)trisulfide. In certain embodiments, the therapeutic agent is a phosphodiesterase inhibitor. In certain embodiments, the phosphodiesterase inhibitor comprises avanafil, lodenafil, mirodenafil, sildenafil, tadalafil, vardenafil, udenafil, or zaprinast. In certain embodiments, the therapeutic agent is a cardiac glycoside (e.g., digoxin or digitoxin). In certain embodiments, the cardiac glycoside is digoxin, digitoxin, ouabain, or oleandrin.

In certain embodiments, the therapeutic agent is an EGFR inhibitor. In certain embodiments, the EGFR inhibitor is erlotinib, gefitinib, lapatinib, vandetanib, neratinib, or osimertinib. In certain embodiments, the therapeutic agent is a nucleoside analog. In certain embodiments, the nucleoside analog is gemcitabine, didanosine, vidarabine, cytarabin, emtricitabine, lamivudine, zalcitabine, abacavir, acyclovir, entecavir, idoxuridine, trifluridine, or any combination thereof. In certain embodiments, the therapeutic agent is a thiol-reactive functional-group agent. In certain embodiments, the thiol-reactive functional-group agent is selected from the group consisting of 3-bromopyruvate, 2-iodoacetamide, 2-bromoacetamide, chloroacetic acid, iodoacetic acid, chloroacetamide, bromoacetic acid, maleimide, vinyl pyridine, disulfide, pyridyl disulfide, isocyanate, and isothiocyanate. In certain embodiments, the thiol-reactive functional-group agent is selected from the group consisting of maleimide, vinyl pyridine, disulfide, pyridyl disulfide, isocyanate, and isothiocyanate. In certain embodiments, the therapeutic agent is an anti-mitotic agent. In certain embodiments, the anti-mitotic agent is paclitaxel.

In certain embodiments, the therapeutic agent is a nitric oxide modulator. In certain embodiments, the nitric oxide modulator is nitroglycerin, nitroprusside, diethylamine/NO, diethylenetriamine/NO, amyl nitrite, isosorbide dinitrate, isosorbide 5-mononitrate, nicorandil, nitroaspirins, S-nitroso-NSAIDs, phosphodiesterase inhibitors, ACE inhibitors, calcium channel blockers, statins, or any combination thereof. In certain embodiments, the therapeutic agent is a nitric oxide modulator that is an organo-nitrate ester compound. In certain embodiments, the therapeutic agent is a nitric oxide modulator that is a phosphodiesterase inhibitor. In certain embodiments, the nitric oxide modulator is nitroglycerin, sodium nitroprusside, or a phosphodiesterase inhibitor.

In certain embodiments, the therapeutic agent is a platinum-based antineoplastic compound. In certain embodiments, the platinum-based antineoplastic compound is cisplatin, nedaplatin, triplatin tetranitrate, phenanthriplatin, picoplatin, satraplatin, carboplatin, oxaliplatin, or any combination thereof. In certain embodiments, the platinum-based antineoplastic compound is cisplatin, carboplatin, oxaliplatin, nedaplatin, or any combination thereof. In certain embodiments, the platinum-based antineoplastic compound comprises carboplatinum. In certain embodiments, the platinum-based antineoplastic compound comprises oxaliplatin.

In certain embodiments, the therapeutic agent is a topoisomerase inhibitor. In certain embodiments, the topoisomerase inhibitor is a type I topoisomerase inhibitor. In certain embodiments, the type I topoisomerase inhibitor is irinotecan or topotecan. In certain embodiments, the topoisomerase inhibitor is a type II topoisomerase inhibitor. In certain embodiments, the type II topoisomerase inhibitor is an anthracycline, etoposide, teniposide, or nitoxantrone. In certain embodiments, the type II topoisomerase inhibitor is etoposide, teniposide, or nitoxantrone.

In some embodiments, the therapeutic agent is doxorubicin. In some embodiments, the therapeutic agent is adriamycin. In some embodiments, the therapeutic agent is cisplatin. In some embodiments, the therapeutic agent is paclitaxel. In some embodiments, the therapeutic agent is cyclophosphamide. In some embodiments, the therapeutic agent is topotecan. In some embodiments, the therapeutic agent is ifosfamide. In some embodiments, the therapeutic agent is irinotecan. In some embodiments, the therapeutic agent is digoxin.

In certain embodiments, the therapeutic agent is an anti-microbial agent. In certain embodiments, the anti-microbial agent is an antibiotic, an antiviral agent, an anti-fungal agent, or an anti-parasitic agent. In certain embodiments, the anti-microbial agent is an antibiotic. In certain embodiments, the antibiotic is vancomycin. In certain embodiments, the antibiotic is imipenem. In certain embodiments, the anti-microbial agent is an antiviral agent. In certain embodiments, the anti-microbial agent is an anti-fungal agent. In certain embodiments, the anti-microbial agent is an anti-parasitic agent. In certain embodiments, the anti-microbial agent is an anti-malarial agent. In certain embodiments, the anti-malarial agent is artemisinin, artesunate, quinine, quinidine, hydroxychloroquine, primaquine, lumefantrine, atovaquone, dapsone, proguanil, chloroquine, sulfadoxine-pyrimethamine, mefloquine, piperaquine, or amodiaquine. In certain embodiments, the anti-malarial agent is artemisinin. In certain embodiments, the therapeutic agent is for sepsis treatment (e.g., imipenem).

In certain embodiments, the antibiotic is aminoglycoside; amikacin; gentamicin; kanamycin; neomycin; netilmicin; steptomycin; tobramycin; ansamycin; geldanamycin; herbimycin; carbacephem; loracarbef; carbacepenem; ertapenem; doripenem; imipenem/cilastatin; meropenem; cephalosporin; cefadroxil; cefazolin; cefalotin or cefalothin; cefalexin; cefaclor; cefamandole; cefoxitin; cefprozil; cefuroxime; cefixime; cefdinir; cefditoren; cefoperazone; cefotaxime; cefpodoxime; ceftazidime; ceftibuten; ceftizoxime; ceftriaxone; cefepime; ceftobiprole; glycopeptide; teicoplanin; vancomycin; macrolides; azithromycin; clarithromycin; dirithromycin; erythromycin; roxithromycin; troleandomycin; telithromycin; spectinomycin; monobactam; aztreonam; penicillins; amoxicillin; ampicillin; azlocillin; carbenicillin; cloxacillin; dicloxacillin; flucloxacillin; mezlocillin; meticillin; nafcillin; oxacillin; penicillin, piperacillin, ticarcillin; bacitracin; colistin; polymyxin B; quinolone; ciprofloxacin; enoxacin; gatifloxacin; levofloxacin; lomefloxacin; moxifloxacin; norfloxacin; ofloxacin; trovafloxacin; sulfonamide; mafenide; prontosil; sulfacetamide; sulfamethizole; sufanilimide; sulfasalazine; sulfisoxazole; trimethoprim; trimethoprim-sulfamethoxazole (co-trimoxazole) (TMP-SMX); tetracycline; demeclocycline; doxycycline; minocycline; oxytetracycline; tetracycline; arsphenamine; chloramphenicol; clindamycin; lincomycin; ethambutol; fosfomycin; fusidic acid; furazolidone; isoniazid; linezolid; metronidazole; mupirocin; nitrofuantoin; platensimycin; purazinamide; quinupristin/dalfopristin; rifampin or rifampicin; tinidazole; or dapsone.

In some embodiments, the antibiotic is Aclacinomycin A, Acylovir, Aklomide, Amantadine, Amikacin sulfate, Amoxicillin/clavulanate, Amprolium, Arbekacin, Atovaquone, Avermectin, Azathioprine, Azthromycin, Aztreinam, Bacampicilline-HCL, Arsphenamine, Bambermycin, Bialaphos, Bleomycin sulfate, Bradykinin antagonist, Carbadox, Carbarsone, Carbenicillin indanyl, Carboplatin, carminomycin, Clavulanic acid, Chloramphenicol, Clofazimine, Clopidol, Clotrimazole, Colistmethate sodium, colistin sulfate, cyclophosphamide, cycloserine, cyclospotin, cytarabine, Dactinomycin, Daunorubicin-HCL, Daunorubicin-liposomal, Demeclocycline-HCL, Docetaxel, Doxorubicin-HCL, Efrotomycin, Epirubicin, Ethambutol-HCL, Ethionamide, Etiposide, Famciclovir, Flomoxef, floxacillin, Fluconazole oral, Flucytosine, Fludarabine phosphate, Fluorouracil, Flurithromucin, Fluvastatin, Foscarnet sodium, Fosfomycin, Furazolidone, Ganciclovir sodium, Gentamycin sulfate, Gosserelin acetate, Gramicidin, Halofuginone HBr, Hygromycin B, Idarubicine-HCL, Idoxuridine Ifosfamide, Indinavir, Lincomycin, Ethambutol, Fosfomycin, Fusidic acid, Furazolidone, Isoniazid, Linezolid, Metronidazole, Mezlocillin sodium, Miconazole, Mibemectin, Milbemycins, Minocycline, Miocamycin, Mitomycin C, Mitotane, Mitoxantrone-HCl, Monensin sodium, Mupirocin, Nafcillin, Nalidixic acid, Narasin, Natamycin, Neomycin sulfate, Nevirapine, Nicarbazine, Niclosamide, Nisin, Nitrofurazone, Nitromide, Norfloxacin, Novobiocin sodium, Nystatin, Oleandomycin, Omeprazole, Oxiconazole nitrate, Oxytetracycline, Mupirocin, Nitrofurantoin, Paclitaxel, Pentamidine isethionate, Pentostatin, Phosphinothricin, Plicamycin, Pravastinamycin, Pyrantel tartrate, Pyrazinamide, Platensimycin, Pyrazinamide, Quinupristin/Dalfopristin, Rifampin (Rifampin in US), Ribavirin, Sulfamethoxazole, Sulfanitran, Sulfathiazole, Sultamicillin, Tacrolimus (FK506), Taxobactam, Tenipocide, Terbinafine-HCl, Thiabendazole, Thiamphenicol, Thioguanine, Thiotepa, Tiamulin H-fumarate, Ticarcillin disodium, Tolnaftate, Topotecan, Trimetrexate glucuronate, troleandomycin, Tylosin phosphate, Tinidazole, Uracil mustard, Valacyclovir-HCl, Vancomycin-HCl, Vidarabene, Vinblastine sulfate, Vincristine sulfate, Vinorelbine tartrate, Virginiamycin, Zalcitabine, Zidovudine, or those described in in Strohl (Biotechnology of antibiotics, Informa Health Care, 1997, ISBN 0824798678, 9780824798673), Laskin et al. (Antibiotics, CRC Press, 1982, ISBN 0849372046, 9780849372049), Hash (Antibiotics, Academic Press, 1975, ISBN 0121819434, 9780121819439), and U.S. Pat. Nos. 5,998,581, 6,166,012, 6,218,138, 6,218,368, 6,224,864, 6,224,891, 6,287,813, 6,316,033, 6,331,540, 6,333,305, 6,337,410, 6,350,738, 6,352,983, 6,379,651, 6,380,172, 6,380,245, 6,380,356, 6,391,851, 6,399,086, 6,410,059, 6,437,119, 6,458,776, 6,462,025, 6,475,522, 6,486,148, 6,514,962, 6,518,243, 6,537,985, 6,544,502, 6,544,555, 6,551,591, 6,552,020, 6,565,882, 6,569,830, 6,586,393, 6,596,338, 6,599,885, 6,610,328, 6,623,757, 6,623,758, 6,623,931, 6,627,222, 6,630,135, 6,632,453, 6,638,532, 6,653,469, 6,663,890, 6,663,891, 6,667,042, 6,667,057, 6,669,842, 6,669,948, 6,716,962, 6,723,341, 6,727,232, 6,730,320, 6,747,012, 6,750,038, 6,750,199, 6,767,718, 6,767,904, 6,780,616, 6,780,639, 6,784,204, 6,784,283, 6,787,568, 6,821,959, 6,858,584, 6,861,230, 6,875,752, 6,913,764, 6,914,045, 6,921,810, 6,930,092, 6,942,993, 6,964,860, 6,974,585, 6,982,247, 6,991,807, 7,008,663, 7,018,996, 7,026,288, 7,030,093, 7,049,097, 7,067,483, 7,078,195, 7,078,377, 7,109,190, 7,115,576, 7,115,753, 7,122,204, 7,122,514, 7,138,487, 7,169,756, 7,202,339, 7,205,412, 7,211,417, 7,244,712, 7,271,147, 7,271,154, 7,273,723, 7,307,057, 7,385,101, 7,396,527, 7,407,654, 7,419,781, 7,485,294, 7,544,364, 7,569,677 or RE39743.

In certain embodiments, the antiviral agent is thiosemicarbazone; metisazone; nucleoside and/or nucleotide; acyclovir; idoxuridine; vidarabine; ribavirin; ganciclovir; famciclovir; valaciclovir; cidofovir; penciclovir; valganciclovir; brivudine; ribavirin, cyclic amines; rimantadine; tromantadine; phosphonic acid derivative; foscarnet; fosfonet; protease inhibitor; saquinavir; indinavir; ritonavir; nelfinavir; amprenavir; lopinavir; fosamprenavir; atazanavir; tipranavir; nucleoside and nucleotide reverse transcriptase inhibitor; zidovudine; didanosine; zalcitabine; stavudine; lamivudine; abacavir; tenofovir disoproxil; adefovir dipivoxil; emtricitabine; entecavir; non-nucleoside reverse transcriptase inhibitor; nevirapine; delavirdine; efavirenz; neuraminidase inhibitor; zanamivir; oseltamivir; moroxydine; inosine pranobex; pleconaril; or enfuvirtide.

In certain embodiments, the anti-fungal agent is allylamine; terbinafine; antimetabolite; flucytosine; azole; fluconazole; itraconazole; ketoconazole; ravuconazole; posaconazole; voriconazole; glucan synthesis inhibitor; caspofungin; micafungin; anidulafungin; polyenes; amphotericin B; amphotericin B Lipid Complex (ABLC); amphotericin B Colloidal Dispersion (ABCD); liposomal amphotericin B (L-AMB); liposomal nystatin; or griseofulvin.

In certain embodiments, the anti-parasitic agent is eflornithine; furazolidone; melarsoprol; metronidazole; ornidazole; paromomycin sulfate; pentamidine; pyrimethamine; tinidazole; antimalarial agent; quinine; chloroquine; amodiaquine; pyrimethamine; sulphadoxine; proguanil; mefloquine; halofantrine; primaquine; artemesinin and derivatives thereof; doxycycline; clindamycin; benznidazole; nifurtimox; antihelminthic; albendazole; diethylcarbamazine; mebendazole; niclosamide; ivermectin; suramin; thiabendazole; pyrantel pamoate; levamisole; piperazine family; praziquantel; triclabendazole; octadepsipeptide; or emodepside.

Anticoagulant

The pharmaceutical composition may be characterized according to the identity and/or amount of the anticoagulant. Accordingly, in certain embodiments, the anticoagulant comprises one or more of heparin and a citrate salt. In certain embodiments, the anticoagulant is present in the pharmaceutical composition in an amount ranging from about 0.1% wt/wt to about 15% wt/wt. In certain embodiments, the anticoagulant is present in the pharmaceutical composition in an amount ranging from about 1% wt/wt to about 10% wt/wt. In certain embodiments, the anticoagulant is present in the pharmaceutical composition in an amount ranging from about 2% wt/wt to about 8% wt/wt. In certain embodiments, the pharmaceutical composition consists essentially of the blood product, the therapeutic agent, and an anticoagulant.

Osmolality Adjusting Agent and/or Excipient

The pharmaceutical composition may be characterized according to the identity and/or amount of an osmolality adjusting agent. Accordingly, in certain embodiments, the pharmaceutical composition contains an osmolality adjusting agent to increase the osmolality. In certain embodiments, the osmolality adjusting agent is sodium chloride.

The pharmaceutical composition may be characterized according to the identity and/or amount of an excipient. Accordingly, in certain embodiments, the pharmaceutical composition contains an excipient. In certain embodiments, the excipient is N-methyl-2-pyrrolidone, dimethylacetamide, dimethylsulfoxide (DMSO), glycerol, urea, water, propylene glycol, urea, ethanol, Cremophor EL, Cremophor RH 40, Cremophor RH 60, d-alpha-tocopherol polyethylene glycol 1000 succinate, polysorbate 20, polysorbate 80, Solutol HS 15, sorbitan monooleate, poloxamer 407, Labrafil M-1944CS, Labrafil M-2125CS, Labrasol, Gellucire 44/14, Softigen 767, and mono- and di-fatty acid esters of PEG 300, 400, or 1750, glyceryl monooleate, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil and palm seed oil, beeswax, d-alpha-tocopherol, oleic acid, medium-chain mono- and diglycerides, hydrogenated soy phosphatidylcholine, distearoylphosphatidylglycerol, L-alpha-dimyristoylphosphatidylcholine, and/or L-alpha-dimyristoylphosphatidylglycerol.

Concentration of Therapeutic Agent in the Pharmaceutical Composition

The pharmaceutical composition may be characterized according to the concentration of therapeutic agent in the pharmaceutical composition. Accordingly, in certain embodiments, the pharmaceutical composition contains at least one therapeutic agent at a concentration of at least 10 µg/mL. In certain embodiments, the pharmaceutical composition contains at least one therapeutic agent at a concentration of at least 20 µg/mL. In certain embodiments, the pharmaceutical composition contains at least one therapeutic agent at a concentration of at least 50 µg/mL. In certain embodiments, the pharmaceutical composition contains at least one therapeutic agent at a concentration of at least 100 µg/mL. In certain embodiments, the pharmaceutical composition contains at least one therapeutic agent at a concentration of at least 150 µg/mL. In certain embodiments, the pharmaceutical composition contains at least one therapeutic agent at a concentration in the range of about 10 µg/mL to about 1 mg/mL. In certain embodiments, the pharmaceutical composition contains at least one therapeutic agent at a concentration in the range of about 10 µg/mL to about 0.5 mg/mL. In certain embodiments, the pharmaceutical composition contains at least one therapeutic agent at a concentration in the range of about 10 µg/mL to about 250 µg/mL. In certain embodiments, the pharmaceutical composition contains at least one therapeutic agent at a concentration in the range of about 20 µg/mL to about 200 µg/mL. In certain embodiments, the pharmaceutical composition contains at least one therapeutic agent at a concentration in the range of about 200 µg/mL to about 750 µg/mL. In certain embodiments, the pharmaceutical composition contains at least one therapeutic agent at a concentration in the range of about 200 µg/mL to about 400 µg/mL, about 400 µg/mL to about 600 µg/mL, about 500 µg/mL to about 700 µg/mL, or about 600 µg/mL to about 700 µg/mL. In certain embodiments, the pharmaceutical composition contains the therapeutic agent at a concentration in the range of about 1 µg/mL to about 10 µg/mL, about 10 µg/mL to about 50 µg/mL, about 50 µg/mL to about 100 µg/mL, about 100 µg/mL to about 200 µg/mL, 200 µg/mL to about 400 µg/mL, about 400 µg/mL to about 600 µg/mL, about 500 µg/mL to about 700 µg/mL, about 600 µg/mL to about 700 µg/mL, about 700 µg/mL to about 900 µg/mL, about 900 µg/mL to about 1100 µg/mL, about 1100 µg/mL to about 1500 µg/mL, about 1500 µg/mL to about 2000 µg/mL, or about 2000 µg/mL to about 2500 µg/mL.

The concentration of the therapeutic agent may depend upon the choice of therapeutic agent. Accordingly, in certain embodiments when the pharmaceutical composition comprises a therapeutic agent that is topotecan or irinotecan, the pharmaceutical composition can contain a concentration of the therapeutic agent of at least 0.1 µg/mL, at least 0.5 µg/mL, at least 1 µg/mL, at least 1.5 µg/mL, at least 2 µg/mL, at least 2.5 µg/mL, at least 3 µg/mL, at least 3.5 µg/mL, at least 4 µg/mL, at least 4.5 µg/mL, at least 5 µg/mL, at least 5.5 µg/mL, at least 6 µg/mL, at least 6.5 µg/mL, at least 7 µg/mL, at least 7.5 µg/mL, at least 8 µg/mL, at least 8.5 µg/mL, at least 9 µg/mL, at least 10 µg/mL, at least 15 µg/mL, at least 20 µg/mL, at least 30 µg/mL, at least 40 µg/mL, at least 50 µg/mL, at least 60 µg/mL, at least 70 µg/mL, at least 80 µg/mL, at least 90 µg/mL, at least 100 µg/mL, at least 110 µg/mL, at least 120 µg/mL, at least 130 µg/mL, at least 140 µg/mL, at least 150 µg/mL, at least 160 µg/mL, at least 170 µg/mL, at least 180 µg/mL, at least 190 µg/mL, at least 200 µg/mL, at least 250 µg/mL, at least 300 µg/mL, at least 300 µg/mL, at least 300 µg/mL, at least 300 µg/mL, at least 300 µg/mL, or more, inclusive of all ranges and subranges therebetween. In certain embodiments, the pharmaceutical composition can contain a topotecan concentration of at least 0.5 µg/mL. In certain embodiments, the pharmaceutical composition can contain an irinotecan concentration of at least 2.8 µg/mL.

In certain embodiments when the pharmaceutical composition comprises a therapeutic agent that is doxorubicin, paclitaxel, or cisplatin, the pharmaceutical composition can contain a concentration of the therapeutic agent of at least 0.5 µg/mL, at least 1 µg/mL, at least 1.5 µg/mL, at least 2 µg/mL, at least 2.5 µg/mL, at least 3 µg/mL, at least 3.5 µg/mL, at least 4 µg/mL, at least 4.5 µg/mL, at least 5 µg/mL, at least 5.5 µg/mL, at least 6 µg/mL, at least 6.5 µg/mL, at least 7 µg/mL, at least 7.5 µg/mL, at least 8 µg/mL, at least 8.5 µg/mL, at least 9 µg/mL, at least µg/mL, or more, inclusive of all ranges and subranges therebetween. In certain embodiments, the pharmaceutical composition can contain a doxorubicin concentration of at least 1 µg/mL. In certain embodiments, the pharmaceutical composition can contain a paclitaxel concentration of at least 1.2 µg/mL. In certain embodiments, the pharmaceutical composition can contain a cisplatin concentration of at least 1 μg/mL.

In certain embodiments when the pharmaceutical composition comprises a therapeutic agent that is ifosfamide or cyclophosphamide, the pharmaceutical composition can contain a concentration of the therapeutic agent of at least 0.1 μg/mL, at least 0.5 μg/mL, at least 1 μg/mL, at least 2 μg/mL, at least 3 μg/mL, at least 4 μg/mL, at least 5 μg/mL, at least 6 μg/mL, at least 7 μg/mL, at least 8 μg/mL, at least 9 μg/mL, at least 10 μg/mL, at least 11 μg/mL, at least 12 μg/mL, at least 13 μg/mL, at least 14 μg/mL, at least 15 μg/mL, at least 16 μg/mL, at least 17 μg/mL, at least 18 μg/mL, at least 19 μg/mL, at least 20 μg/mL, at least 21 μg/mL, at least 22 μg/mL, at least 23 μg/mL, at least 24 μg/mL, at least 25 μg/mL, or more, inclusive of all ranges and subranges therebetween. In certain embodiments, the pharmaceutical composition can contain an ifosfamide concentration of at least 20 μg/mL. In certain embodiments, the pharmaceutical composition can contain a cyclophosphamide concentration of at least 20 μg/mL.

In certain embodiments when the pharmaceutical composition comprises a therapeutic agent that is carboplatin or oxaliplatin, the pharmaceutical composition can contain a concentration of the therapeutic agent of at least 0.5 μg/mL, at least 1 μg/mL, at least 1.5 μg/mL, at least 2 μg/mL, at least 2.5 μg/mL, at least 3 μg/mL, at least 3.5 μg/mL, at least 4 μg/mL, at least 4.5 μg/mL, at least 5 μg/mL, at least 5.5 μg/mL, at least 6 μg/mL, at least 6.5 μg/mL, at least 7 μg/mL, at least 7.5 μg/mL, at least 8 μg/mL, at least 8.5 μg/mL, at least 9 μg/mL, at least 10 μg/mL, at least 15 μg/mL, at least 20 μg/mL, at least 30 μg/mL, at least 40 μg/mL, at least 50 μg/mL, at least 60 μg/mL, at least 70 μg/mL, at least 80 μg/mL, at least 90 μg/mL, at least 100 μg/mL, or more, inclusive of all ranges and subranges therebetween. In certain embodiments, the pharmaceutical composition can contain a cisplatin concentration of at least 1 μg/mL. In certain embodiments, the pharmaceutical composition can contain an oxaliplatin concentration of at least 1 μg/mL.

In certain embodiments when the pharmaceutical composition comprises a therapeutic agent that is digoxin or vancomycin, the pharmaceutical composition can contain a concentration of the therapeutic agent of at least 0.1 μg/mL, at least 0.5 μg/mL, at least 1 μg/mL, at least 1.5 μg/mL, at least 2 μg/mL, at least 2.5 μg/mL, at least 3 μg/mL, at least 3.5 μg/mL, at least 4 μg/mL, at least 4.5 μg/mL, at least 5 μg/mL, at least 5.5 μg/mL, at least 6 μg/mL, at least 6.5 μg/mL, at least 7 μg/mL, at least 7.5 μg/mL, at least 8 μg/mL, at least 8.5 μg/mL, at least 9 μg/mL, at least μg/mL, at least 15 μg/mL, at least 20 μg/mL, at least 25 μg/mL, at least 30 μg/mL, at least 35 μg/mL, at least 40 μg/mL, at least 45 μg/mL, at least 50 μg/mL, or more.

In certain embodiments when the pharmaceutical composition comprises a therapeutic agent that is imipenem, the pharmaceutical composition can contain a concentration of the therapeutic agent of at least 10 μg/mL, at least 50 μg/mL, at least 100 μg/mL, at least 150 μg/mL, at least 200 μg/mL, at least 250 μg/mL, at least 300 μg/mL, at least 350 μg/mL, at least 350 μg/mL, at least 400 μg/mL, at least 450 μg/mL, at least 500 μg/mL, at least 550 μg/mL, at least 600 μg/mL, at least 650 μg/mL, at least 700 μg/mL, at least 750 μg/mL, at least 800 μg/mL, at least 850 μg/mL, at least 900 μg/mL, at least 950 μg/mL, at least 1000 μg/mL, or more.

Amount of Blood Product in the Pharmaceutical Composition

The pharmaceutical composition may be characterized according to the amount of blood product (e.g., whole blood) in the pharmaceutical composition. Accordingly, in certain embodiments, the blood product constitutes at least 30% wt/wt of the pharmaceutical composition. In certain embodiments, the blood product constitutes at least 40% wt/wt of the pharmaceutical composition. In certain embodiments, the blood product constitutes at least 50% wt/wt of the pharmaceutical composition. In certain embodiments, the blood product constitutes at least 60% wt/wt of the pharmaceutical composition. In certain embodiments, the blood product constitutes at least 75% wt/wt of the pharmaceutical composition. In certain embodiments, the blood product constitutes at least 90% wt/wt of the pharmaceutical composition.

In certain embodiments, the blood product constitutes from about 30% wt/wt to about 99.99% wt/wt of the pharmaceutical composition. In certain embodiments, the blood product constitutes from about 30% wt/wt to about 99.9% wt/wt of the pharmaceutical composition. In certain embodiments, the blood product constitutes from about 60% wt/wt to about 99% wt/wt of the pharmaceutical composition. In certain embodiments, the blood product constitutes from about 70% wt/wt to about 98% wt/wt of the pharmaceutical composition. In certain embodiments, the blood product constitutes from about 70% wt/wt to about 95% wt/wt of the pharmaceutical composition. In certain embodiments, the blood product constitutes from about 75% wt/wt to about 90% wt/wt of the pharmaceutical composition. In certain embodiments, the blood product constitutes from about 80% wt/wt to about 98% wt/wt of the pharmaceutical composition.

In certain embodiments, the blood product constitutes about 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, 99.91%, 99.92%, 99.93%, 99.94%, 99.95%, 99.96%, 99.97%, 99.98%, 99.99%, or more, by weight of the pharmaceutical composition.

In certain embodiments, there is from about 1 mL to about 100 mL of blood product in the pharmaceutical composition. In certain embodiments, there is from about 1 mL to about 25 mL of blood product in the pharmaceutical composition. In certain embodiments, there is from about 25 mL to about 50 mL of blood product in the pharmaceutical composition. In certain embodiments, there is from about 50 mL to about 75 mL of blood product in the pharmaceutical composition. In certain embodiments, there is from about 75 mL to about 100 mL of blood product in the pharmaceutical composition.

In certain embodiments, there is from about 5 mL to about 10 mL of blood product in the pharmaceutical composition, from about 10 mL to about 15 mL of blood product in the pharmaceutical composition, from about 9 mL to about 11 mL of blood product in the pharmaceutical composition, from about 10 mL to about 20 mL of blood product in the pharmaceutical composition, from about 20 mL to about 30 mL of blood product in the pharmaceutical composition, from about 30 mL to about 50 mL of blood product in the pharmaceutical composition, from about 50 mL to about 70 mL of blood product in the pharmaceutical composition, or from about 70 mL to about 90 mL of blood product in the pharmaceutical composition. In certain embodiments, there is from about 90 mL to about 110 mL of blood product in the pharmaceutical composition. In certain embodiments, there is from about 95 mL to about 105 mL of blood product in the pharmaceutical composition. In certain embodiments, there is about 100 mL of blood product in the pharmaceutical composition. In certain embodiments, there is about 150 mL, about 200 mL, about 250 mL, about 300 mL, about 350 mL, about 400 mL, about 450 mL, about 500 mL, or more of blood product in the pharmaceutical composition. In certain embodiments, there is about 100 mL to about 500 mL of blood product in the pharmaceutical composition.

In certain embodiments, the whole blood constitutes at least 30% wt/wt of the pharmaceutical composition. In certain embodiments, the whole blood constitutes at least 40% wt/wt of the pharmaceutical composition. In certain embodiments, the whole blood constitutes at least 50% wt/wt of the pharmaceutical composition. In certain embodiments, the whole blood constitutes at least 60% wt/wt of the pharmaceutical composition. In certain embodiments, the whole blood constitutes at least 75% wt/wt of the pharmaceutical composition. In certain embodiments, the whole blood constitutes at least 90% wt/wt of the pharmaceutical composition. In certain embodiments, the whole blood constitutes from about 60% wt/wt to about 99% wt/wt of the pharmaceutical composition. In certain embodiments, the whole blood constitutes from about 70% wt/wt to about 95% wt/wt of the pharmaceutical composition. In certain embodiments, the whole blood constitutes from about 75% wt/wt to about 90% wt/wt of the pharmaceutical composition. In certain embodiments, there is from about 5 mL to about 10 mL of whole blood in the pharmaceutical composition, from about 10 mL to about 15 mL of whole blood in the pharmaceutical composition, from about 9 mL to about 11 mL of whole blood in the pharmaceutical composition, from about 10 mL to about 20 mL of whole blood in the pharmaceutical composition, from about 20 mL to about 30 mL of whole blood in the pharmaceutical composition, from about 30 mL to about 50 mL of whole blood in the pharmaceutical composition, from about 50 mL to about 70 mL of whole blood in the pharmaceutical composition, or from about 70 mL to about 90 mL of whole blood in the pharmaceutical composition. In certain embodiments, there is from about 90 mL to about 110 mL of whole blood in the pharmaceutical composition. In certain embodiments, there is from about 95 mL to about 105 mL of whole blood in the pharmaceutical composition. In certain embodiments, there is about 100 mL of whole blood in the pharmaceutical composition.

In certain embodiments, whole blood is present in the pharmaceutical composition in an amount of from about 2-15 mL of whole blood per kg of the patient's weight. In certain embodiments, whole blood is present in the pharmaceutical composition in an amount of from about 5-10 mL of whole blood per kg of the patient's weight. In certain embodiments, whole blood is present in the pharmaceutical composition in an amount of from about 10-15 mL of whole blood per kg of the patient's weight.

Volume of the Pharmaceutical Composition

The pharmaceutical composition may be characterized according to its volume. Accordingly, in certain embodiments, the pharmaceutical composition has a volume in the range of about 1 mL to about 200 mL. In certain embodiments, the pharmaceutical composition has a volume in the range of about 1 mL to about 100 mL. In certain embodiments, the pharmaceutical composition has a volume in the range of about 10 mL to about 15 mL, about 15 mL to about 20 mL, about 20 mL to about 30 mL, or about 30 mL to about 50 mL. In certain embodiments, the pharmaceutical composition has a volume in the range of about 1 mL to about 100 mL. In certain embodiments, the pharmaceutical composition has a volume in the range of about 1 mL to about 25 mL. In certain embodiments, the pharmaceutical composition has a volume in the range of about 25 mL to about 50 mL. In certain embodiments, the pharmaceutical composition has a volume in the range of about 50 mL to about 75 mL. In certain embodiments, the pharmaceutical composition has a volume in the range of about 75 mL to about 100 mL. In certain embodiments, the pharmaceutical composition has a volume in the range of about 100 mL to about 125 mL. In certain embodiments, the pharmaceutical composition has a volume in the range of about 125 mL to about 150 mL, about 150 mL to about 200 mL, about 200 mL to about 250 mL, about 300 mL to about 350 mL, about 350 mL to about 450 mL, or about 450 mL to about 500 mL. In certain embodiments, the pharmaceutical composition has a volume of about 500 mL, about 600 mL, about 700 mL, about 800 mL, about 900 mL, about 1000 mL, or more.

Unit Dose Form of the Pharmaceutical Composition

The pharmaceutical composition may be characterized according to the volume of a unit dose of the pharmaceutical composition. Accordingly, in certain embodiments, the pharmaceutical composition is in the form of a unit dose having a volume in the range of about 1 mL to about 200 mL. In certain embodiments, the pharmaceutical composition is in the form of a unit dose having a volume in the range of about 10 mL to about 15 mL, about 15 mL to about 20 mL, about 20 mL to about 30 mL, about 30 mL to about 40 mL, or about 40 mL to about 50 mL. In certain embodiments, the pharmaceutical composition is in the form of a unit dose having a volume in the range of about 50 mL to about 200 mL. In certain embodiments, the pharmaceutical composition is in the form of a unit dose having a volume in the range of about 75 mL to about 150 mL. In certain embodiments, the pharmaceutical composition is in the form of a unit dose having a volume in the range of about 90 mL to about 140 mL.

General Considerations

The therapeutic methods described above may be extended to treatment of additional medical disorders. For example, in certain embodiments, the therapeutic method may be directed to treating (i) a disease involving macrophage activity (e.g., *Mycoplasma tuberculosis* and *Mycoplasma leprae*), (ii) a disease involving monocyte activity, (iii) a disease selected from leprosy, zika virus, *Coxiella burnetti*, Q fever, and HIV, or (iv) heart failure.

The description herein describes multiple aspects and embodiments of the invention. The patent application specifically contemplates all combinations and permutations of the aspects and embodiments.

IV. Kits for Use in Medical Applications

Another aspect of the invention provides a kit for administration of a pharmaceutical composition described herein. The kit comprises: (i) a therapeutic agent described herein, and (ii) instructions for use according to a method described herein.

V. Definitions and General Aspects

To facilitate an understanding of the present invention, a number of terms and phrases are defined below.

The terms "a" and "an" as used herein mean "one or more" and include the plural unless the context is inappropriate.

The term "and/or" is used in this disclosure to mean either "and" or "or" unless indicated otherwise.

It should be understood that the expression "at least one of" includes individually each of the recited objects after the expression and the various combinations of two or more of the recited objects unless otherwise understood from the context and use. The expression "and/or" in connection with three or more recited objects should be understood to have the same meaning unless otherwise understood from the context.

The use of the term "include," "includes," "including," "have," "has," "having," "contain," "contains," or "containing," including grammatical equivalents thereof, should be understood generally as open-ended and non-limiting, for example, not excluding additional unrecited elements or steps, unless otherwise specifically stated or understood from the context.

As used herein, the term "patient" refers to organisms to be treated by the methods of the present invention. Such organisms are preferably mammals (e.g., murines, simians, equines, bovines, porcines, canines, felines, and the like), and more preferably humans. In certain embodiments, the patient is a pediatric human.

As used herein, the term "effective amount" refers to the amount of a compound (e.g., a compound of the present invention) sufficient to effect beneficial or desired results. An effective amount can be administered in one or more administrations, applications or dosages and is not intended to be limited to a particular formulation or administration route.

As used herein, the term "treating" includes any effect, e.g., lessening, reducing, modulating, ameliorating or eliminating, that results in the improvement of the condition, disease, disorder, and the like, or ameliorating a symptom thereof.

As used herein, the terms "alleviate" and "alleviating" refer to reducing the severity of the condition, such as reducing the severity by, for example, at least 10%, 20%, 30%, 40%, 50%, 60%, 70%, 80%, 90%, or 95%.

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see, for example, Martin, Remington's Pharmaceutical Sciences, 15th Ed., Mack Publ. Co., Easton, Pa. [1975].

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metal (e.g., sodium) hydroxides, alkaline earth metal (e.g., magnesium) hydroxides, ammonia, and compounds of formula $NW_3$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

The term "about" as used herein when referring to a measurable value (e.g., weight, time, and dose) is meant to encompass variations, such as +10%, +5%, +1%, or +0.1% of the specified value.

The preparations of the present invention may be given, for example, orally or parenterally. The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Preferably, the compounds are administered at about 0.01 mg/kg to about 200 mg/kg, more preferably at about 0.1 mg/kg to about 100 mg/kg, even more preferably at about 0.5 mg/kg to about 50 mg/kg. When the compounds described herein are co-administered with another agent (e.g., as sensitizing agents), the effective amount may be less than when the agent is used alone.

If desired, the effective daily dose of the active compound may be administered as two, three, four, five, six or more sub-doses administered separately at appropriate intervals throughout the day, optionally, in unit dosage forms. Preferred dosing is one administration per day.

Throughout the description, where compositions and kits are described as having, including, or comprising specific components, or where processes and methods are described as having, including, or comprising specific steps, it is contemplated that, additionally, there are compositions and kits of the present invention that consist essentially of, or consist of, the recited components, and that there are processes and methods according to the present invention that consist essentially of, or consist of, the recited processing steps.

In the application, where an element or component is said to be included in and/or selected from a list of recited elements or components, it should be understood that the element or component can be any one of the recited elements or components, or the element or component can be selected from a group consisting of two or more of the recited elements or components.

Further, it should be understood that elements and/or features of a composition or a method described herein can be combined in a variety of ways without departing from the spirit and scope of the present disclosure, whether explicit or implicit herein. For example, where reference is made to a particular compound, that compound can be used in various embodiments of compositions of the present disclosure and/or in methods of the present disclosure, unless otherwise understood from the context. In other words, within this application, embodiments have been described and depicted in a way that enables a clear and concise application to be written and drawn, but it is intended and will be appreciated that embodiments can be variously combined or separated without parting from the present teachings and disclosure(s). For example, it will be appreciated that all features described and depicted herein can be applicable to all aspects and embodiments of the disclosure(s) described and depicted herein such that the patent application specifically contemplates all combinations and permutations of the aspects and embodiments.

It should be understood that the order of steps or order for performing certain actions is immaterial so long as the present disclosure remain operable. Moreover, two or more steps or actions can be conducted simultaneously.

The use of any and all examples, or exemplary language herein, for example, "such as" or "including," is intended merely to illustrate better the present invention and does not pose a limitation on the scope of the invention unless claimed. No language in the specification should be construed as indicating any non-claimed element as essential to the practice of the present invention.

At various places in the present specification, variables are disclosed in ranges. It is specifically intended that the description include each and every individual subcombination of the members of such ranges. For example, an integer in the range of 0 to 40 is specifically intended to individually disclose 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40, and an integer in the range of 1 to 20 is specifically intended to individually disclose 1, 2, 3, 4, 5, 6, 7, 8, 9, 10, 11, 12, 13, 14, 15, 16, 17, 18, 19, and 20.

As a general matter, compositions specifying a percentage are by weight unless otherwise specified. Further, if a variable is not accompanied by a definition, then the previous definition of the variable controls.

Various aspects of the invention are set forth herein under headings and/or in sections for clarity; however, it is understood that all aspects, embodiments, or features of the invention described in one particular section are not to be limited to that particular section but rather can apply to any aspect, embodiment, or feature of the present invention.

EXAMPLES

The following examples are given for the purpose of illustrating various embodiments of the disclosure and are not meant to limit the present disclosure in any fashion. Changes therein and other uses which are encompassed within the spirit of the disclosure, as defined by the scope of the claims, will be recognized by those skilled in the art.

Example 1. Blood Based Delivery of Carboplatin for Treating Cancer

In this example, human lung cancer cells A549 were xenografted to mice. Mice with xenografted tumors received treatment of either (1) placebo (control, twice in one week), (2) carboplatin (carbo, 50 mg/kg, twice in one week), (3) 50 mg/kg carboplatin mixed with whole blood (blood-mix-carbo, 50 mg/kg, twice in one week), or (4) 100 mg/kg carboplatin mixed with whole blood (blood-mix-carbo, 100 mg/kg, twice in one week).

Compared to control, tumor volume was reduced in mice received carboplatin, and carboplatin mixed with whole blood (either 50 mg/kg or 100 mg/kg). In addition, 100 mg/kg carboplatin mixed with whole blood had the most significant tumor volume reduction, see FIG. 1.

The myelosuppression effect of each treatment was also analyzed by detecting the numbers of white blood cells, red blood cells, and platelets two or three weeks after the treatments. The results indicated that carboplatin mixed with whole blood (either 50 mg/kg or 100 mg/kg) had reduced or comparable toxicity compared to direct administration of carboplatin, see FIGS. 2A, 2B, 3A, 3B, 4A and 4B. Reduced renal toxicity was also observed with the carboplatin+blood mix compared to carboplatin alone at doses of both 50 mg/kg and 100 mg/kg as assessed by BUN and creatinine measurements.

Example 2. Blood Based Delivery of Oxaliplatin for Treating Cancer

In this example, human HT-29 colorectal cancer cells were xenografted to mice. Mice with xenografted tumors received treatment of either (1) placebo (control, one time), (2) oxaliplatin (L-OHP, 12 mg/kg, one time), (3) 12 mg/kg oxaliplatin mixed with whole blood (blood-mix-L-OHP, 12 mg/kg, one time), or (4) 24 mg/kg oxaliplatin mixed with whole blood (blood-mix-carbo, twice in one week).

Figure 5:
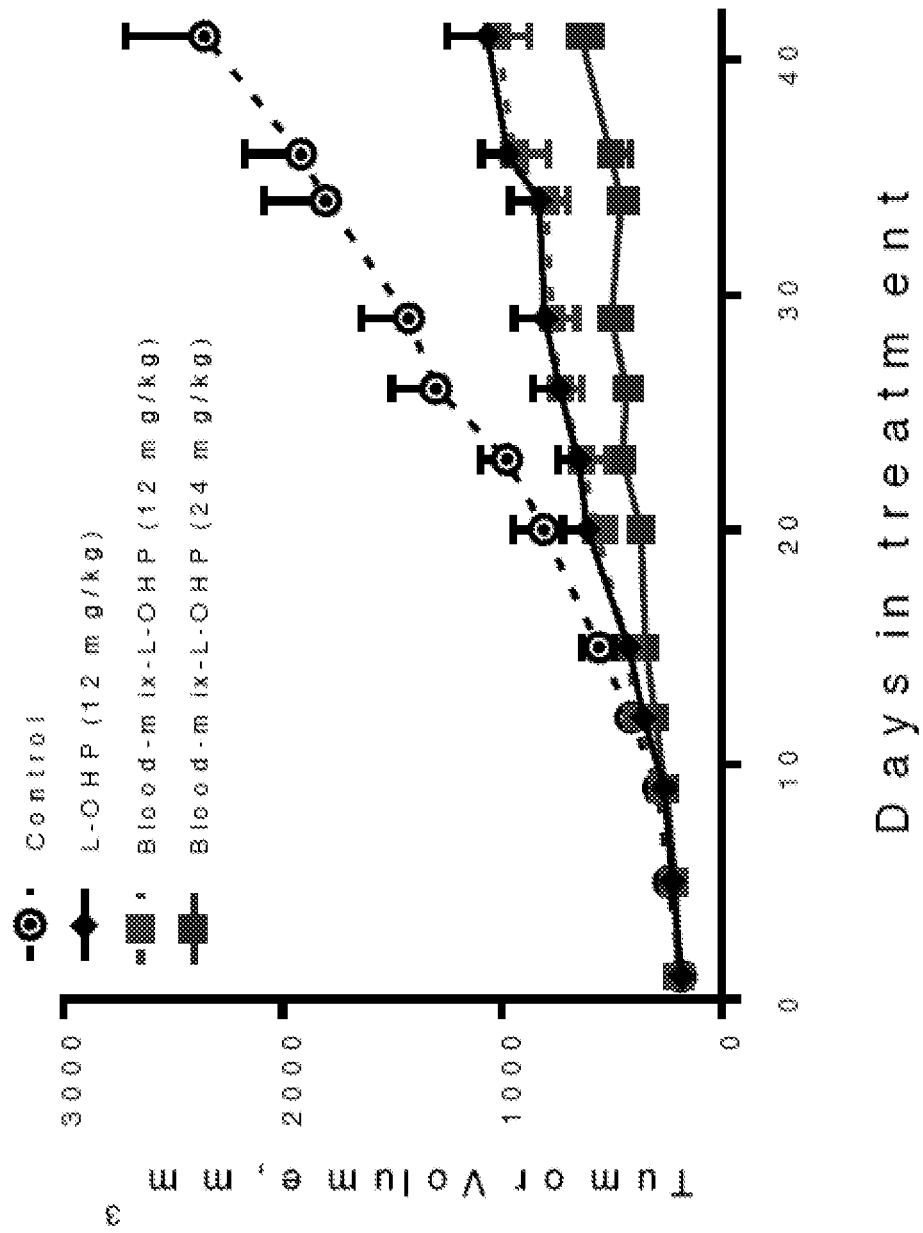
FIG. 5 depicts activity of control, oxaliplatin (L-OHP, 12 mg/kg), and whole blood mixed with oxaliplatin (Blood-mix-L-OHP, either 12 mg/kg or 24 mg/kg) in treating xenografted HT-29 colorectal tumor, as measured by tumor volume over time (0-40 days) after each treatment.

Compared to control, tumor volume was reduced in mice received oxaliplatin, and oxaliplatin mixed with whole blood (either 12 mg/kg or 24 mg/kg). In addition, 24 mg/kg carboplatin mixed with whole blood had the most significant tumor volume reduction, see FIG. 5.

The nephrotoxicity of each treatment was also analyzed by detecting the level of serum creatinine or blood urea nitrogen (BUN). The results indicated that oxaliplatin mixed with whole blood (either 12 mg/kg or 24 mg/kg) had reduced toxicity compared to direct administration of oxaliplatin, see FIGS. 6A and 6B.

Example 3. Blood Based Delivery of Imipenem for Treating Sepsis

Despite treatments, between more than 200,000 people die of sepsis annually in the United States. Early therapy in sepsis is associated with improved overall patient outcome. In this example, it is demonstrated that administration of antibiotic therapy with the help of blood based delivery provides improved treatment efficacy and increased survival rate in mice model. Sepsis model: twenty BALB/c mice (Jackson Labs; 6-8 weeks) were made septic by CLP. Briefly, mice were anesthetized isoflurane (5% induction and 2% maintenance), and subjected to laparotomy. The cecum was exteriorized and ligated distal to the ileocecal valve without causing intestinal obstruction. The cecum was then punctured twice with either a 21 gauge needle, and stool was gently extruded. Lastly, the abdomen was closed 1 mL of saline was injected.

Animals received imipenem (25 mg/kg) or imipenem (25 mg/kg) mixed with blood (100 µL) at 6 and 12 hours following CLP, and continued for 5 days or until death.

Figure 7:
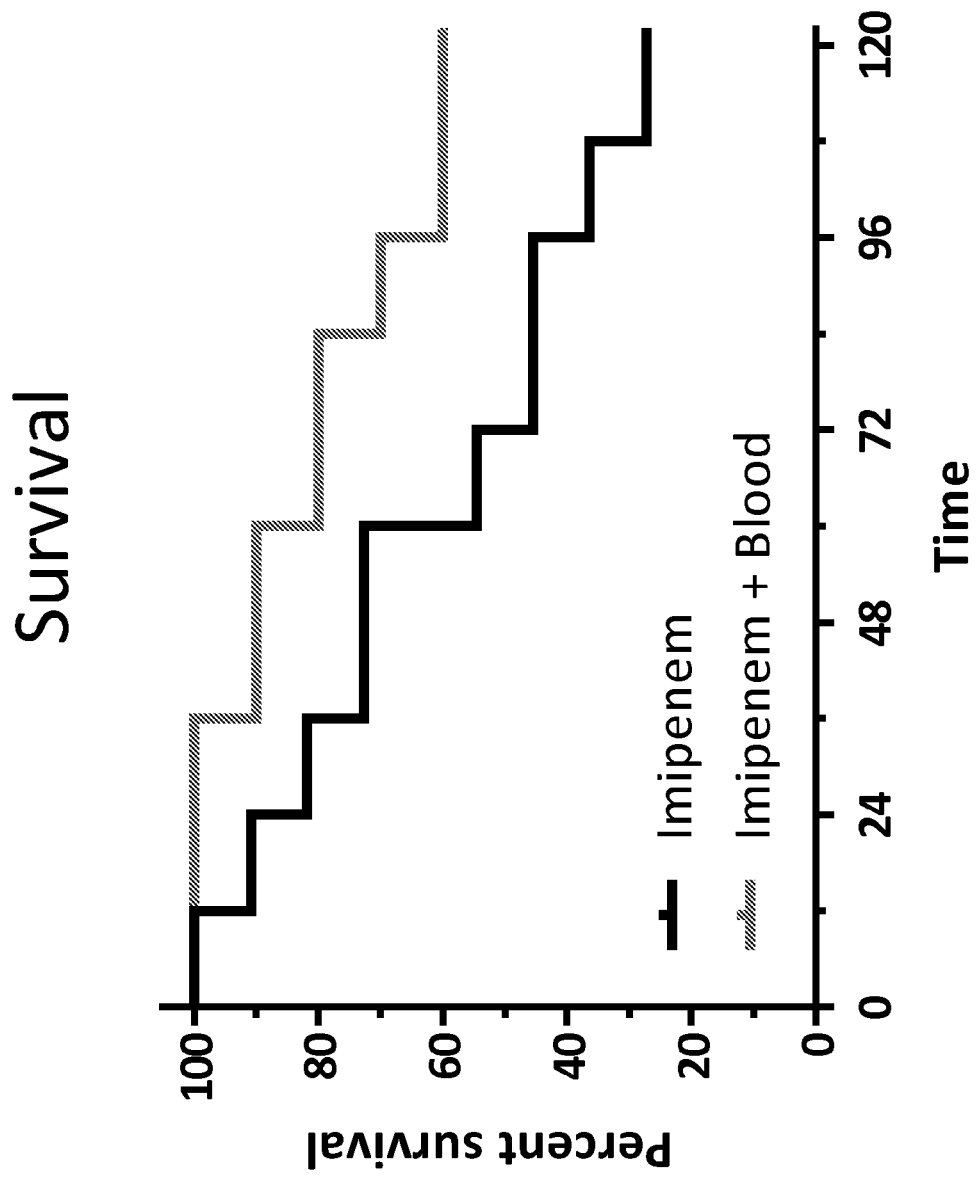
FIG. 7 depicts survival curve of sepsis model mice that received treatment of imipenem or imipenem blood mix. Mice receiving antibiotic therapy mixed with blood had improved overall survival (P>0.1).

The survival rates of mice received imipenem and imipenem blood mix over time are shown in FIG. 7, which is the most important measurement of activity. The results indicated that imipenem blood mix provided higher survival rate compared to direct administration of imipenem.

The results also indicated that mice treated with imipenem blood mix had a lower level of live bacterial count and hence, improved efficacy compared to mice treated with imipenem. More specifically, 24 hour blood samples from septic mice showed significantly ($p<0.05$) higher level of live bacterial count in imipenem (7.4±0.45 log CFU/mL, n=8) compared to imipenem mixed with blood (5.7±0.24 log CFU/mL, n=10).

Example 4. Blood Based Delivery of Paclitaxel for Treating Cancer

Figure 8:
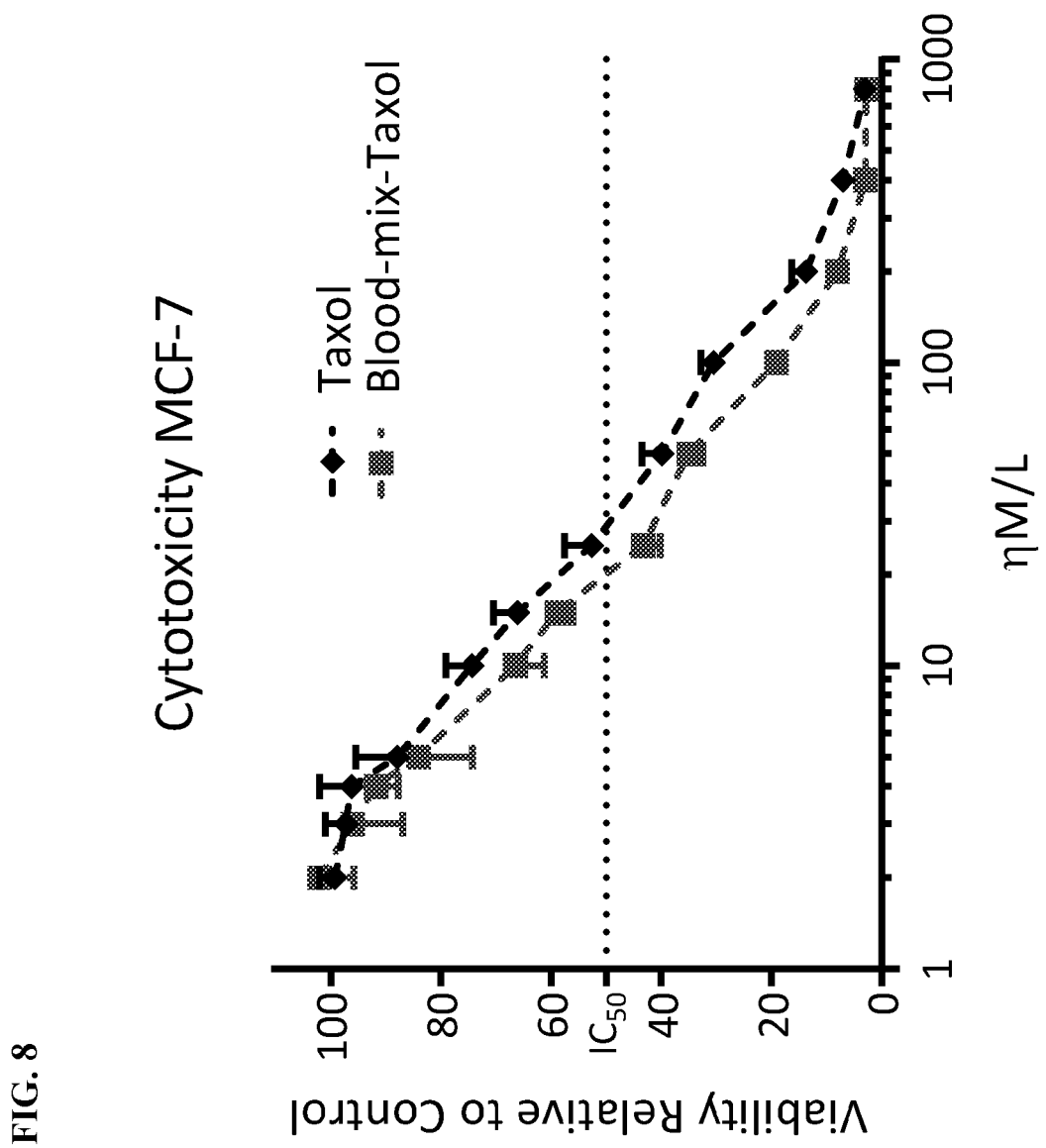
FIG. 8 depicts cytotoxicity of control, paclitaxel (Taxol), and whole blood mixed with paclitaxel (Blood-mix-Taxol) on human breast carcinoma cells MCF7, as measured by viability of the treated cells relative to control cells at each concentration.
Figure 9:
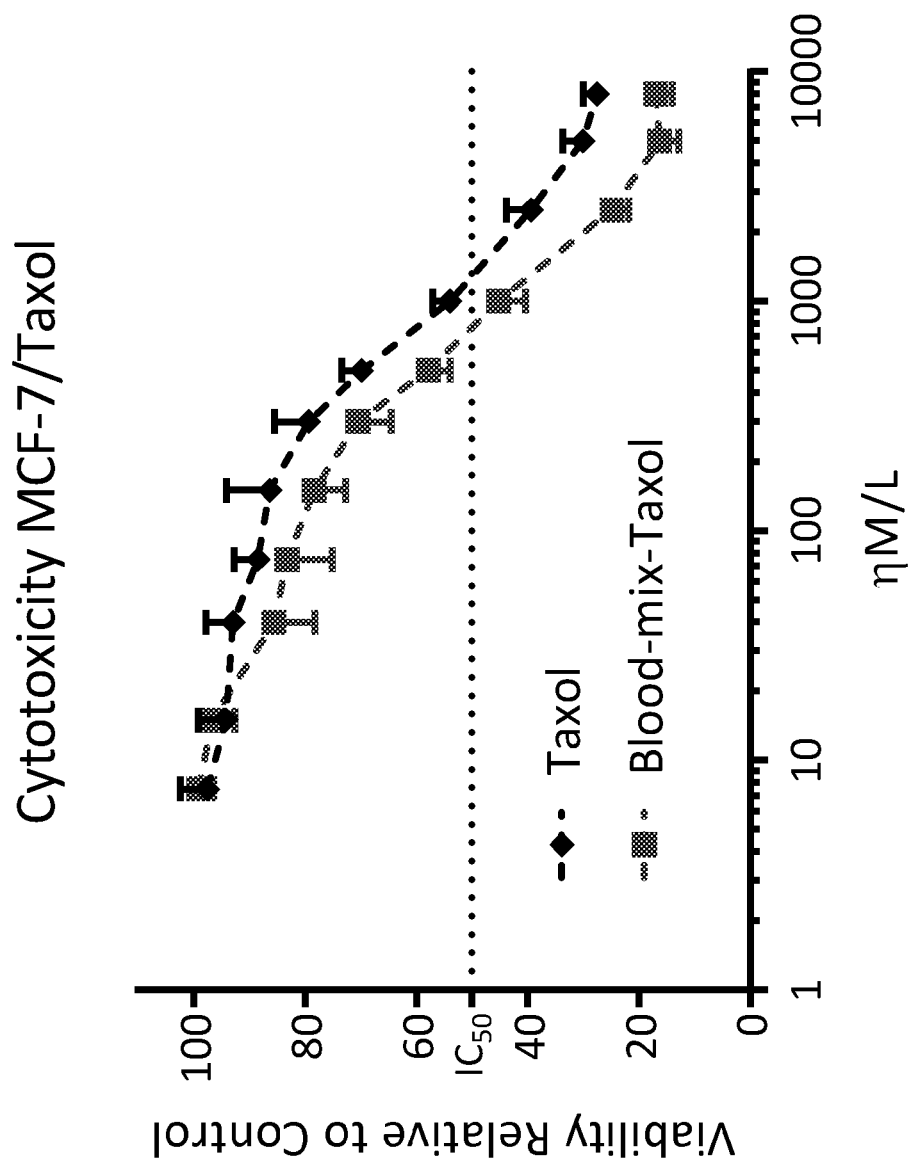
FIG. 9 depicts cytotoxicity of control, paclitaxel (Taxol), and whole blood mixed with paclitaxel (Blood-mix-Taxol) on human breast carcinoma cells MCF7/Taxol (Taxol resistance line), as measured by viability of the treated cells relative to control cells at each concentration.

The cytotoxic effect of paclitaxel blood mix on cancer cells was analyzed in an in vitro tumor model. Human breast carcinoma cells MCF7 (ATCC HTB-22) and MCF7/Taxol (Taxol resistance line) were cultured in DMEM/F12 with 10% fetal bovine serum medium at 5% $CO^2$ and 37° C. The cell cultures were plated at $5\times10^4$ cells per well and randomized into three groups (n=4 per group): (1) cells treated with paclitaxel (Taxol) at various concentrations (0-1000 nm); (2) cells treated with whole blood mixed with paclitaxel (Blood-mix-Taxol) at various concentrations (0-1000 nm); and (3) cells without receiving treatment (Control). The viability of the cells was analyzed using a MTT cell proliferation assay. After 48 hours of treatment, the absorbance of each sample was measured. The viability of the treated cells relative to control cells at each concentration were quantified and shown in FIG. 8 (MCF7 cells) and FIG. 9 (MCF7/Taxol cells). The results indicated that paclitaxel blood mix provided higher cytotoxicity against the breast cancer cells compared to direct treatment of paclitaxel at equivalent concentrations.

The cytotoxic effect of paclitaxel blood mix on cancer cells was further analyzed in an in vivo mouse model. 6-week-old-female athymic mice (nu/nu) were implanted orthotopically with $1\times10^7$ cells/mL human breast carcinoma cells MCF7 or MCF/Taxol (Taxol resistance line) into their mammary fat pad. The mice were randomized into four groups (n=4 per group) based on their treatment: (1) mice received twice per week injection of paclitaxel (Taxol) at 10 mg/kg; (2) mice received twice per week injection of paclitaxel (Taxol) at 30 mg/kg; (3) mice received twice per week injection of paclitaxel blood mix (Blood-mix-Taxol) at 10 mg paclitaxel/kg; (4) mice received twice per week injection of paclitaxel blood mix (Blood-mix-Taxol) at 30 mg paclitaxel/kg; and (5) mice did not receive treatment (control). The treatments started when tumors were 100 mm³. The paclitaxel blood mixes were prepared by incubating whole blood with paclitaxel and an anticoagulant (CPD) for 30 minutes. The volume for paclitaxel blood mix was 100 µL per injection (equivalent to about 125 mL of blood in human).

Figure 10:
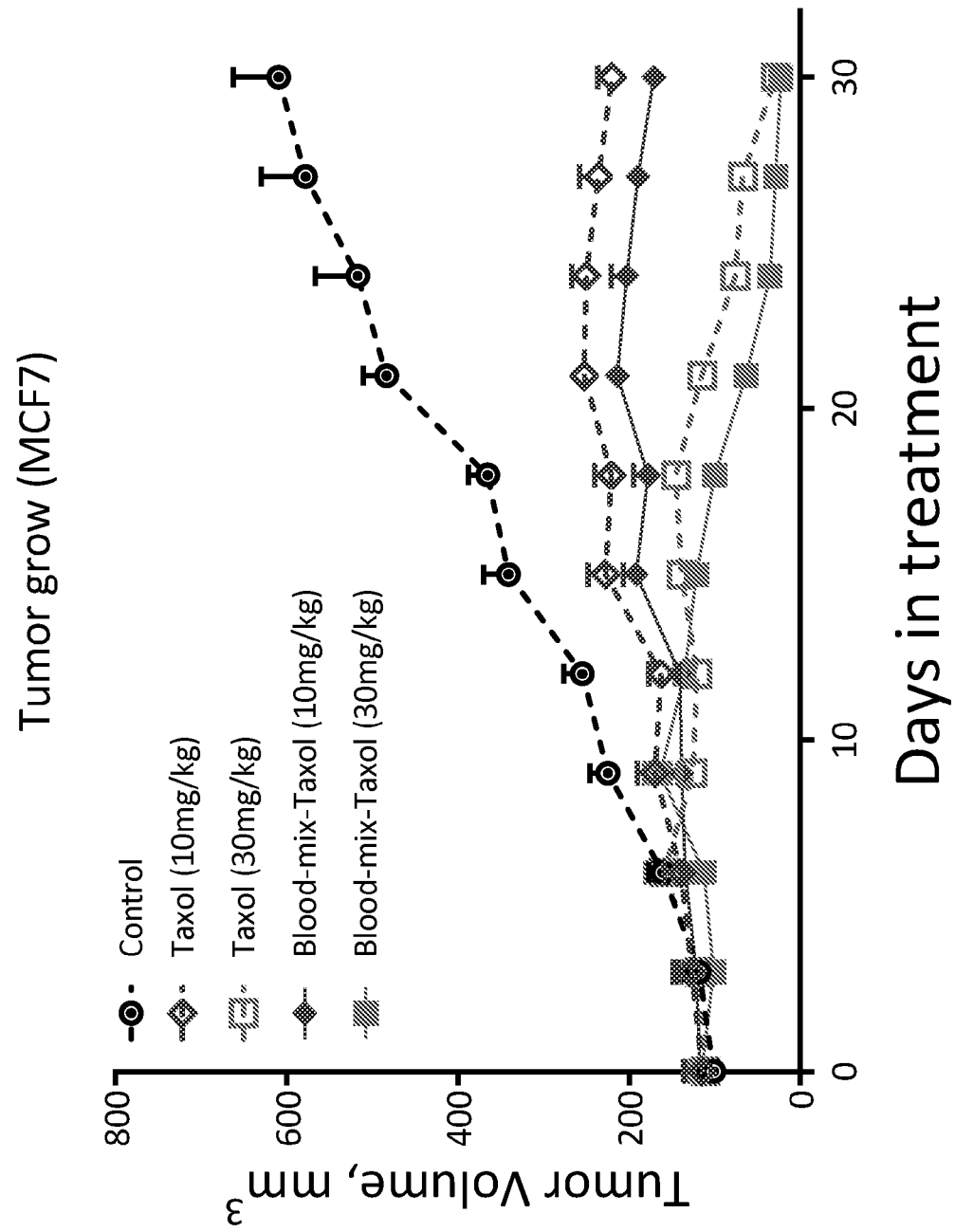
FIG. 10 depicts activity of control, paclitaxel (Taxol, either 10 mg/kg or 30 mg/kg), and whole blood mixed with paclitaxel (Blood-mix-Taxol, either 10 mg/kg or 30 mg/kg) in treating implanted MCF7 colorectal human breast carcinoma, as measured by tumor volume over time (0-30 days).
Figure 12:
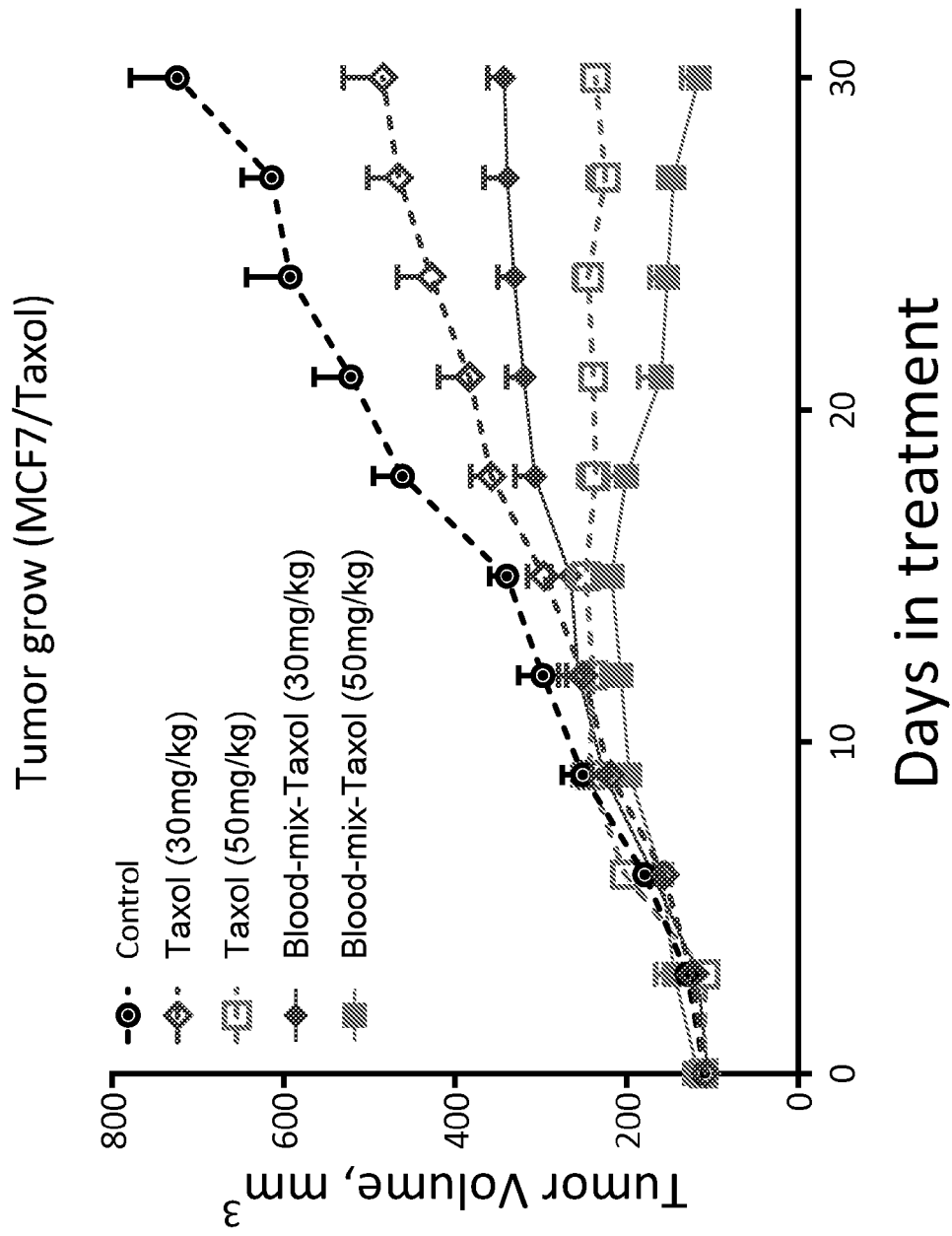
FIG. 12 depicts activity of control, paclitaxel (Taxol, either 10 mg/kg or 30 mg/kg), and whole blood mixed with paclitaxel (Blood-mix-Taxol, either 10 mg/kg or 30 mg/kg) in treating implanted MCF7/Taxol (Taxol resistance line) human breast carcinoma, as measured by tumor volume over time (0-30 days).

As shown in FIG. 10 (MCF7 cells) and FIG. 12 (MCF7/Taxol cells), compared to control, tumor volume was reduced in mice received paclitaxel and paclitaxel mixed with whole blood (either 10 mg/kg or 30 mg/kg). The results also indicated that paclitaxel blood mix injections reduced tumor growth to a greater extent than direct administration of paclitaxel at equivalent concentrations.

Figure 11:
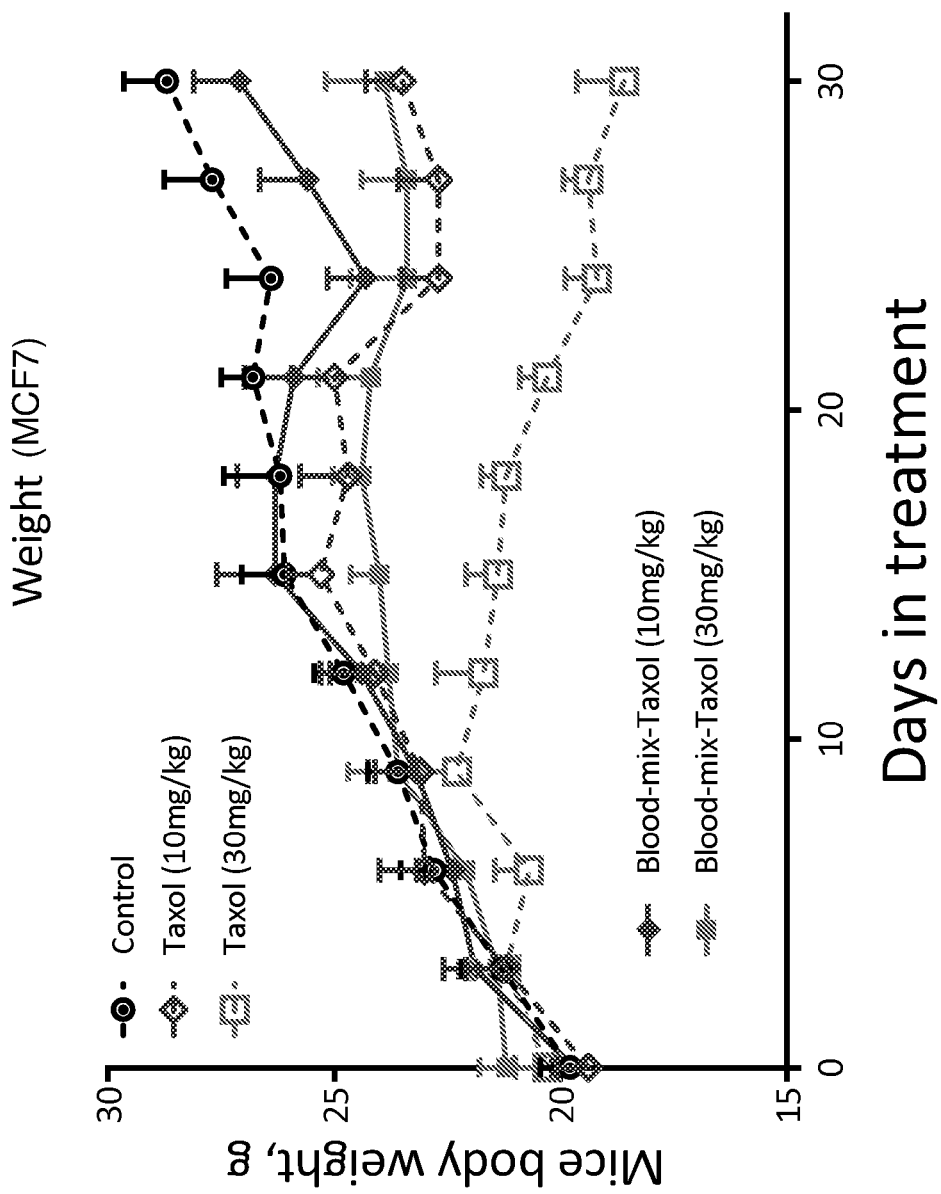
FIG. 11 depicts toxicity of control, paclitaxel (Taxol, either 10 mg/kg or 30 mg/kg), and whole blood mixed with paclitaxel (Blood-mix-Taxol, either 10 mg/kg or 30 mg/kg) on mice implanted with human breast carcinoma cells MCF7, as measured by body weight of the mice over time (0-30 days).
Figure 13:
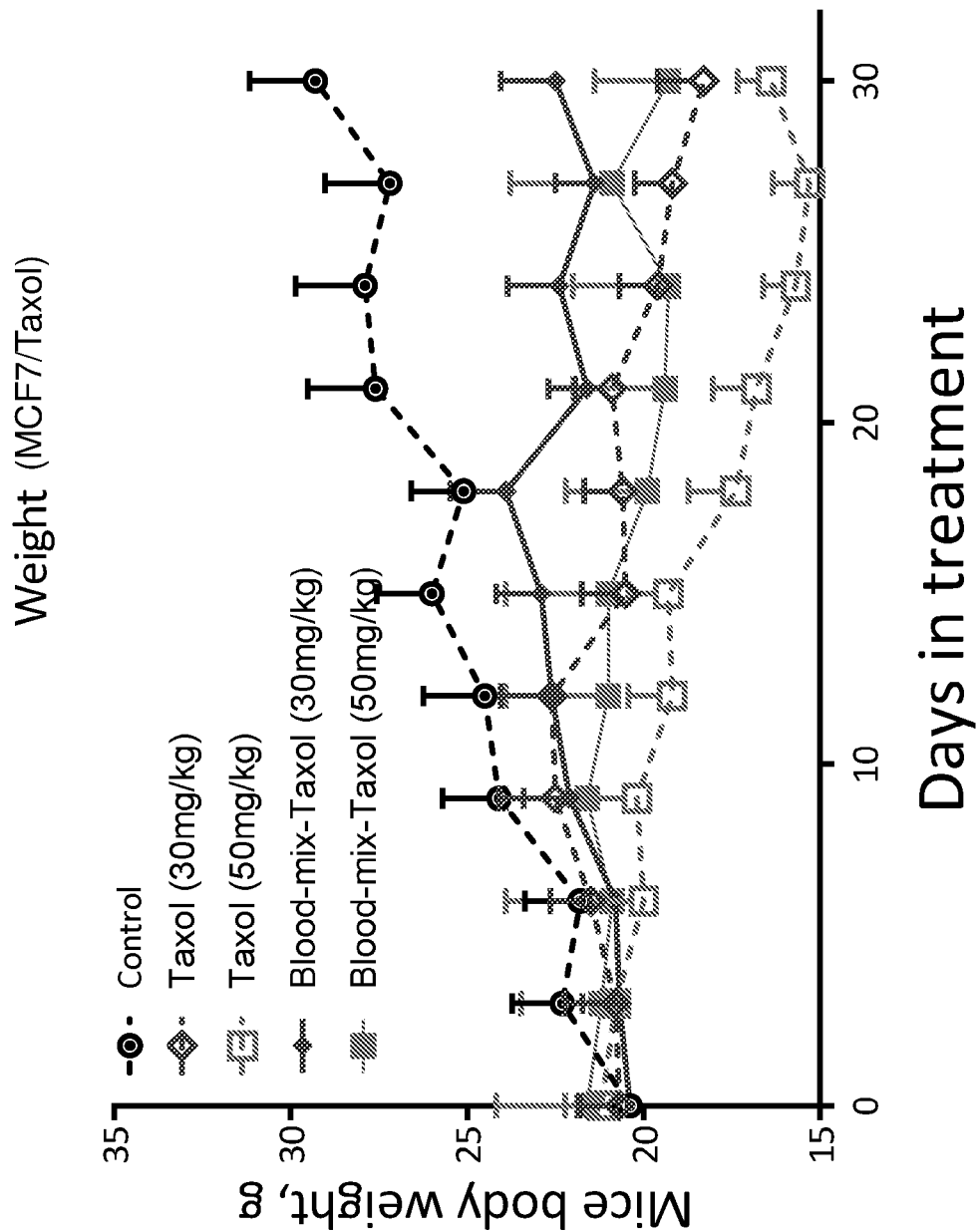
FIG. 13 depicts toxicity of control, paclitaxel (Taxol, either 10 mg/kg or 30 mg/kg), and whole blood mixed with paclitaxel (Blood-mix-Taxol, either 10 mg/kg or 30 mg/kg) on mice implanted with human breast carcinoma cells MCF7/Taxol (Taxol resistance line), as measured by body weight of the mice over time (0-30 days).

Body weight of the mice shows toxicity of the treatment and general health of the mice. As shown in FIG. 11 (MCF7 cells) and FIG. 13 (MCF7/Taxol cells), mice received paclitaxel blood mix injections have a higher body weight than those received paclitaxel at equivalent concentrations. The results indicated that paclitaxel blood mix had reduced toxicity on mice compared to direct administration of paclitaxel at equivalent concentrations.

Examples 5 to 10

A brief table of contents for Examples 5 to 10 is provided below solely for the purpose of assisting the reader. Nothing in this table of contents is meant to limit the scope of the examples or disclosure of the application. The goal of each of these clinical trials is to determine whether the blood mix vs. conventional IV dosing improves toxicity without reducing efficacy at standardly used doses. The clinical trials will show that higher than standard doses of a therapeutic agent/blood mix improves efficacy, with the same or better toxicity profile. The primary endpoint of initial clinical trials is to show reduction in toxicity at a standard dose when a therapeutic agent is mixed with a blood product before being administered to patients, compared to that of the same therapeutic agent without being mixed with the blood product before administration at the same standard dose. The secondary endpoint of these clinical trials is to show efficacy equivalence of the therapeutic agent/blood product mixture compared to the same therapeutic agent being administered alone, at the same dose. In subsequent clinical trials, the primary endpoint is to show efficacy superiority of the therapeutic agent/blood mix at a higher-than-standard dose over the same therapeutic agent being administered alone at the standard dose, and the secondary endpoint is to show toxicity equivalence between the therapeutic agent/blood mix at a higher-than-standard dose and the same therapeutic agent being administered alone at the standard dose. Table 1—Table of Contents For Examples 5-10.

TABLE 1

Table of Contents For Examples 5-10.

| Example | Indication | Control arm | Blood mix arm | Primary hypothesis |
|---|---|---|---|---|
| 5 | Metastatic breast cancer | Anthracycline + cyclophosphamide (AC) normal | AC-blood mix | Superiority based on % cardiac toxicity Efficacy Non-inferiority |
| 6 | Metastatic breast cancer | AC | Anthracycline blood mix + cyclophosphamide normal | Superiority based on % cardiac toxicity (Drug to drug interaction absence possibility) Efficacy Non-inferiority |
| 7 | Metastatic bladder cancer, metastatic anal cancer, metastatic ovarian and metastatic breast cancer | Paclitaxel as a single agent normal | Paclitaxel as a single agent blood mix | Superiority based on % adverse events Efficacy Non-inferiority |
| 8 | SCLC, ovarian and head and neck cancer | Cisplatin normal + other agent such as Paclitaxel or etoposide normal | Cisplatin blood mix + Paclitaxel or etoposide normal | Superiority based on % toxicity (Drug to drug interaction absence possibility) Efficacy Non-inferiority |
| 9 | SCLC lung cancer in second line after failure of platinum | Topotecan normal | Topotecan blood mix | Superiority based on % toxicity Efficacy Non-inferiority |
| 10 | Ovarian lung cancer in second line after failure of platinum | Topotecan normal | Topotecan blood mix | Superiority based on % toxicity Efficacy Non-inferiority |

In Examples 5 to 10 below, an administration labeled as "normal" refers to a direct administration of a therapeutic agent, where the therapeutic agent is not mixed with a blood product prior to administration. Also, the dosage of the therapeutic agent in an administration labeled as "normal" is as the same as the standard dosage normally used by clinicians, e.g., a dosage approved by FDA.

Example 5. Breast Cancer Treatment Using Anthracycline+Cyclophosphamide (Normal) Compared to Anthracycline+Cyclophosphamide in Blood Mix In this example, we will compare anthracycline+cyclophosphamide (normal) versus anthracycline+cyclophosphamide blood mix in terms of cardiac toxicity, and test if the blood mix has comparable efficacy in treating metastatic breast cancer patient. Without wishing to be bound to any particular examples, cardiac toxicity can be monitored through the degree of impairment of left ventricular systolic function, as measured by left ventricular ejection fraction (LVEF). Other ways that can be used to measure cardiac toxicity include, but are not limited to, imaging techniques such as echocardiograms (ECG), multiple-gated acquisition (MUGA) scans, and magnetic resonance imaging, and biomarkers such as B-type naturietic peptide (BNP), N-terminal pro-BNP (NT-proBNP), and troponins. The example will evaluate the superiority of anthracycline+cyclophosphamide blood mix over anthracycline+cyclophosphamide (normal) in treating patients. Other effects, such as reduced arrhythmias, all cause-mortality, ORR, PFS, OS, etc. will also be tested. The superiority may be established by estimating the hazard ratio, or by demonstrating the difference in ORR (RECIST).

Example 6. Breast Cancer Treatment Using Anthracycline+Cyclophosphamide Compared to Blood Mix Anthracycline+Cyclophosphamide (Normal)

In this example, we will compare anthracycline+cyclophosphamide (normal) versus blood mix anthracycline+cyclophosphamide in terms of cardiac toxicity, and test if blood mix composition has comparable efficacy in treating patients having metastatic breast cancer. Without wishing to be bound to any specific examples, cardiac toxicity can be monitored through the degree of impairment of left ventricular systolic function, as measured by left ventricular ejection fraction (LVEF). Other ways that can be used to measure cardiac toxicity include, but are not limited to, imaging techniques such as echocardiograms (ECG), multiple-gated acquisition (MUGA) scans, and magnetic resonance imaging, and biomarkers such as B-type naturietic peptide (BNP), N-terminal pro-BNP (NT-proBNP), and troponins. The example will evaluate the superiority of blood mix anthracycline+cyclophosphamide over anthracycline+cyclophosphamide (normal) in treating patients. Other effects, such as ORR, PFS, OS, etc. will also be tested. The superiority may be established by estimating the hazard ratio, or by demonstrating the difference in ORR (RECIST).

Example 7. Metastatic Bladder Cancer, Metastatic Anal Cancer, Metastatic Ovarian and Metastatic Breast Cancer Treatments Using Paclitaxel as a Single Agent (Normal) Compared to Paclitaxel Blood Mix as a Single Agent In this example, we will compare toxicity of paclitaxel (normal) versus blood mix paclitaxel in terms of bone marrow toxicities, and test if the blood mix composition has comparable efficacy in treating patients having metastatic cancers, such as metastatic bladder cancer, metastatic anal cancer, metastatic ovarian and metastatic breast cancer. The example will evaluate the superiority of paclitaxel blood mix over paclitaxel (normal) in treating patients. Other effects, such as ORR, PFS, OS, etc. will also be tested. The superiority may be established by estimating the hazard ratio, or by demonstrating the difference in ORR (RECIST).

Example 8. SCLC, Ovarian, Head, and Neck Cancer Treatments Using Cisplatin (Normal)+Other Agent Such as Paclitaxel or Etoposide (Normal) Compared to Cisplatin Blood Mix+Paclitaxel or Etoposide (Normal)

In this example, we will compare the toxicity of cisplatin (normal)+other agent such as paclitaxel or etoposide (normal) compared to cisplatin blood mix+paclitaxel or etoposide (normal) in terms of nephrotoxicity in patients with SCLC, ovarian, head, or neck cancer. Without wishing to be bound to any particular examples, nephrotoxicity can be evaluated by the levels of BUN, creatinine, and serum uric acid, and/or decrease in creatinine clearance. The example will evaluate the superiority of cisplatin blood mix+paclitaxel or etoposide (normal) over cisplatin (normal)+paclitaxel or etoposide (normal) in treating patients. Other effects, such as ORR, PFS, OS, etc. will also be tested. The superiority may be established by estimating the hazard ratio, or by demonstrating the difference in ORR (RECIST).

Example 9. SCLC Lung Cancer Treatment in Second Line after Failure of Platinum by Using Topotecan (Normal) Compared to Topotecan Blood Mix In this example, we will compare the toxicity of topotecan (normal) versus topotecan blood mix as a second line treatment of SCLC lung cancer. The example will evaluate the superiority of topotecan blood mix over topotecan (normal) in treating patients (e.g., less percent of patients experiencing toxicity adverse events). Other effects, such as ORR, PFS, OS, etc. will also be tested. The superiority may be established by estimating the hazard ratio, or by demonstrating the difference in ORR (RECIST).

Example 10. Ovarian Lung Cancer Treatment in Second Line after Failure of Platinum by Using Topotecan (Normal) Compared to Topotecan Blood Mix In this example, we will compare the toxicity of topotecan (normal) to topotecan blood mix as a second line treatment for ovarian lung cancer patients after failure of platinum treatment. The example will evaluate the superiority of topotecan blood mix over topotecan (normal) in treating patients (e.g., less percent of patients experiencing toxicity adverse events). Other effects, such as ORR, PFS, OS, etc. will also be tested. The superiority may be established by estimating the hazard ratio, or by demonstrating the difference in ORR (RECIST).

Example 11. Blood Based Delivery of Doxorubicin for Treating Cancer

In this example, human colorectal HT-29 cancer cells will be xenografted to mice. Mice with xenografted tumors will receive treatment of either (1) placebo (control, twice a week for three weeks), (2) doxorubicin (DOX, 5 mg/kg, twice a week for three weeks), (3) 5 mg/kg doxorubicin mixed with whole blood (blood-mix-DOX, 5 mg/kg, twice a week for three weeks), or (4) 10 mg/kg doxorubicin mixed with whole blood (blood-mix-DOX, 10 mg/kg, twice a week for three weeks).

The data will show that compared to control, tumor volume is reduced in mice received doxorubicin, and doxorubicin mixed with whole blood. In addition, doxorubicin (10 mg/kg) mixed with whole blood will have the most significant tumor volume reduction.

The myelosuppression and cardiotoxicity of each treatment will also analyzed by measuring blood cells (white cells, neutrophils, lymphocytes, monocytes, and eosinophils) or troponin level. The results will indicate that doxorubicin mixed with whole blood (either 5 mg/kg or 10 mg/kg) has reduced toxicity compared to direct administration of doxorubicin.

Example 12. Blood Based Delivery of Cisplatin for Treating Cancer

In this example, human colorectal HT-29 cancer cells will be xenografted to mice. Mice with xenografted tumors will receive treatment of either (1) placebo (control, weekly for 3 weeks), (2) cisplatin (CIS, 5 mg/kg, weekly for 3 weeks), (3) 5 mg/kg cisplatin mixed with whole blood (blood-mix-CIS, 5 mg/kg, weekly for 3 weeks), or (4) 10 mg/kg cisplatin mixed with whole blood (blood-mix-CIS, 10 mg/kg, weekly for 3 weeks).

The data will show that compared to control, tumor volume is reduced in mice received cisplatin, and cisplatin mixed with whole blood. In addition, 10 mg/kg cisplatin mixed with whole blood will have the most significant tumor volume reduction.

The nephrotoxicity of each treatment will also analyzed by detecting the level of serum creatinine. The results will indicate that cisplatin mixed with whole blood (either 5 mg/kg or 10 mg/kg) can reduced or comparable toxicity compared to direct administration of cisplatin.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

The invention claimed is:

1. A method for administering a therapeutic agent to a patient, the method comprising intravenously administering to a patient in need thereof a pharmaceutical composition that comprises (i) whole blood mixed ex vivo with (ii) a therapeutic agent administered in a range of about 5 mg/kg to about 100 mg/kg and being selected from the group consisting of: an anthracycline anti-cancer agent, a topoisomerase inhibitor, an oxazaphosphinanyl anti-cancer agent, a nitro-aryl anti-cancer agent, a platinum-based antineoplastic compound, acrylamide, acrylonitrile, bis(4-fluorobenzyl) trisulfide, a cardiac glycoside, an anti-mitotic agent, a nucleoside analog, and an EGFR inhibitor, and the whole blood ranging from about 20% wt./wt. to about 99.99% wt./wt. of the pharmaceutical composition.

2. The method of claim 1, wherein the whole blood is autologous whole blood.

3. The method of claim 1, wherein the patient suffers from cancer.

4. The method of claim 1, wherein the therapeutic agent is an EGFR inhibitor.

5. The method of claim 4, wherein the EGFR inhibitor is erlotinib, gefitinib, lapatinib, vandetanib, neratinib, or osimertinib.

6. The method of claim 1, wherein the therapeutic agent is a nucleoside analog.

7. The method of claim 6, wherein the nucleoside analog is gemcitabine, didanosine, vidarabine, cytarabin, emtricitabine, lamivudine, zalcitabine, abacavir, acyclovir, entecavir, idoxuridine, trifluridine, or any combination thereof.

8. The method of claim 1, wherein the therapeutic agent is an anti-mitotic agent.

9. The method of claim 8, wherein the anti-mitotic agent is paclitaxel.

10. The method of claim 1, further comprising:
intravenously administering to the patient in need thereof an additional pharmaceutical composition that comprises the whole blood mixed ex vivo with an additional therapeutic agent.

11. The method of claim 10, wherein the pharmaceutical composition differs from the additional pharmaceutical composition, and wherein the therapeutic agent differs from the additional therapeutic agent.

12. The method of claim 1, further comprising:
irradiating the pharmaceutical composition with ultraviolet (UV) light prior to intravenously administering the pharmaceutical composition to the patient.

13. The method of claim 1, wherein the whole blood ranges about 30% wt./wt. to about 99.99% wt./wt. of the pharmaceutical composition.

14. The method of claim 1, wherein the therapeutic agent is administered in the range of about 15 mg/kg to about 90 mg/kg.

15. The method of claim 1, wherein the whole blood ranges from about 60% wt./wt. to about 99.99% wt./wt. of the pharmaceutical composition.

16. The method of claim 1, wherein the therapeutic agent comprises the platinum-based antineoplastic compound.

17. The method of claim 16, wherein the platinum-based antineoplastic compound is selected from the group consisting of: carboplatin, oxaliplatin, and cisplatin.

18. The method of claim 1, wherein the therapeutic agent comprises the topoisomerase inhibitor.

19. The method of claim 18, wherein the topoisomerase inhibitor is selected from the group consisting of: irinotecan and topotecan.

20. The method of claim 1, wherein the therapeutic agent comprises the anthracycline anti-cancer agent.

21. The method of claim 20, wherein the anthracycline anti-cancer agent is doxorubicin.

* * * * *